United States Patent
Zhou et al.

(10) Patent No.: US 11,034,649 B2
(45) Date of Patent: *Jun. 15, 2021

(54) BENZOYLGLYCINE DERIVATIVES AND METHODS OF MAKING AND USING SAME

(71) Applicants: Duke University, Durham, NC (US); The University of North Carolina at Chapel Hill, Chapel Hill, NC (US)

(72) Inventors: Pei Zhou, Durham, NC (US); Eric J. Toone, Durham, NC (US); Robert A. Nicholas, Chapel Hill, NC (US); Ramesh Gopalaswamy, Durham, NC (US); Xiaofei Liang, Durham, NC (US); Frank Navas, III, Durham, NC (US)

(73) Assignees: DUKE UNIVERSITY, Durham, NC (US); THE UNIVERSITY OF NORTH CAROLINA AT CHAPEL HILL, Chapel Hill, NC (US)

( * ) Notice: Subject to any disclaimer, the term of this patent is extended or adjusted under 35 U.S.C. 154(b) by 98 days.

This patent is subject to a terminal disclaimer.

(21) Appl. No.: 16/096,611

(22) PCT Filed: Apr. 25, 2017

(86) PCT No.: PCT/US2017/029429
§ 371 (c)(1),
(2) Date: Oct. 25, 2018

(87) PCT Pub. No.: WO2017/189586
PCT Pub. Date: Nov. 2, 2017

(65) Prior Publication Data
US 2019/0367446 A1    Dec. 5, 2019

Related U.S. Application Data

(60) Provisional application No. 62/327,061, filed on Apr. 25, 2016.

(51) Int. Cl.
*C07C 259/06* (2006.01)
*C07D 265/30* (2006.01)
(Continued)

(52) U.S. Cl.
CPC ............ *C07C 259/06* (2013.01); *A61P 31/04* (2018.01); *C07C 237/34* (2013.01); *C07C 259/18* (2013.01); *C07C 311/06* (2013.01); *C07C 317/18* (2013.01); *C07C 317/44* (2013.01); *C07D 203/08* (2013.01); *C07D 203/18* (2013.01); *C07D 207/327* (2013.01); *C07D 213/64* (2013.01); *C07D 263/16* (2013.01); *C07D 265/30* (2013.01);
(Continued)

(58) Field of Classification Search
CPC ... C07C 259/06; C07C 259/18; C07C 311/06; C07C 317/44; C07D 265/30; C07D 295/10; C07D 213/64; C07D 277/40; C07D 335/02; C07D 203/18
See application file for complete search history.

(56) References Cited

U.S. PATENT DOCUMENTS 4,061,650 A     12/1977  Miyoshi et al.
10,550,074 B2 *  2/2020  Zhou ................... C07C 317/44
(Continued)

FOREIGN PATENT DOCUMENTS

WO    2012/031298 A2    3/2012
WO    2015/024010 A2    2/2015
(Continued)

OTHER PUBLICATIONS

PubChem SCHEMBL 10420246, pp. 1-12, create date: Dec. 5, 2007.
(Continued)

*Primary Examiner* — Matthew P Coughlin
(74) *Attorney, Agent, or Firm* — Polsinelli PC; Michelle L. McMullen

(57) ABSTRACT

Disclosed are compounds of formulae: and pharmaceutically acceptable salts thereof, wherein the variables, $R_1$, $R_2$, $R_3$, $R_4$, $R_5$, $R_6$, $R_7$, $R_{11}$, $R_{12}$, $R_{13}$, $R_{14}$, $R_{15}$, $R_{16}$, $R_{17}$, n, and m are defined herein. These compounds are useful for treating Gram-negative bacteria infections. Also disclosed are methods of making these compounds.

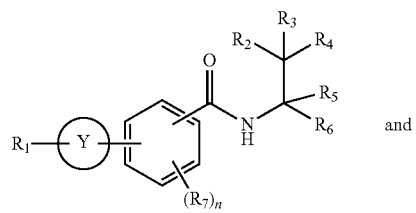

and

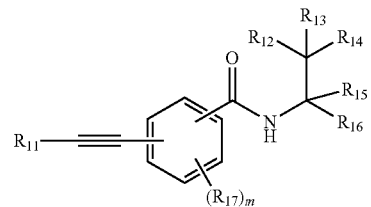

20 Claims, 4 Drawing Sheets

(51) Int. Cl.
*C07D 295/10* (2006.01)
*C07D 213/64* (2006.01)
*C07D 277/40* (2006.01)
*C07D 335/02* (2006.01)
*C07D 203/18* (2006.01)
*C07C 259/18* (2006.01)
*C07C 311/06* (2006.01)
*C07C 317/44* (2006.01)
*C07C 317/18* (2006.01)
*C07C 237/34* (2006.01)
*C07D 207/327* (2006.01)
*C07D 263/16* (2006.01)
*C07D 295/155* (2006.01)
*C07D 203/08* (2006.01)
*C07D 309/10* (2006.01)
*C07D 309/04* (2006.01)
*C07H 15/203* (2006.01)
*A61P 31/04* (2006.01)

(52) U.S. Cl.
CPC ......... *C07D 277/40* (2013.01); *C07D 295/10* (2013.01); *C07D 295/155* (2013.01); *C07D 309/04* (2013.01); *C07D 309/10* (2013.01); *C07D 335/02* (2013.01); *C07H 15/203* (2013.01); *C07C 2601/02* (2017.05); *C07C 2601/08* (2017.05); *C07C 2601/14* (2017.05)

(56) References Cited

U.S. PATENT DOCUMENTS

| | | | |
|---|---|---|---|
| 2011/0190365 A1* | 8/2011 | Werner | C07D 231/38 514/406 |
| 2012/0208809 A1* | 8/2012 | Babin | C07D 207/34 514/232.8 |
| 2013/0072677 A1* | 3/2013 | Takashima | C07D 215/14 540/544 |
| 2013/0231323 A1* | 9/2013 | Zhou | C07D 277/22 514/210.15 |

FOREIGN PATENT DOCUMENTS

| | | |
|---|---|---|
| WO | 2015/024011 A2 | 2/2015 |
| WO | 2014/165075 A1 | 10/2015 |

OTHER PUBLICATIONS

PubChem SCHEMBL 15237908, pp. 1-12, create date: Feb. 13, 2015.

International Search Report and Written Opinion for International Application No. PCT/US2017/029429, dated Jul. 25, 2017.

\* cited by examiner compound 4

Figure 1, continued
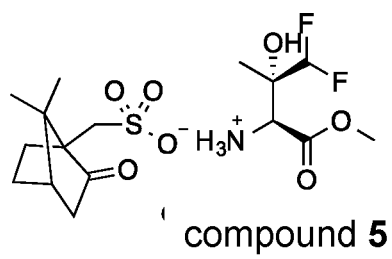
compound 5
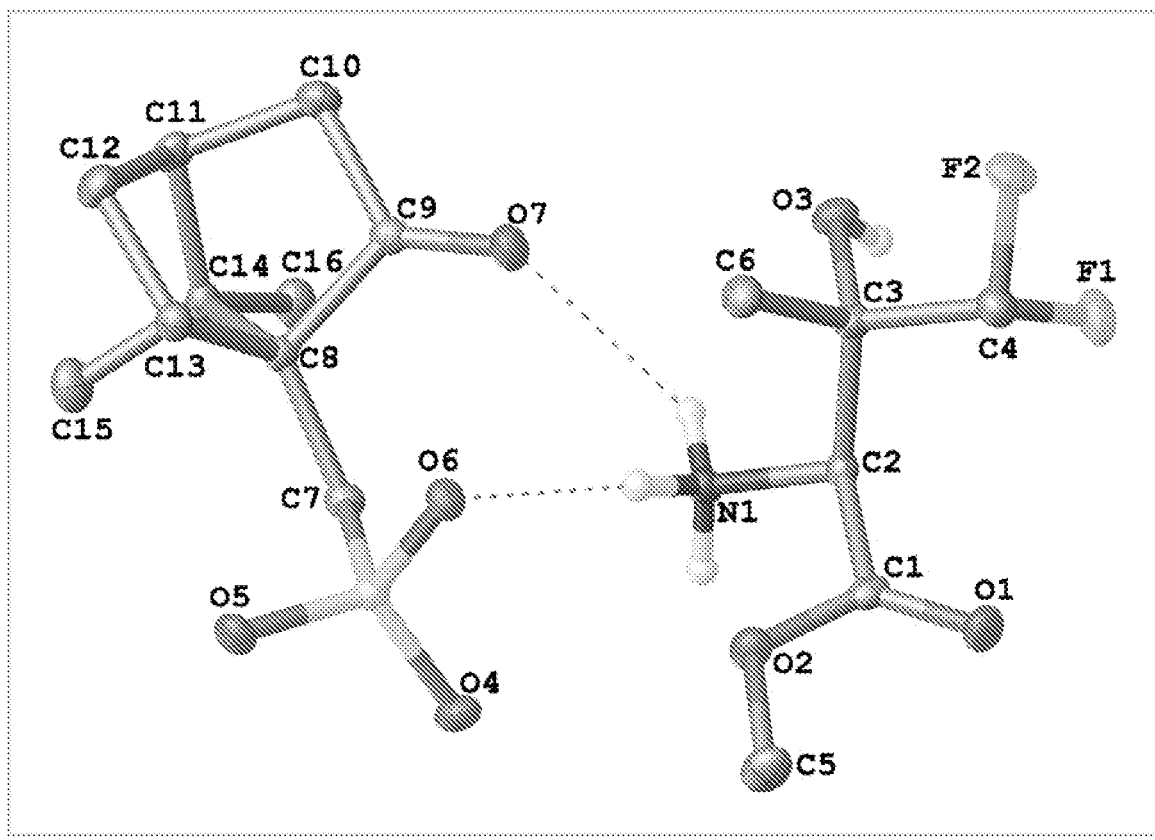

BENZOYLGLYCINE DERIVATIVES AND METHODS OF MAKING AND USING SAME

CROSS-REFERENCE TO RELATED APPLICATIONS

This application is a national stage application under 35 U.S.C. § 371 of International Application No. PCT/US2017/029429, filed Apr. 25, 2017. which claims the benefit of U.S. Provisional Patent Application No. 62/327,061, filed Apr. 25, 2016, which are incorporated herein by reference in their entireties.

STATEMENT REGARDING FEDERALLY SPONSORED RESEARCH OR DEVELOPMENT

This invention was made with United States government support awarded by NIH Grant Nos. AI094475 and AI055588, and Duke CTSA funded by NIH (UL1TR001117). The United States government has certain rights in this invention.

BACKGROUND OF THE INVENTION

Field of the Invention

This invention relates to substituted hydroxamic acid compounds, and in particular, to such compounds that inhibit UDP-3-O—(R-3-hydroxydecanoyl)-N-acetylglucosamine deacetylase (LpxC), and to methods of using such compounds to treat Gram-negative bacterial infections.

Description of the Related Art

Antimicrobial resistance is increasing and becoming alarmingly common. This problem is compounded when bacterial strains are resistant to multiple antibacterial compounds. There clearly is a need for new antibacterial compounds, particularly antibacterial compounds with novel mechanisms of action.

The gene lpxC encodes the enzyme uridyldiphospho-3-O—(R-hydroxydecanoyl)-N-acetylglucosamine deacetylase (LpxC). This enzyme is involved in the synthesis of lipid A, the lipid moiety of lipopolysaccharide, which is an essential component of all Gram-negative bacteria. Commercially useful LpxC inhibitors would need to both inhibit the enzymatic activity of LpxC from a variety of bacteria and defeat the resistance mechanisms of Gram-negative bacteria.

SUMMARY OF THE INVENTION

In a broad aspect, the disclosure encompasses the compounds of formulae I and II, shown below, pharmaceutical compositions containing those compounds and methods of using such compounds to treat and/or prevent bacterial infections.

Thus, one aspect (embodiment 1) of the disclosure provides compounds of formula I:

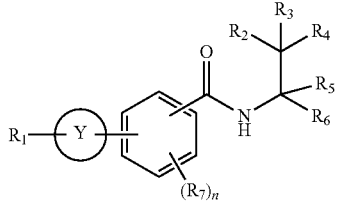

I or a pharmaceutically acceptable salt thereof, wherein
Y represents aryl optionally substituted with $R_8$, heteroaryl optionally substituted with $R_8$, or heterocyclyl optionally substituted with $R_8$;
n is an integer 0, 1, 2, 3, or 4;
$R_1$ is hydrogen, $C_1$-$C_6$ alkyl optionally substituted with $R_9$, aryl optionally substituted with $R_8$, heteroaryl optionally substituted with $R_9$, or heterocyclyl optionally substituted with $R_8$;
$R_2$ is selected from the group consisting of halogen, $C_1$-$C_6$ alkyl, $C_1$-$C_6$ haloalkyl, —$NH_2$, —NH($C_1$-$C_6$ alkyl), —N($C_1$-$C_6$ alkyl)$_2$, —OH, $C_1$-$C_6$ alkoxy, $C_1$-$C_6$ haloalkoxy, —SH, —S($C_1$-$C_6$ alkyl), hydroxy($C_1$-$C_6$ alkyl), alkoxy($C_1$-$C_6$ alkyl), and amino($C_1$-$C_6$ alkyl);
$R_3$ is selected from the group consisting of halogen, $C_1$-$C_6$ alkyl, $C_1$-$C_6$ haloalkyl, —$NH_2$, —NH($C_1$-$C_6$ alkyl), —N($C_1$-$C_6$ alkyl)$_2$, —OH, $C_1$-$C_6$ alkoxy, $C_1$-$C_6$ haloalkoxy, —SH, —S($C_1$-$C_6$ alkyl), hydroxy($C_1$-$C_6$ alkyl), alkoxy($C_1$-$C_6$ alkyl), amino($C_1$-$C_6$ alkyl), —NHCO($C_1$-$C_6$ alkyl), —NHCONH$_2$, —NHCONH($C_1$-$C_6$ alkyl), —OCO($C_1$-$C_6$ alkyl), and —NHCO($C_1$-$C_6$ alkoxy);
$R_4$ is $C_1$-$C_6$ haloalkyl;
$R_5$ is independently selected from the group consisting of halogen, —$NO_2$, —CN, $C_1$-$C_6$ alkyl, $C_1$-$C_6$ haloalkyl, —$NH_2$, —NH($C_1$-$C_6$ alkyl), —N($C_1$-$C_6$ alkyl)$_2$, —OH, $C_1$-$C_6$ alkoxy, $C_1$-$C_6$ haloalkoxy, —CONH$_2$, —CON($C_1$-$C_6$ alkyl), —CON($C_1$-$C_6$ alkyl)$_2$, —CONH—OH, —CONH—OCO($C_1$-$C_6$ alkyl), —CONH—NH$_2$, —CO$_2$H, and —CO$_2$($C_1$-$C_6$ alkyl);
$R_6$ is hydrogen or $C_1$-$C_6$ alkyl;
each $R_7$ is independently selected from the group consisting of halogen, —$NO_2$, —CN, $C_1$-$C_6$ alkyl, $C_1$-$C_6$ haloalkyl, —$NH_2$, —NH($C_1$-$C_6$ alkyl), —N($C_1$-$C_6$ alkyl)$_2$, —OH, $C_1$-$C_6$ alkoxy, and $C_1$-$C_6$ haloalkoxy;
each $R_8$ is independently selected from the group consisting of halogen, —$NO_2$, —CN, $C_1$-$C_6$ alkyl, $C_1$-$C_6$ haloalkyl, —$NH_2$, —NH($C_1$-$C_6$ alkyl), —N($C_1$-$C_6$ alkyl)$_2$, —OH, $C_1$-$C_6$ alkoxy, $C_1$-$C_6$ haloalkoxy, —CONH$_2$, —CON($C_1$-$C_6$ alkyl), —CON($C_1$-$C_6$ alkyl)$_2$, —CONH—OH, —CONH—OCO($C_1$-$C_6$ alkyl), —C(NH)NH—OH, —CONH—NH$_2$, —CO$_2$H, and —CO$_2$($C_1$-$C_6$ alkyl); or two $R_8$ groups when attached to the same carbon atom form =O; and
each $R_9$ is independently selected from the group consisting of halogen, —$NO_2$, —CN, $C_1$-$C_6$ alkyl, $C_1$-$C_6$ haloalkyl, —$NH_2$, —NH($C_1$-$C_6$ alkyl), —N($C_1$-$C_6$ alkyl)$_2$, —OH, $C_1$-$C_6$ alkoxy, and $C_1$-$C_6$ haloalkoxy; or two $R_9$ groups when attached to the same carbon atom form =O.

One aspect (embodiment 34) of the disclosure provides compounds of formula II:

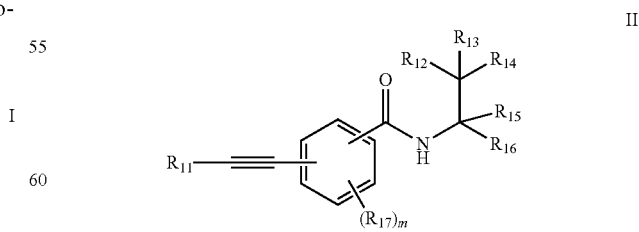

II or a pharmaceutically acceptable salt thereof, wherein
m is an integer 0, 1, 2, 3, or 4;
$R_{11}$ is —C≡C—$R_{10}$, $C_1$-$C_6$ alkyl, $C_1$-$C_6$ haloalkyl, —CO($C_1$-$C_6$ alkyl), —$C_1$-$C_6$ alkyl-CO($C_1$-$C_6$ alkyl), —$C_1$-$C_6$ alkyl-CO$_2$H, C$_3$-C$_8$ cycloalkyl optionally substituted with R$_{18}$, (C$_3$-C$_8$ cycloalkyl)C$_1$-C$_6$ alkyl- optionally substituted with R$_{18}$, or heterocyclyl optionally substituted with R$_{18}$;

wherein R$_{10}$ is C$_1$-C$_6$ alkyl, C$_1$-C$_6$ haloalkyl, —CO(C$_1$-C$_6$ alkyl), —C$_1$-C$_6$ alkyl-CO(C$_1$-C$_6$ alkyl), —C$_1$-C$_6$ alkyl-CO$_2$H, C$_3$-C$_8$ cycloalkyl optionally substituted with R$_{19}$, (C$_3$-C$_8$ cycloalkyl)C$_1$-C$_6$ alkyl- optionally substituted with R$_{19}$, or heterocyclyl optionally substituted with R$_{19}$;

R$_{12}$ is selected from the group consisting of halogen, C$_1$-C$_6$ alkyl, C$_1$-C$_6$ haloalkyl, —NH$_2$, —NH(C$_1$-C$_6$ alkyl), —N(C$_1$-C$_6$ alkyl)$_2$, —OH, C$_1$-C$_6$ alkoxy, C$_1$-C$_6$ haloalkoxy, —SH, —S(C$_1$-C$_6$ alkyl), hydroxy(C$_1$-C$_6$ alkyl), alkoxy(C$_1$-C$_6$ alkyl), and amino(C$_1$-C$_6$ alkyl);

R$_{13}$ is selected from the group consisting of halogen, C$_1$-C$_6$ alkyl, C$_1$-C$_6$ haloalkyl, —NH$_2$, —NH(C$_1$-C$_6$ alkyl), —N(C$_1$-C$_6$ alkyl)$_2$, —OH, C$_1$-C$_6$ alkoxy, C$_1$-C$_6$ haloalkoxy, —SH, —S(C$_1$-C$_6$ alkyl), hydroxy(C$_1$-C$_6$ alkyl), alkoxy(C$_1$-C$_6$ alkyl), amino(C$_1$-C$_6$ alkyl), —NHCO(C$_1$-C$_6$ alkyl), —NHCONH$_2$, —NHCONH(C$_1$-C$_6$ alkyl), —OCO(C$_1$-C$_6$ alkyl), and —NHCO(C$_1$-C$_6$ alkoxy);

R$_{14}$ is C$_1$-C$_6$ haloalkyl;

R$_{15}$ is independently selected from the group consisting of halogen, —NO$_2$, —CN, C$_1$-C$_6$ alkyl, C$_1$-C$_6$ haloalkyl, —NH$_2$, —NH(C$_1$-C$_6$ alkyl), —N(C$_1$-C$_6$ alkyl)$_2$, —OH, C$_1$-C$_6$ alkoxy, C$_1$-C$_6$ haloalkoxy, —CONH$_2$, —CON(C$_1$-C$_6$ alkyl), —CON(C$_1$-C$_6$ alkyl)$_2$, —CONH—OH, —CONH—OCO(C$_1$-C$_6$ alkyl), —CONH—NH$_2$, —CO$_2$H, and —CO$_2$(C$_1$-C$_6$ alkyl);

R$_{16}$ is hydrogen or C$_1$-C$_6$ alkyl;

each R$_{17}$ is independently selected from the group consisting of halogen, —NO$_2$, —CN, C$_1$-C$_6$ alkyl, C$_1$-C$_6$ haloalkyl, —NH$_2$, —NH(C$_1$-C$_6$ alkyl), —N(C$_1$-C$_6$ alkyl)$_2$, —OH, C$_1$-C$_6$ alkoxy, and C$_1$-C$_6$ haloalkoxy;

each R$_{18}$ is independently selected from the group consisting of halogen, —NO$_2$, —CN, C$_1$-C$_6$ alkyl, C$_1$-C$_6$ haloalkyl, —NH$_2$, —NH(C$_1$-C$_6$ alkyl), —N(C$_1$-C$_6$ alkyl)$_2$, —OH, C$_1$-C$_6$ alkoxy, C$_1$-C$_6$ haloalkoxy, —C$_1$-C$_6$ alkyl-OH, —C$_1$-C$_6$ alkyl-(C$_1$-C$_6$ alkoxy), —C$_1$-C$_6$ alkyl-NH$_2$, —C$_1$-C$_6$ alkyl-NH—C$_1$-C$_6$ alkyl), —C$_1$-C$_6$ alkyl-N(C$_1$-C$_6$ alkyl)$_2$, —C$_1$-C$_6$ alkyl-NH(SO$_2$C$_1$-C$_6$ alkyl), —CONH$_2$, —CON(C$_1$-C$_6$ alkyl), —CON(C$_1$-C$_6$ alkyl)$_2$, —NH(SO$_2$C$_1$-C$_6$ alkyl), —CONH—OH, —CONH—OCO(C$_1$-C$_6$ alkyl), —C(NH)NH—OH, —CONH—NH$_2$, —CO(C$_1$-C$_6$ alkyl), —CO$_2$H, —CO$_2$(C$_1$-C$_6$ alkyl), —C$_1$-C$_6$ alkyl-CONH$_2$, —C$_1$-C$_6$ alkyl-CON(C$_1$-C$_6$ alkyl), —C$_1$-C$_6$ alkyl-CON(C$_1$-C$_6$ alkyl)$_2$, —C$_1$-C$_6$ alkyl-CONH—OH, —C$_1$-C$_6$ alkyl-CO(C$_1$-C$_6$ alkyl), —C$_1$-C$_6$ alkyl-CO$_2$H, and —C$_1$-C$_6$ alkyl-CO$_2$(C$_1$-C$_6$ alkyl); or two R$_{18}$ groups when attached to the same carbon atom form =O; and each R$_{19}$ is independently selected from the group consisting of halogen, —NO$_2$, —CN, C$_1$-C$_6$ alkyl, C$_1$-C$_6$ haloalkyl, —NH$_2$, —NH(C$_1$-C$_6$ alkyl), —N(C$_1$-C$_6$ alkyl)$_2$, —OH, C$_1$-C$_6$ alkoxy, C$_1$-C$_6$ haloalkoxy, —C$_1$-C$_6$ alkyl-OH, —C$_1$-C$_6$ alkyl-(C$_1$-C$_6$ alkoxy), —C$_1$-C$_6$ alkyl-NH$_2$, —C$_1$-C$_6$ alkyl-NH—C$_1$-C$_6$ alkyl), —C$_1$-C$_6$ alkyl-N(C$_1$-C$_6$ alkyl)$_2$, —C$_1$-C$_6$ alkyl-NH(SO$_2$C$_1$-C$_6$ alkyl), —CONH$_2$, —CON(C$_1$-C$_6$ alkyl), —CON(C$_1$-C$_6$ alkyl)$_2$, —NH(SO$_2$C$_1$-C$_6$ alkyl), —CONH—OH, —CONH—OCO(C$_1$-C$_6$ alkyl), —C(NH)NH—OH, —CONH—NH$_2$, —CO(C$_1$-C$_6$ alkyl), —CO$_2$H, —CO$_2$(C$_1$-C$_6$ alkyl), —C$_1$-C$_6$ alkyl-CONH$_2$, —C$_1$-C$_6$ alkyl-CON(C$_1$-C$_6$ alkyl), —C$_1$-C$_6$ alkyl-CON(C$_1$-C$_6$ alkyl)$_2$, —C$_1$-C$_6$ alkyl-CONH—OH, —C$_1$-C$_6$ alkyl-CO(C$_1$-C$_6$ alkyl), —C$_1$-C$_6$ alkyl-CO$_2$H, and —C$_1$-C$_6$ alkyl-CO$_2$(C$_1$-C$_6$ alkyl); or two R$_{19}$ groups when attached to the same carbon atom form =O.

The disclosure also provides pharmaceutical compositions comprising a compound of formula I or formula II or a pharmaceutically acceptable salt thereof and at least one pharmaceutically acceptable carrier, solvent, adjuvant or diluent.

The disclosure also provides methods for inhibiting UDP-3-O—(R-3-hydroxydecanoyl)-N-acetylglucosamine deacetylase (LpxC), and methods of treating Gram-negative bacterial infections.

The disclosure further provides a compound or pharmaceutical composition thereof in a kit with instructions for using the compound or composition.

The disclosure also provides synthetic intermediates that are useful in making the compounds of formula I or formula II. Thus, one aspect provides compounds that are:

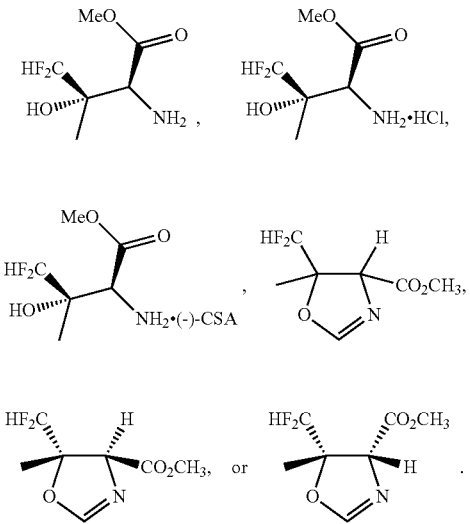

One aspect of the disclosure provides crystalline forms of:

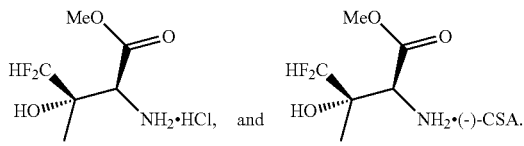

The disclosure also provides methods of preparing compounds of the disclosure and the intermediates used in those methods. Thus, one aspect provides methods for preparing a compound of formula:

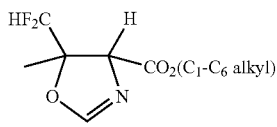

or a salt thereof, the method comprising reacting 1,1-difluoroacetone and C$_{1-6}$ alkyl α-isocyanoacetate in presence of transition metal catalyst and base.

One aspect provides methods for preparing a compound of formula:

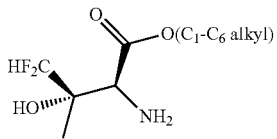

or a salt thereof, the method comprising reacting 1,1-difluoroacetone and $C_1$-$C_6$ alkyl α-isocyanoacetate in presence of transition metal catalyst and base to obtain oxazoline of formula:

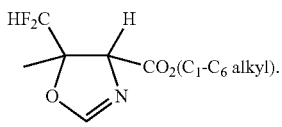

One aspect provides methods for preparing the compounds of the disclosure, the method comprising coupling a compound of formula: with a compound of formula:

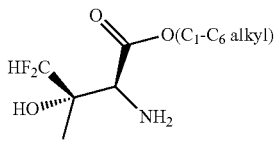

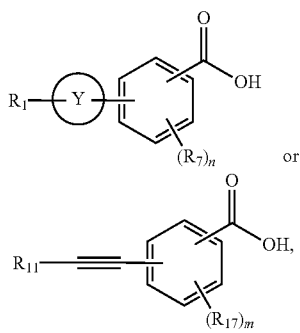

wherein Y, $R_1$, $R_{11}$, $R_7$, $R_{17}$, m and n are as defined in above.

One aspect provides methods for preparing a compound of formula:

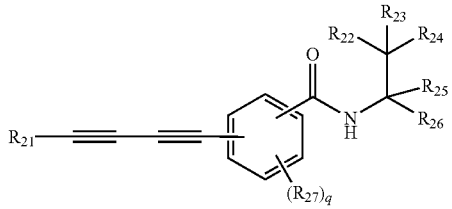

or a pharmaceutically acceptable salt thereof, wherein q is an integer 0, 1, 2, 3, or 4;

$R_{21}$ is $C_1$-$C_6$ alkyl, $C_1$-$C_6$ haloalkyl, —CO($C_1$-$C_6$ alkyl), —$C_1$-$C_6$ alkyl-CO($C_1$-$C_6$ alkyl), —$C_1$-$C_6$ alkyl-$CO_2$H, $C_3$-$C_8$ cycloalkyl optionally substituted with $R_{28}$, ($C_3$-$C_8$ cycloalkyl)$C_1$-$C_6$ alkyl- optionally substituted with $R_{28}$, aryl optionally substituted with $R_{28}$, (aryl)$C_1$-$C_6$ alkyl- optionally substituted with $R_{28}$, heteroaryl optionally substituted with $R_{28}$, (heteroaryl)$C_1$-$C_6$ alkyl- optionally substituted with $R_{28}$, heterocyclyl optionally substituted with $R_{28}$, or (heterocycloalkyl)$C_1$-$C_6$ alkyl- optionally substituted with $R_{28}$, $R_{22}$ is selected from the group consisting of hydrogen, halogen, $C_1$-$C_6$ alkyl, $C_1$-$C_6$ haloalkyl, —$NH_2$, —NH($C_1$-$C_6$ alkyl), —N($C_1$-$C_6$ alkyl)$_2$, —OH, $C_1$-$C_6$ alkoxy, $C_1$-$C_6$ haloalkoxy, —SH, —S($C_1$-$C_6$ alkyl), hydroxy($C_1$-$C_6$ alkyl), alkoxy($C_1$-$C_6$ alkyl), and amino($C_1$-$C_6$ alkyl);

$R_{23}$ is selected from the group consisting of hydrogen, halogen, $C_1$-$C_6$ alkyl, $C_1$-$C_6$ haloalkyl, —$NH_2$, —NH($C_1$-$C_6$ alkyl), —N($C_1$-$C_6$ alkyl)$_2$, —OH, $C_1$-$C_6$ alkoxy, $C_1$-$C_6$ haloalkoxy, —SH, —S($C_1$-$C_6$ alkyl), hydroxy($C_1$-$C_6$ alkyl), alkoxy($C_1$-$C_6$ alkyl), amino($C_1$-$C_6$ alkyl), —NHCO($C_1$-$C_6$ alkyl), —$NHCONH_2$, —NHCONH($C_1$-$C_6$ alkyl), —OCO($C_1$-$C_6$ alkyl), and —NHCO($C_1$-$C_6$ alkoxy);

$R_{24}$ is $C_1$-$C_6$ alkyl or $C_1$-$C_6$ haloalkyl;

$R_{25}$ is independently selected from the group consisting of halogen, —$NO_2$, —CN, $C_1$-$C_6$ alkyl, $C_1$-$C_6$ haloalkyl, —$NH_2$, —NH($C_1$-$C_6$ alkyl), —N($C_1$-$C_6$ alkyl)$_2$, —OH, $C_1$-$C_6$ alkoxy, $C_1$-$C_6$ haloalkoxy, —$CONH_2$, —CON($C_1$-$C_6$ alkyl), —CON($C_1$-$C_6$ alkyl)$_2$, —CONH—OH, —CONH—OCO($C_1$-$C_6$ alkyl), —CONH—$NH_2$, —$CO_2$H, and —$CO_2$($C_1$-$C_6$ alkyl);

$R_{26}$ is hydrogen or $C_1$-$C_6$ alkyl;

each $R_{27}$ is independently selected from the group consisting of halogen, —$NO_2$, —CN, $C_1$-$C_6$ alkyl, $C_1$-$C_6$ haloalkyl, —$NH_2$, —NH($C_1$-$C_6$ alkyl), —N($C_1$-$C_6$ alkyl)$_2$, —OH, $C_1$-$C_6$ alkoxy, and $C_1$-$C_6$ haloalkoxy; and each $R_{28}$ is independently selected from the group consisting of halogen, —$NO_2$, —CN, $C_1$-$C_6$ alkyl, $C_1$-$C_6$ haloalkyl, —$NH_2$, —NH($C_1$-$C_6$ alkyl), —N($C_1$-$C_6$ alkyl)$_2$, —OH, $C_1$-$C_6$ alkoxy, $C_1$-$C_6$ haloalkoxy, —$C_1$-$C_6$ alkyl-OH, —$C_1$-$C_6$ alkyl-($C_1$-$C_6$ alkoxy), —$C_1$-$C_6$ alkyl-$NH_2$, —$C_1$-$C_6$ alkyl-NH—$C_1$-$C_6$ alkyl), —$C_1$-$C_6$ alkyl-N($C_1$-$C_6$ alkyl)$_2$, —$C_1$-$C_6$ alkyl-NH($SO_2C_1$-$C_6$ alkyl), —$CONH_2$, —CON($C_1$-$C_6$ alkyl), —CON($C_1$-$C_6$ alkyl)$_2$, —NH($SO_2C_1$-$C_6$ alkyl), —CONH—OH, —CONH—OCO($C_1$-$C_6$ alkyl), —C(NH)NH—OH, —CONH—$NH_2$, —CO($C_1$-$C_6$ alkyl), —$CO_2$H, —$CO_2$($C_1$-$C_6$ alkyl), —$C_1$-$C_6$ alkyl-$CONH_2$, —$C_1$-$C_6$ alkyl-CON($C_1$-$C_6$ alkyl), —$C_1$-$C_6$ alkyl-CON($C_1$-$C_6$ alkyl)$_2$, —$C_1$-$C_6$ alkyl-CONH—OH, —$C_1$-$C_6$ alkyl-CO($C_1$-$C_6$ alkyl), —$C_1$-$C_6$ alkyl-$CO_2$H, and —$C_1$-$C_6$ alkyl-$CO_2$($C_1$-$C_6$ alkyl); or two $R_{28}$ groups when attached to the same carbon atom form =O;

the method comprising reacting haloethynyl compound of formula:

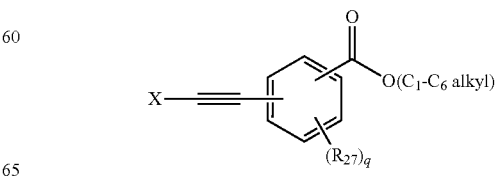

wherein X is halogen (e.g., Br, Cl, F, I), with

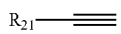

in the presence of transition metal catalyst and base.

BRIEF DESCRIPTION OF THE DRAWINGS

The accompanying drawings are included to provide a further understanding of the methods and devices of the disclosure, and are incorporated in and constitute a part of this specification. The drawings are not necessarily to scale, and sizes of various elements may be distorted for clarity. The drawings illustrate one or more embodiment(s) of the disclosure, and together with the description serve to explain the principles and operation of the disclosure.

DETAILED DESCRIPTION OF THE INVENTION

Figure 1:
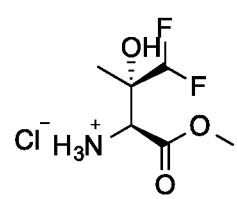
FIG. 1 is a X-ray crystallographic structure of methyl 2-amino-4,4-difluoro-3-hydroxy-3-methylbutanoate hydrochloride (compound 4) and (2S,3S)-methyl 2-amino-4,4-difluoro-3-hydroxy-3-methylbutanoate (−) CSA (compound 5).
Figure 1:
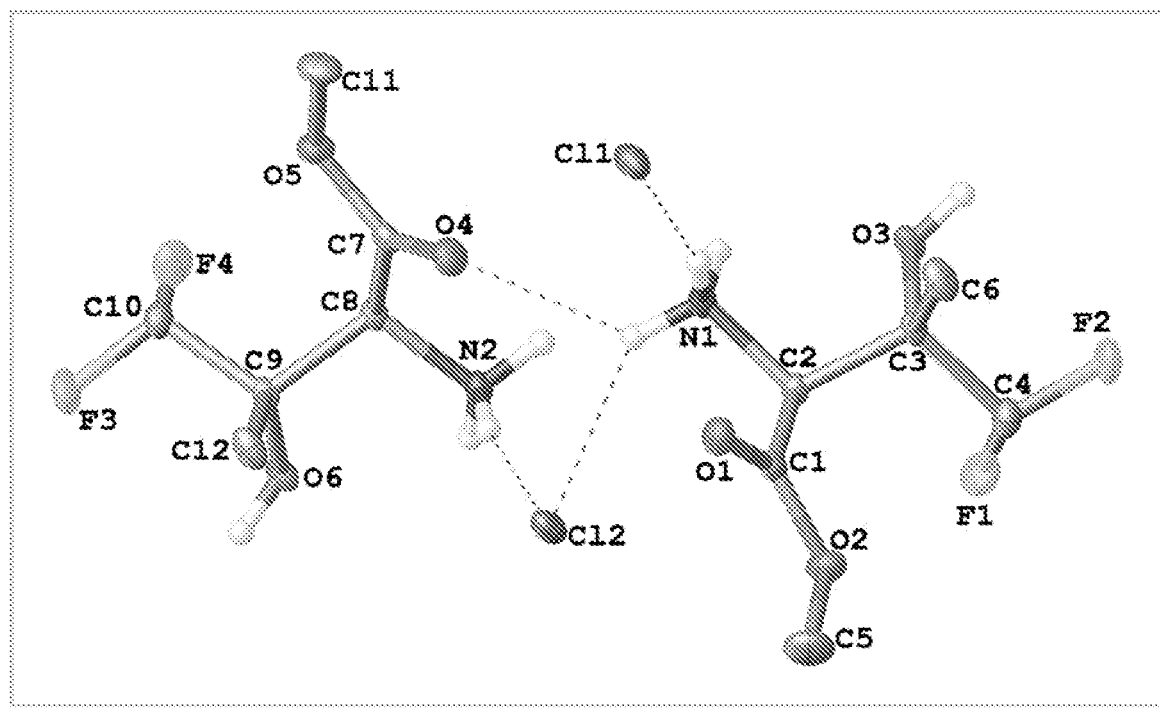

Before the disclosed processes and materials are described, it is to be understood that the aspects described herein are not limited to specific embodiments, apparati, or configurations, and as such can, of course, vary. It is also to be understood that the terminology used herein is for the purpose of describing particular aspects only and, unless specifically defined herein, is not intended to be limiting.

Throughout this specification, unless the context requires otherwise, the word "comprise" and "include" and variations (e.g., "comprises," "comprising," "includes," "including") will be understood to imply the inclusion of a stated component, feature, element, or step or group of components, features, elements or steps but not the exclusion of any other integer or step or group of integers or steps.

As used in the specification and the appended claims, the singular forms "a," "an" and "the" include plural referents unless the context clearly dictates otherwise.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

As used herein, the term "contacting" includes the physical contact of at least one substance to another substance.

All percentages, ratios and proportions herein are by weight, unless otherwise specified. A weight percent (weight %, also as wt %) of a component, unless specifically stated to the contrary, is based on the total weight of the formulation or composition in which the component is included (e.g., on the total amount of the catalyst material). All mol % values are based on the moles of metal atoms.

In one embodiment, the disclosure provides compounds of formula I wherein $R_4$ is $C_1$ haloalkyl (embodiment 2). Particular embodiments based on formula I include those of Embodiment 3, i.e., compounds of Embodiment 2 wherein $R_4$ is —$CH_2F$, —$CHF_2$, or —$CF_3$. Other embodiments are those where $R_4$ is —$CHF_2$. (Embodiment 4).

Another embodiment of the invention, i.e., Embodiment 5, encompasses compounds of any of embodiments 1-4 where $R_2$ is halogen, $C_1$-$C_6$ alkyl, or $C_1$-$C_6$ haloalkyl. Other embodiments are those where $R_2$ is halogen or $C_1$-$C_6$ alkyl (Embodiment 6). In still other embodiments based on embodiment 5, $R_2$ is $C_1$-$C_6$ alkyl (Embodiment 7). In still other embodiments based on embodiment 5, $R_2$ is methyl. (Embodiment 8). Other embodiments are those where $R_2$ is methyl, and $R_4$ is —$CHF_2$ (Embodiment 9).

Another embodiment of the invention, i.e., Embodiment 10, encompasses compounds of any of embodiments 1-9 where $R_3$ is selected from the group consisting of —$NH_2$, —$NH(C_1$-$C_6$ alkyl), —$N(C_1$-$C_6$ alkyl)$_2$, —OH, $C_1$-$C_6$ alkoxy, $C_1$-$C_6$ haloalkoxy, —SH, —$S(C_1$-$C_6$ alkyl), —$NHCO(C_1$-$C_6$ alkyl), —$NHCONH_2$, —$NHCONH(C_1$-$C_6$ alkyl), —$OCO(C_1$-$C_6$ alkyl), and —$NHCO(C_1$-$C_6$ alkoxy). Other embodiments are those where $R_3$ is selected from the group consisting of —$NH_2$, —$NH(C_1$-$C_6$ alkyl), —$N(C_1$-$C_6$ alkyl)$_2$, —$NHCO(C_1$-$C_6$ alkyl), —$NHCONH_2$, —$NHCONH(C_1$-$C_6$ alkyl), and —$NHCO(C_1$-$C_6$ alkoxy). (Embodiment 11). In still other embodiments based on embodiment 10, $R_3$ is —$NH_2$ (Embodiment 12). In still other embodiments based on embodiment 10, $R_3$ is —$NHCO(C_1$-$C_6$ alkyl), —$NHCONH_2$, —$NHCONH(C_1$-$C_6$ alkyl), or —$NHCO(C_1$-$C_6$ alkoxy). (Embodiment 13). Other embodiments are those where $R_3$ is —OH or $C_1$-$C_6$ alkoxy (Embodiment 14). In still other embodiments based on embodiment 10, $R_3$ is —OH (Embodiment 15).

Particular embodiments based on formula I include those of Embodiment 16, i.e., compounds of formula I-A:

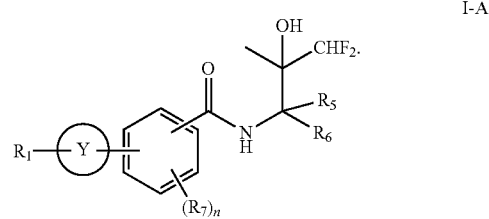

I-A

Another embodiment of the invention, i.e., Embodiment 17, encompasses compounds of any of embodiments 1-16 where Y is aryl optionally substituted with $R_8$ or heteroaryl optionally substituted with $R_8$; or Y is aryl optionally substituted with $R_8$; or Y is phenyl optionally substituted with $R_8$. Other embodiments are those where each $R_8$ is independently selected from the group consisting of halogen, $C_1$-$C_6$ alkyl, $C_1$-$C_6$ haloalkyl, —$NH_2$, —$NH(C_1$-$C_6$ alkyl), —N(C$_1$-C$_6$ alkyl)$_2$, —OH, C$_1$-C$_6$ alkoxy, and C$_1$-C$_6$ haloalkoxy. (Embodiment 18). In still other embodiments based on Embodiment 17, each R$_8$ is independently selected from the group consisting of halogen, C$_1$-C$_6$ alkyl, C$_1$-C$_6$ haloalkyl, —OH, C$_1$-C$_6$ alkoxy, C$_1$-C$_6$ haloalkoxy, —CONH—OH, —CONH—OCO(C$_1$-C$_6$ alkyl), and —C(NH)NH—OH. (Embodiment 19). Other embodiments are wherein each R$_8$ is independently selected from the group consisting of halogen, C$_1$-C$_6$ alkyl, C$_1$-C$_6$ haloalkyl, —CONH—OH, and —C(NH)NH—OH. (Embodiment 20). Other embodiments are wherein R$_8$ is halogen or —C(NH)NH—OH; or R$_8$ is halogen; or R$_8$ is —C(NH)NH—OH. (Embodiments 21). Embodiment of the invention, i.e., Embodiment 22, encompasses compounds of any of embodiments 1-16 where Y is unsubstituted phenyl.

Another embodiment of the invention, i.e., Embodiment 23, encompasses compounds of any of embodiments 1-22 where R$_1$ is hydrogen.

Another embodiment of the invention, i.e., Embodiment 24, encompasses compounds of any of embodiments 1-23 where n is 0, 1, or 2; or n is 0 or 1; or n is 0; or n is 1.

Another embodiment of the invention, i.e., Embodiment 25, encompasses compounds of any of embodiments 1-24 where each R$_7$ is independently selected from the group consisting of halogen, C$_1$-C$_6$ alkyl, C$_1$-C$_6$ haloalkyl, —NH$_2$, —NH(C$_1$-C$_6$ alkyl), —N(C$_1$-C$_6$ alkyl)$_2$, —OH, C$_1$-C$_6$ alkoxy, and C$_1$-C$_6$ haloalkoxy. Other embodiments are wherein each R$_7$ is independently selected from the group consisting of halogen, C$_1$-C$_6$ alkyl, C$_1$-C$_6$ haloalkyl, —OH, C$_1$-C$_6$ alkoxy, and C$_1$-C$_6$ haloalkoxy. (Embodiment 26). In still other embodiments, each R$_7$ is independently selected from the group consisting of halogen, C$_1$-C$_6$ alkyl, and C$_1$-C$_6$ haloalkyl. (Embodiment 27). Other embodiments are those where R$_7$ is halogen. (Embodiment 28).

One embodiment of the invention, i.e., Embodiment 29, encompasses compounds of any of embodiments 1-28 where R$_6$ is methyl. Another embodiment of the invention, i.e., Embodiment 30, encompasses compounds of any of embodiments 1-28 where R$_6$ is hydrogen.

One embodiment of the invention, i.e., Embodiment 31, encompasses compounds of any of embodiments 1-30 where R$_5$—CONH—OH, —CONH—NH$_2$, or —CONH—OCO (C$_1$-C$_6$ alkyl). Another embodiment of the invention, i.e., Embodiment 32, encompasses compounds of any of embodiments 1-30 where R$_5$—CONH—OH, or —CONH—OCO(C$_1$-C$_6$ alkyl).

Particular compounds of formula I include:

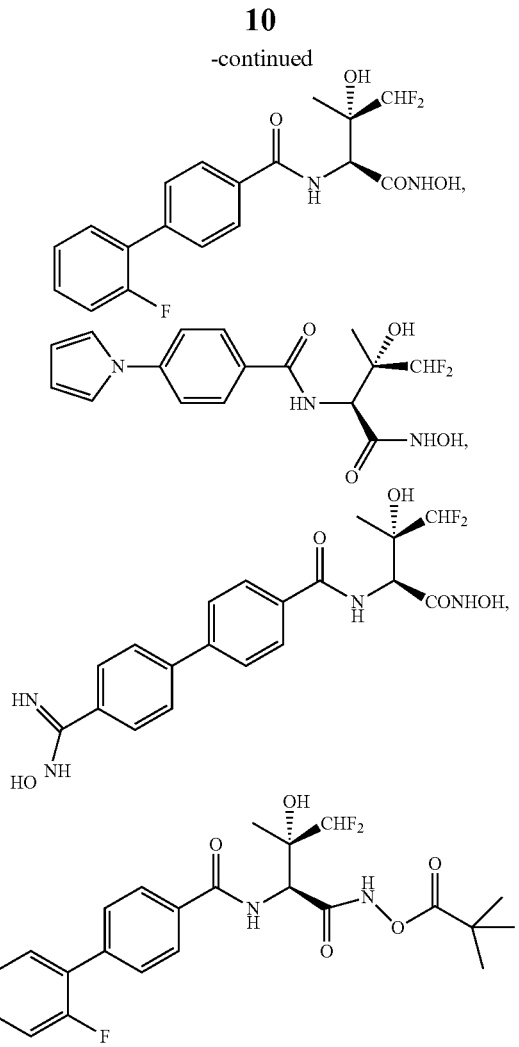

or a pharmaceutically acceptable salt thereof. (Embodiment 33).

In one embodiment, the disclosure provides compounds of formula II wherein R$_{14}$ is C$_1$ haloalkyl (embodiment 35). Particular embodiments based on formula II include those of Embodiment 36, wherein R$_{14}$ is —CH$_2$F, —CHF$_2$, or —CF$_3$. Other embodiments are those where R$_{14}$ is —CHF$_2$. (Embodiment 37).

Another embodiment of the invention, i.e., Embodiment 38, encompasses compounds of any of embodiments 34-37 where R$_{12}$ is halogen, C$_1$-C$_6$ alkyl, or C$_1$-C$_6$ haloalkyl. Other embodiments are those where R$_{12}$ is halogen or C$_1$-C$_6$ alkyl (Embodiment 39). In still other embodiments based on embodiment 38, R$_{12}$ is C$_1$-C$_6$ alkyl (Embodiment 40). In still other embodiments based on embodiment 38, R$_{12}$ is methyl. (Embodiment 41). Other embodiments are those where R$_{12}$ is methyl, and R$_{14}$ is —CHF$_2$ (Embodiment 42).

One embodiment of the invention, i.e., Embodiment 43, encompasses compounds of any of embodiments 34-42 where R$_{13}$ is selected from the group consisting of —NH$_2$, —NH(C$_1$-C$_6$ alkyl), —N(C$_1$-C$_6$ alkyl)$_2$, —OH, C$_1$-C$_6$ alkoxy, C$_1$-C$_6$ haloalkoxy, —SH, —S(C$_1$-C$_6$ alkyl), —NHCO(C$_1$-C$_6$ alkyl), —NHCONH$_2$, —NHCONH(C$_1$-C$_6$ alkyl), —OCO(C$_1$-C$_6$ alkyl), and —NHCO(C$_1$-C$_6$ alkoxy). Other embodiments are those where R$_{13}$ is selected from the group consisting of —NH$_2$, —NH(C$_1$-C$_6$ alkyl), —N(C$_1$-C$_6$ alkyl)$_2$, —NHCO(C$_1$-C$_6$ alkyl), —NHCONH$_2$, —NHCONH($C_1$-$C_6$ alkyl), and —NHCO($C_1$-$C_6$ alkoxy). (Embodiment 44). In still other embodiments based on embodiment 43, $R_{13}$ is —$NH_2$. (Embodiment 45). Other embodiments are where $R_{13}$ is —NHCO($C_1$-$C_6$ alkyl), —$NHCONH_2$, —NHCONH($C_1$-$C_6$ alkyl), or —NHCO($C_1$-$C_6$ alkoxy). (Embodiment 46). Other embodiments are those where $R_{13}$ is —OH or $C_1$-$C_6$ alkoxy. (Embodiment 47). In still other embodiments, based on embodiment 43, $R_{13}$ is —OH. (Embodiment 48).

One embodiment of the invention, i.e., Embodiment 49, encompasses compounds of any of embodiments 34-42 where the compound is of formula II-A:

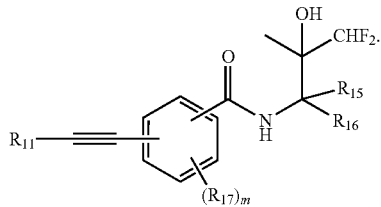

One embodiment of the invention, i.e., Embodiment 50, encompasses compounds of any of embodiments 34-49 wherein m is 0, 1, or 2; or m is 0 or 1; or m is 0; or m is 1.

Another embodiment of the invention, i.e., Embodiment 51, encompasses compounds of any of embodiments 34-50 where each $R_{17}$ is independently selected from the group consisting of halogen, $C_1$-$C_6$ alkyl, $C_1$-$C_6$ haloalkyl, —$NH_2$, —NH($C_1$-$C_6$ alkyl), —N($C_1$-$C_6$ alkyl)$_2$, —OH, $C_1$-$C_6$ alkoxy, and $C_1$-$C_6$ haloalkoxy. Other embodiments are those where each $R_{17}$ is independently selected from the group consisting of halogen, $C_1$-$C_6$ alkyl, $C_1$-$C_6$ haloalkyl, —OH, $C_1$-$C_6$ alkoxy, and $C_1$-$C_6$ haloalkoxy. (Embodiment 52). Yet other embodiments are those where each $R_{17}$ is independently selected from the group consisting of halogen, $C_1$-$C_6$ alkyl, and $C_1$-$C_6$ haloalkyl. (Embodiment 53). In still other embodiments based on embodiment 51, $R_{17}$ is halogen. (Embodiment 54).

One embodiment of the invention, i.e., Embodiment 55, encompasses compounds of any of embodiments 34-54 where $R_{16}$ is methyl.

Another embodiment of the invention, i.e., Embodiment 56, encompasses compounds of any of embodiments 34-55 where $R_{16}$ is hydrogen.

Other embodiment of the invention, i.e., Embodiment 57, encompasses compounds of any of embodiments 34-56 where $R_{15}$—CONH—OH, —CONH—$NH_2$, or —CONH—OCO($C_1$-$C_6$ alkyl). Other embodiments are those where $R_{15}$—CONH—OH, or —CONH—OCO($C_1$-$C_6$ alkyl). (Embodiment 58).

Other embodiment of the invention, i.e., Embodiment 59, encompasses compounds of any of embodiments 34-58 where $R_{11}$ is —C≡C—$R_{10}$, which is of formula II-B:

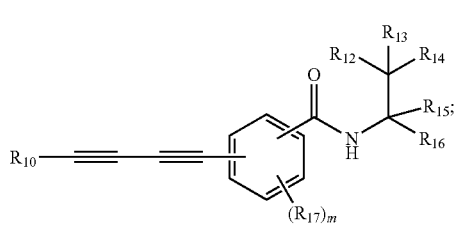

or wherein $R_{11}$ is of formula:

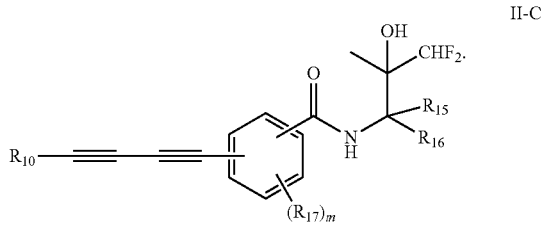

Particular embodiments based on formula II and Embodiment 59 include those of Embodiment 60 wherein $R_{10}$ is —CO($C_1$-$C_6$ alkyl), —$C_1$-$C_6$ alkyl-CO($C_1$-$C_6$ alkyl), —$C_1$-$C_6$ alkyl-$CO_2$H, $C_3$-$C_8$ cycloalkyl optionally substituted with $R_{19}$, or ($C_3$-$C_8$ cycloalkyl)$C_1$-$C_6$ alkyl-optionally substituted with $R_{19}$. Other embodiments are those where $R_{10}$ is $C_3$-$C_8$ cycloalkyl optionally substituted with $R_{19}$ or ($C_3$-$C_8$ cycloalkyl)$C_1$-$C_6$ alkyl- optionally substituted with $R_{19}$. (Embodiment 61.) Other embodiments are those where $R_{10}$ is $C_3$-$C_8$ cycloalkyl optionally substituted with $R_{19}$. (Embodiment 62). Yet other embodiment are those where $R_{10}$ is $C_3$-$C_6$ cycloalkyl optionally substituted with $R_{19}$. (Embodiment 63).

Another embodiment of the invention, i.e., Embodiment 64, encompasses compounds of any of embodiments 60-63 where $R_{10}$ is cyclopropyl, cyclopentyl, or cyclohexyl, each optionally substituted with $R_{19}$.

Another embodiment of the invention, i.e., Embodiment 65, encompasses compounds of any of embodiments 60-64 where each $R_{19}$ is independently selected from the group consisting of halogen, $C_1$-$C_6$ alkyl, $C_1$-$C_6$ haloalkyl, —$NH_2$, —NH($C_1$-$C_6$ alkyl), —N($C_1$-$C_6$ alkyl)$_2$, —OH, $C_1$-$C_6$ alkoxy, $C_1$-$C_6$ haloalkoxy, —$C_1$-$C_6$ alkyl-OH, —$C_1$-$C_6$ alkyl-($C_1$-$C_6$ alkoxy), —$C_1$-$C_6$ alkyl-$NH_2$, —$C_1$-$C_6$ alkyl-NH—$C_1$-$C_6$ alkyl), —$C_1$-$C_6$ alkyl-N($C_1$-$C_6$ alkyl)$_2$, —$C_1$-$C_6$ alkyl-NH($SO_2C_1$-$C_6$ alkyl), —$CONH_2$, —CON($C_1$-$C_6$ alkyl), —CON($C_1$-$C_6$ alkyl)$_2$, —CO($C_1$-$C_6$ alkyl), —$CO_2$H, —$CO_2$($C_1$-$C_6$ alkyl), —$C_1$-$C_6$ alkyl-$CONH_2$, —$C_1$-$C_6$ alkyl-CON($C_1$-$C_6$ alkyl), —$C_1$-$C_6$ alkyl-CON($C_1$-$C_6$ alkyl)$_2$, —$C_1$-$C_6$ alkyl-CO($C_1$-$C_6$ alkyl), —$C_1$-$C_6$ alkyl-$CO_2$H, and —$C_1$-$C_6$ alkyl-$CO_2$($C_1$-$C_6$ alkyl). Another embodiment of the invention, i.e., Embodiment 66, encompasses compounds of any of embodiments 60-64 where each $R_{19}$ is independently selected from the group consisting of —$NH_2$, —NH($C_1$-$C_6$ alkyl), —N($C_1$-$C_6$ alkyl)$_2$, —OH, $C_1$-$C_6$ alkoxy, —$C_1$-$C_6$ alkyl-OH, —$C_1$-$C_6$ alkyl-($C_1$-$C_6$ alkoxy), —$C_1$-$C_6$ alkyl-$NH_2$, —$C_1$-$C_6$ alkyl-NH—$C_1$-$C_6$ alkyl), —$C_1$-$C_6$ alkyl-N($C_1$-$C_6$ alkyl)$_2$, —$C_1$-$C_6$ alkyl-NH($SO_2C_1$-$C_6$ alkyl), —$CONH_2$, —CON($C_1$-$C_6$ alkyl), —CON($C_1$-$C_6$ alkyl)$_2$, —CO($C_1$-$C_6$ alkyl), —$CO_2$H, —$CO_2$($C_1$-$C_6$ alkyl), —$C_1$-$C_6$ alkyl-$CONH_2$, —$C_1$-$C_6$ alkyl-CON($C_1$-$C_6$ alkyl), —$C_1$-$C_6$ alkyl-CON($C_1$-$C_6$ alkyl)$_2$, —$C_1$-$C_6$ alkyl-CO($C_1$-$C_6$ alkyl), —$C_1$-$C_6$ alkyl-$CO_2$H, and —$C_1$-$C_6$ alkyl-$CO_2$($C_1$-$C_6$ alkyl). Another embodiment of the invention, i.e., Embodiment 67, encompasses compounds of any of embodiments 60-64 where each $R_{19}$ is independently selected from the group consisting of —$NH_2$, —NH($C_1$-$C_6$ alkyl), —OH, $C_1$-$C_6$ alkoxy, —$C_1$-$C_6$ alkyl-OH, —$C_1$-$C_6$ alkyl-($C_1$-$C_6$ alkoxy), —$C_1$-$C_6$ alkyl-$NH_2$, —$C_1$-$C_6$ alkyl-NH—$C_1$-$C_6$ alkyl), —$C_1$-$C_6$ alkyl-NH($SO_2C_1$-$C_6$ alkyl), —$CONH_2$, —CON($C_1$-$C_6$ alkyl), —CO($C_1$-$C_6$ alkyl), —$CO_2$H, —$CO_2$($C_1$-$C_6$ alkyl), —$C_1$-$C_6$ alkyl-$CONH_2$, —$C_1$-$C_6$ alkyl-CON($C_1$-$C_6$ alkyl), —$C_1$-$C_6$ alkyl-CO($C_1$-$C_6$ alkyl), and —$C_1$-$C_6$ alkyl-$CO_2$H. Another embodiment of the invention, i.e., Embodiment 68, encompasses compounds of any of embodiments 60-64 where each $R_{19}$ is independently selected from the group consisting of —$C_1$-$C_6$ alkyl-OH, —$C_1$-$C_6$ alkyl-($C_1$-$C_6$ alkoxy), —$C_1$-$C_6$ alkyl-$NH_2$, —$C_1$-$C_6$ alkyl-NH—$C_1$-$C_6$ alkyl), —$C_1$-$C_6$ alkyl-NH ($SO_2C_1$-$C_6$ alkyl), —$CONH_2$, —CO($C_1$-$C_6$ alkyl), —$C_1$-$C_6$ alkyl-$CONH_2$, —$C_1$-$C_6$ alkyl-CO($C_1$-$C_6$ alkyl), and —$C_1$-$C_6$ alkyl-$CO_2H$.

One embodiment of the invention, i.e., Embodiment 69, encompasses compounds of embodiment 59 where $R_{10}$ is unsubstituted $C_3$-$C_8$ cycloalkyl; or $R_{10}$ is unsubstituted $C_3$-$C_6$ cycloalkyl; or $R_{10}$ is cyclopropyl, cyclopentyl, or cyclohexyl.

Another embodiment of the invention, i.e., Embodiment 70, encompasses compounds of embodiment 59 where $R_{10}$ is ($C_3$-$C_8$ cycloalkyl)$C_1$-$C_6$ alkyl- optionally substituted with $R_{19}$.

In Embodiment 71, which is based on formula II, the compounds of embodiment 70 are those wherein $R_{10}$ is ($C_3$-$C_6$ cycloalkyl)$CH_2$— optionally substituted with $R_{19}$; or $R_{10}$ is unsubstituted ($C_3$-$C_6$ cycloalkyl)$CH_2$—. In Embodiment 72, which is based on formula II, the compounds of embodiment 70 are those wherein $R_{10}$ is cyclopropyl-$CH_2$—, cyclopentyl- $CH_2$—, or cyclohexyl-$CH_2$—, each optionally substituted with $R_{19}$; or $R_{10}$ is cyclopropyl-$CH_2$—, cyclopentyl- $CH_2$—, or cyclohexyl-$CH_2$—; or $R_{10}$ is cyclohexyl-$CH_2$— optionally substituted with $R_{19}$; or $R_{10}$ is unsubstituted cyclohexyl-$CH_2$—.

In Embodiment 73, which is based on formula II, the compounds of embodiments 70-72 are those wherein each $R_{19}$ is independently selected from the group consisting of —$C_1$-$C_6$ alkyl-OH, —$C_1$-$C_6$ alkyl-($C_1$-$C_6$ alkoxy), —$C_1$-$C_6$ alkyl-$NH_2$, —$C_1$-$C_6$ alkyl-NH—$C_1$-$C_6$ alkyl), —$C_1$-$C_6$ alkyl-NH($SO_2C_1$-$C_6$ alkyl), —$CONH_2$, —CO($C_1$-$C_6$ alkyl), —$C_1$-$C_6$ alkyl-$CONH_2$, —$C_1$-$C_6$ alkyl-CO($C_1$-$C_6$ alkyl), and —$C_1$-$C_6$ alkyl-$CO_2H$.

Another embodiment of the invention, i.e., Embodiment 74, encompasses compounds of embodiment 59 where $R_{10}$ is $C_1$-$C_6$ alkyl, $C_1$-$C_6$ haloalkyl, —CO($C_1$-$C_6$ alkyl), —$C_1$-$C_6$ alkyl-CO($C_1$-$C_6$ alkyl), or —$C_1$-$C_6$ alkyl-$CO_2H$. Another embodiment of the invention, i.e., Embodiment 75, encompasses compounds of embodiment 59 where $R_{10}$ is —CO($C_1$-$C_6$ alkyl), —$C_1$-$C_6$ alkyl-CO($C_1$-$C_6$ alkyl), or —$C_1$-$C_6$ alkyl-$CO_2H$. Other embodiments are those where $R_{10}$ is —$COCH_3$, —$CH_2CH_2$—$COCH_3$, or —$CH_2CH_2$—$CO_2H$. (Embodiment 76). Other embodiments are those where $R_{10}$ is heterocyclyl optionally substituted with $R_{19}$. (Embodiment 77). In Embodiment 78, which is based on formula II, the compounds of embodiment 77 are those wherein the heterocyclyl is selected from the group consisting of aziridinyl, azetidinyl, pyrrolidinyl, piperidinyl, piperazinyl, morpholinyl, homopiperazinyl, homopiperdinyl, diazepanyl, imidazolidinyl, tetrahydro-2H-pyran-4-yl, 2,3-dihydro-1H-imidazol-4-yl, 1,4,5,6-tetrahydropyrazin-2-yl, 2,3,4,7-tetrahydro-1H-1,4-diazepin-1-yl, 1,4,5,6-tetrahydropyridin-3-yl, 4,5-dihydro-1H-pyrrol-3-yl, and 3,4-dihydro-2H-1,4-oxazin-6-yl. In Embodiment 79, which is based on formula II, the compounds of embodiment 77 are those wherein the heterocyclyl is selected from the group consisting of aziridinyl or tetrahydro-2H-pyran-4-yl.

One embodiment of the invention, i.e., Embodiment 80, encompasses compounds of any of embodiments 34-58 where $R_{11}$ is $C_1$-$C_6$ alkyl, $C_1$-$C_6$ haloalkyl, —CO($C_1$-$C_6$ alkyl), —$C_1$-$C_6$ alkyl-CO($C_1$-$C_6$ alkyl), —$C_1$-$C_6$ alkyl-$CO_2H$, $C_3$-$C_8$ cycloalkyl optionally substituted with $R_{18}$, or heterocyclyl optionally substituted with $R_{18}$.

Another embodiment of the invention, i.e., Embodiment 81, encompasses compounds of any of embodiments 34-58 and 80 where $R_{11}$ is —CO($C_1$-$C_6$ alkyl), —$C_1$-$C_6$ alkyl-CO ($C_1$-$C_6$ alkyl), —$C_1$-$C_6$ alkyl-$CO_2H$, $C_3$-$C_8$ cycloalkyl optionally substituted with $R_{18}$, or ($C_3$-$C_8$ cycloalkyl)$C_1$-$C_6$ alkyl- optionally substituted with $R_{18}$. Another embodiment of the invention, i.e., Embodiment 82, encompasses compounds of any of embodiments 34-58 and 80 where $R_{11}$ is $C_3$-$C_8$ cycloalkyl optionally substituted with $R_{18}$ or ($C_3$-$C_8$ cycloalkyl)$C_1$-$C_6$ alkyl-optionally substituted with $R_{18}$. Another embodiment of the invention, i.e., Embodiment 83, encompasses compounds of any of embodiments 34-58 and 80 where $R_{11}$ is $C_3$-$C_8$ cycloalkyl optionally substituted with $R_{18}$. Another embodiment of the invention, i.e., Embodiment 84, encompasses compounds of any of embodiments 34-58 and 80 where $R_{11}$ is $C_3$-$C_6$ cycloalkyl optionally substituted with $R_{18}$.

Particular embodiments based on formula II include those of Embodiment 85, i.e., compounds of Embodiment 81-84 wherein $R_{11}$ is cyclopropyl, cyclopentyl, or cyclohexyl, each optionally substituted with $R_{18}$. In Embodiment 86, the compounds of any one of embodiments 81-84 are wherein each $R_{18}$ is independently selected from the group consisting of halogen, $C_1$-$C_6$ alkyl, $C_1$-$C_6$ haloalkyl, —$NH_2$, —NH($C_1$-$C_6$ alkyl), —N($C_1$-$C_6$ alkyl)$_2$, —OH, $C_1$-$C_6$ alkoxy, $C_1$-$C_6$ haloalkoxy, —$C_1$-$C_6$ alkyl-OH, —$C_1$-$C_6$ alkyl-($C_1$-$C_6$ alkoxy), —$C_1$-$C_6$ alkyl-$NH_2$, —$C_1$-$C_6$ alkyl-NH—$C_1$-$C_6$ alkyl), —$C_1$-$C_6$ alkyl-N($C_1$-$C_6$ alkyl)$_2$, —$C_1$-$C_6$ alkyl-NH ($SO_2C_1$-$C_6$ alkyl), —$CONH_2$, —CON($C_1$-$C_6$ alkyl), —CON ($C_1$-$C_6$ alkyl)$_2$, —CO($C_1$-$C_6$ alkyl), —$CO_2H$, —$CO_2$($C_1$-$C_6$ alkyl), —$C_1$-$C_6$ alkyl-$CONH_2$, —$C_1$-$C_6$ alkyl-CON($C_1$-$C_6$ alkyl), —$C_1$-$C_6$ alkyl-CON($C_1$-$C_6$ alkyl)$_2$, —$C_1$-$C_6$ alkyl-CO($C_1$-$C_6$ alkyl), —$C_1$-$C_6$ alkyl-$CO_2H$, and —$C_1$-$C_6$ alkyl-$CO_2$($C_1$-$C_6$ alkyl). In Embodiment 87, the compounds of any of embodiments 81-84 are wherein each $R_{18}$ is independently selected from the group consisting of —$NH_2$, —NH($C_1$-$C_6$ alkyl), —N($C_1$-$C_6$ alkyl)$_2$, —OH, $C_1$-$C_6$ alkoxy, —$C_1$-$C_6$ alkyl-OH, —$C_1$-$C_6$ alkyl-($C_1$-$C_6$ alkoxy), —$C_1$-$C_6$ alkyl-$NH_2$, —$C_1$-$C_6$ alkyl-NH—$C_1$-$C_6$ alkyl), —$C_1$-$C_6$ alkyl-N($C_1$-$C_6$ alkyl)$_2$, —$C_1$-$C_6$ alkyl-NH($SO_2C_1$-$C_6$ alkyl), —$CONH_2$, —CON($C_1$-$C_6$ alkyl), —CON($C_1$-$C_6$ alkyl)$_2$, —CO($C_1$-$C_6$ alkyl), —$CO_2H$, —$CO_2$($C_1$-$C_6$ alkyl), —$C_1$-$C_6$ alkyl-$CONH_2$, —$C_1$-$C_6$ alkyl-CON($C_1$-$C_6$ alkyl), —$C_1$-$C_6$ alkyl-CON($C_1$-$C_6$ alkyl)$_2$, —$C_1$-$C_6$ alkyl-CO($C_1$-$C_6$ alkyl), —$C_1$-$C_6$ alkyl-$CO_2H$, and —$C_1$-$C_6$ alkyl-$CO_2$($C_1$-$C_6$ alkyl). In Embodiment 88, the compounds of any of embodiments 81-84 are wherein each $R_{18}$ is independently selected from the group consisting of —$NH_2$, —NH($C_1$-$C_6$ alkyl), —OH, $C_1$-$C_6$ alkoxy, —$C_1$-$C_6$ alkyl-OH, —$C_1$-$C_6$ alkyl-($C_1$-$C_6$ alkoxy), —$C_1$-$C_6$ alkyl-$NH_2$, —$C_1$-$C_6$ alkyl-NH—$C_1$-$C_6$ alkyl), —$C_1$-$C_6$ alkyl-NH($SO_201$-$C_6$ alkyl), —$CONH_2$, —CON($C_1$-$C_6$ alkyl), —CO($C_1$-$C_6$ alkyl), —$CO_2H$, —$CO_2$($C_1$-$C_6$ alkyl), —$C_1$-$C_6$ alkyl-$CONH_2$, —$C_1$-$C_6$ alkyl-CON($C_1$-$C_6$ alkyl), —$C_1$-$C_6$ alkyl-CO($C_1$-$C_6$ alkyl), and —$C_1$-$C_6$ alkyl-$CO_2H$. In Embodiment 89, the compounds of any of embodiments 81-84 are wherein each $R_{18}$ is independently selected from the group consisting of —$C_1$-$C_6$ alkyl-OH, —$C_1$-$C_6$ alkyl-($C_1$-$C_6$ alkoxy), —$C_1$-$C_6$ alkyl-$NH_2$, —$C_1$-$C_6$ alkyl-NH—$C_1$-$C_6$ alkyl), —$C_1$-$C_6$ alkyl-NH($SO_2C_1$-$C_6$ alkyl), —$CONH_2$, —CO($C_1$-$C_6$ alkyl), —$C_1$-$C_6$ alkyl-$CONH_2$, —$C_1$-$C_6$ alkyl-CO($C_1$-$C_6$ alkyl), and —$C_1$-$C_6$ alkyl-$CO_2H$.

One embodiment of the invention, i.e., Embodiment 90, encompasses compounds of any of embodiments 34-58 and 80 where $R_{11}$ is unsubstituted $C_3$-$C_8$ cycloalkyl; or $R_{11}$ is unsubstituted $C_3$-$C_6$ cycloalkyl; or $R_{11}$ is cyclopropyl, cyclopentyl, or cyclohexyl. Another embodiment of the invention, i.e., Embodiment 91, encompasses compounds of any of embodiments 34-58 and 80 where $R_{11}$ is ($C_3$-$C_8$ cycloalkyl) $C_1$-$C_6$ alkyl- optionally substituted with $R_{18}$. Another embodiment of the invention, i.e., Embodiment 92, encompasses compounds of any of embodiments 34-58 and 80 where $R_{11}$ is ($C_3$-$C_6$ cycloalkyl)$CH_2$-optionally substituted with $R_{18}$; or $R_{11}$ is unsubstituted ($C_3$-$C_6$ cycloalkyl)$CH_2$—; or $R_{11}$ is cyclopropyl-$CH_2$—, cyclopentyl- $CH_2$—, or cyclohexyl-$CH_2$—, each optionally substituted with $R_{18}$; or $R_{11}$ is cyclopropyl-$CH_2$—, cyclopentyl- $CH_2$—, or cyclohexyl-$CH_2$—; or $R_{11}$ is cyclohexyl-$CH_2$-optionally substituted with $R_{18}$; or $R_{11}$ is unsubstituted cyclohexyl-$CH_2$—. Particular embodiments based on any one of Embodiments 90-92 include those of Embodiment 93 wherein each $R_{19}$ is independently selected from the group consisting of —$C_1$-$C_6$ alkyl-OH, —$C_1$-$C_6$ alkyl-($C_1$-$C_6$ alkoxy), —$C_1$-$C_6$ alkyl-$NH_2$, —$C_1$-$C_6$ alkyl-NH—$C_1$-$C_6$ alkyl), —$C_1$-$C_6$ alkyl-NH ($SO_2C_1$-$C_6$ alkyl), —$CONH_2$, —$CO(C_1$-$C_6$ alkyl), —$C_1$-$C_6$ alkyl-$CONH_2$, —$C_1$-$C_6$ alkyl-CO($C_1$-$C_6$ alkyl), and —$C_1$-$C_6$ alkyl-$CO_2H$.

One embodiment of the invention, i.e., Embodiment 94, encompasses compounds of any of embodiments 34-58 and 80 where $R_{11}$ is $C_1$-$C_6$ alkyl, $C_1$-$C_6$ haloalkyl, —CO($C_1$-$C_6$ alkyl), —$C_1$-$C_6$ alkyl-CO($C_1$-$C_6$ alkyl), or —$C_1$-$C_6$ alkyl-$CO_2H$. Another embodiment of the invention, i.e., Embodiment 95, encompasses compounds of any of embodiments 34-58 and 80 where $R_{11}$ is —CO($C_1$-$C_6$ alkyl), —$C_1$-$C_6$ alkyl-CO($C_1$-$C_6$ alkyl), or —$C_1$-$C_6$ alkyl-$CO_2H$. One embodiment of the invention, i.e., Embodiment 96, encompasses compounds of any of embodiments 34-58 and 80 where $R_{11}$ is —$COCH_3$, —$CH_2CH_2$—$COCH_3$, or —$CH_2CH_2$—$CO_2H$.

Another embodiment of the invention, i.e., Embodiment 97, encompasses compounds of any of embodiments 34-58 and 80 where $R_{11}$ is heterocyclyl optionally substituted with $R_{18}$. In Embodiment 98, the heterocyclyl is selected from the group consisting of aziridinyl, azetidinyl, pyrrolidinyl, piperidinyl, piperazinyl, morpholinyl, homopiperazinyl, homopiperdinyl, diazepanyl, imidazolidinyl, tetrahydro-2H-pyran-4-yl, 2,3-dihydro-1H-imidazol-4-yl, 1,4,5,6-tetrahydropyrazin-2-yl, 2,3,4,7-tetrahydro-1H-1,4-diazepin-1-yl, 1,4,5,6-tetrahydropyridin-3-yl, 4,5-dihydro-1H-pyrrol-3-yl, and 3,4-dihydro-2H-1,4-oxazin-6-yl. In Embodiment 99, the heterocyclyl is selected from the group consisting of aziridinyl or tetrahydro-2H-pyran-4-yl.

Particular compounds of formula II include:

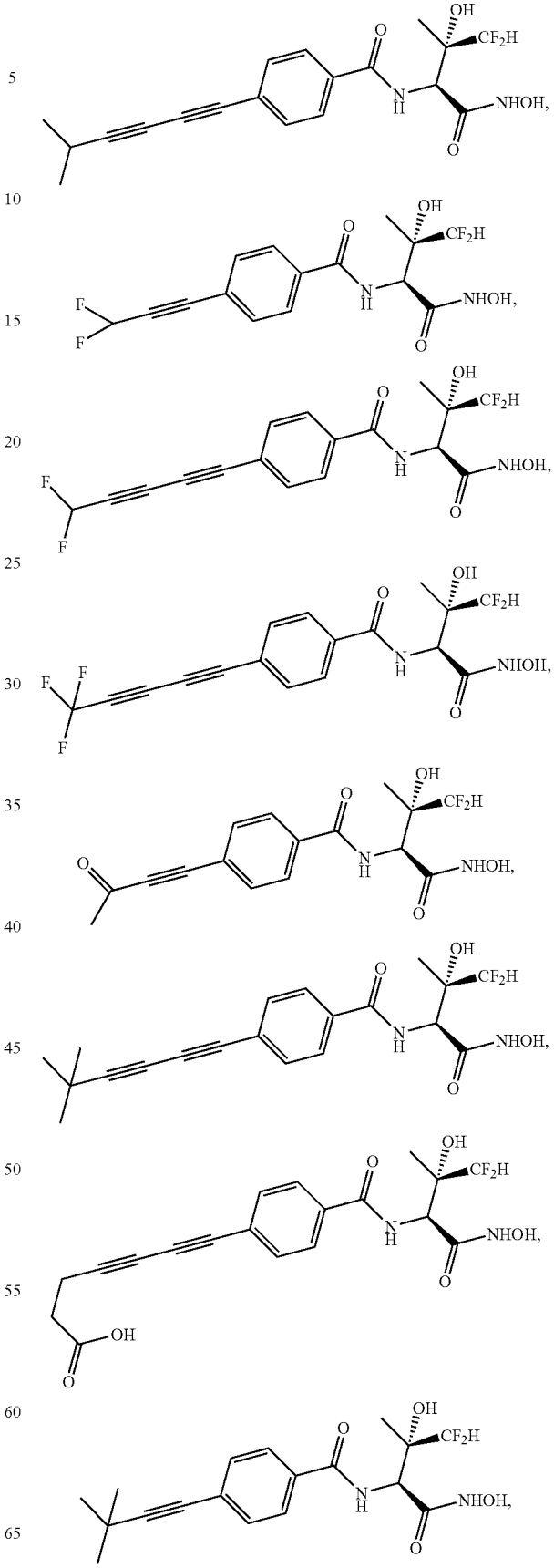

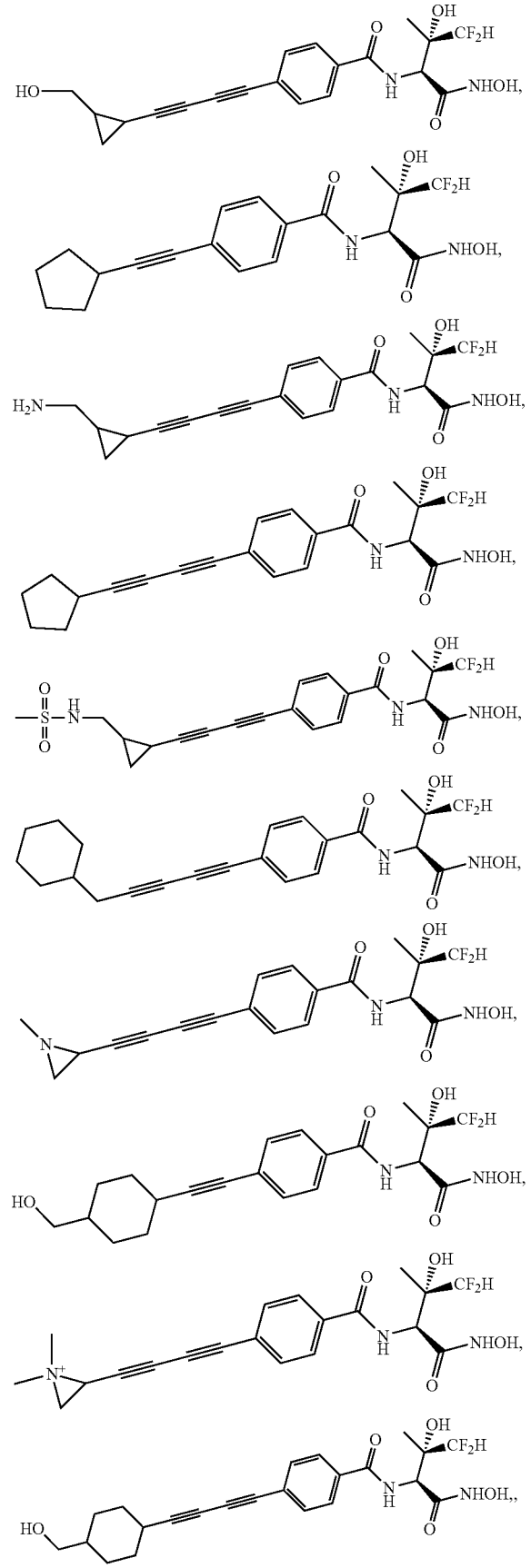
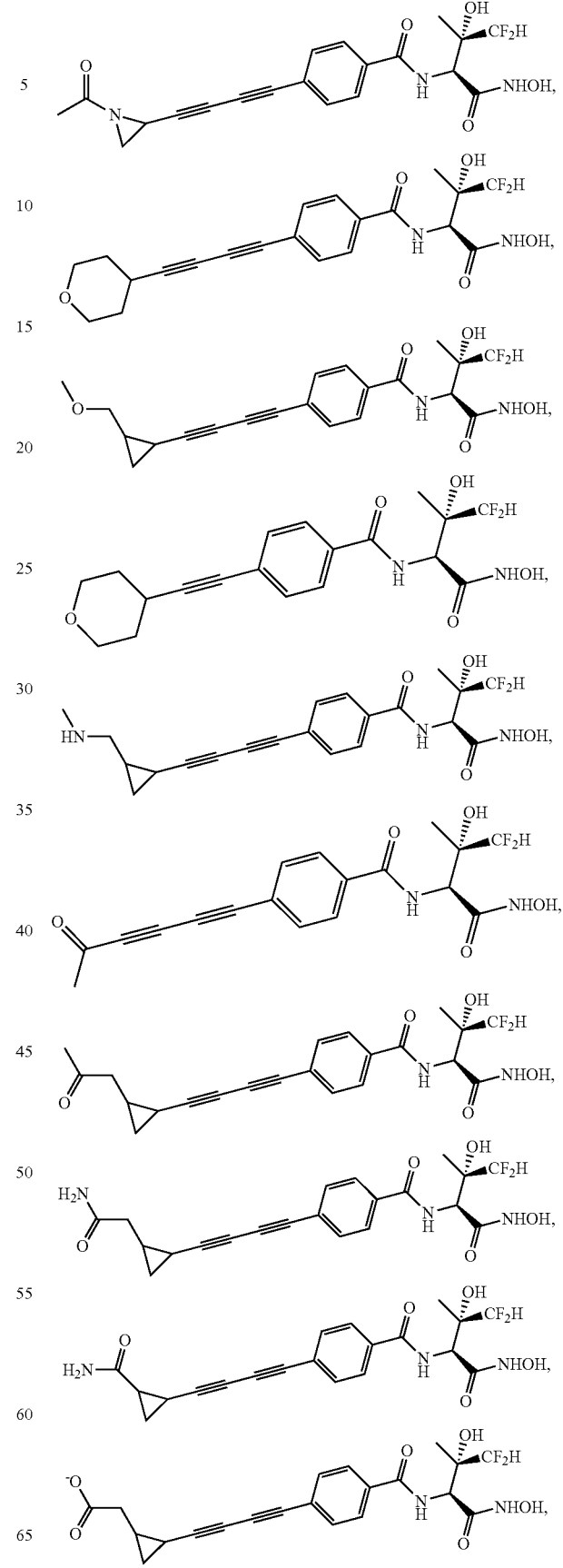

-continued
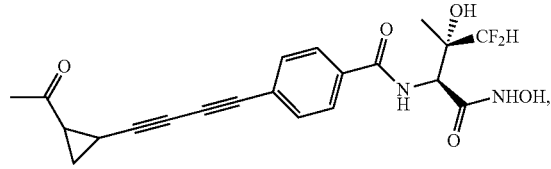
or pharmaceutically acceptable salts thereof.
Other particular compounds of the invention include:
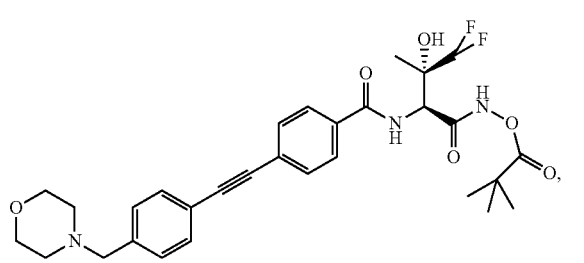
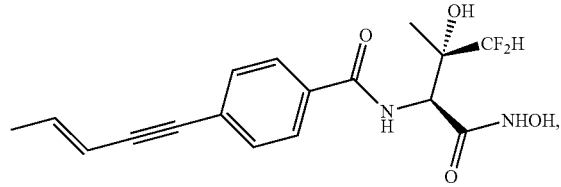
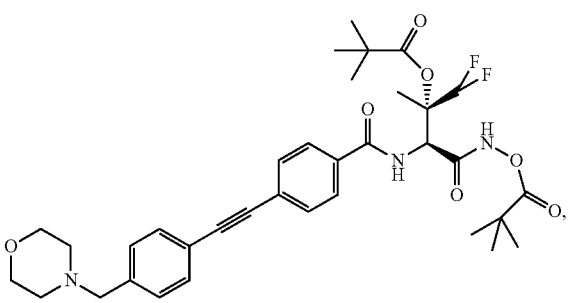
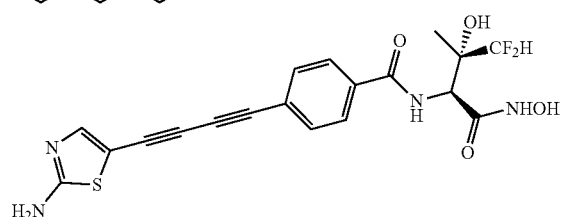
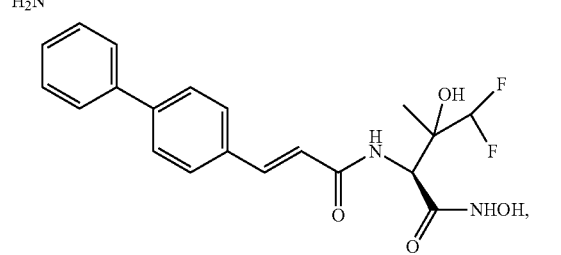
-continued
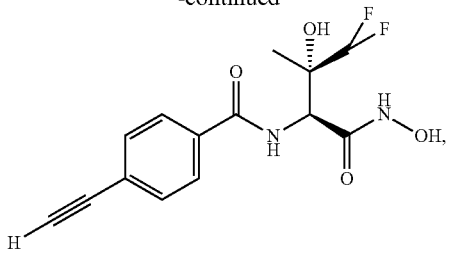
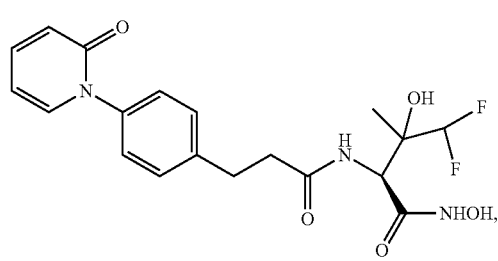
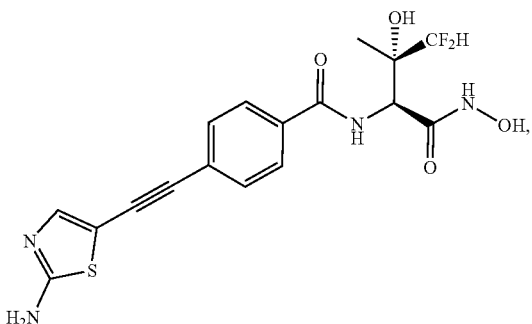
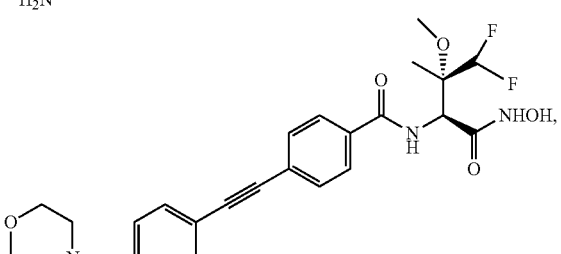
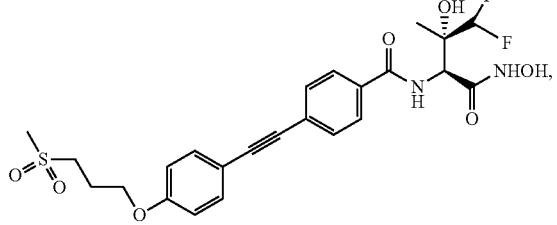
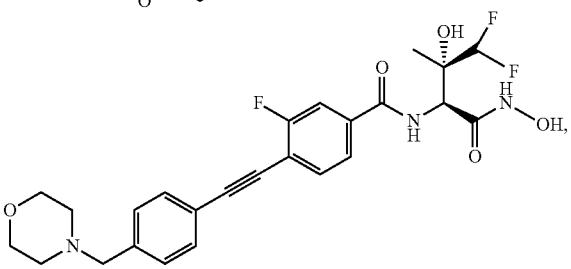

-continued

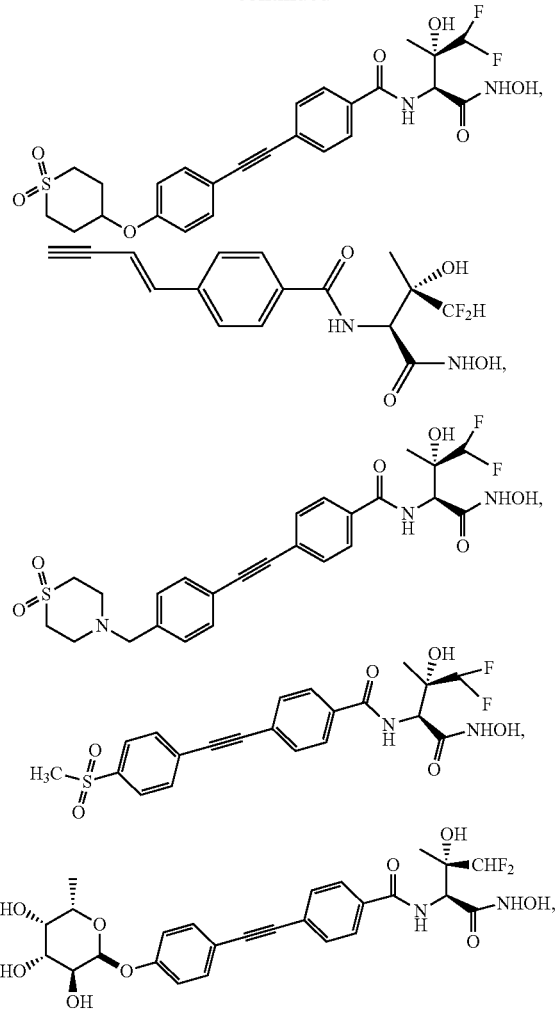

or pharmaceutically acceptable salts thereof.

Therapeutics Applications

The invention provides methods of treating Gram-negative bacterial infections, the method comprising administering to a subject in need of such treatment an effective amount of one or more compounds of the invention Particular Gram-negative bacteria are *Pseudomonas aeruginosa, Stenotrophomonas maltophilia, Burkholderia cepacia, Alcaligenes xylosoxidans, Acinetobacter, Enterobacteriaceae, Haemophilus, Neisseria* species, *Francisella tularensis, Yersinia pestis, Burkholderia pseudomallei, Burkholderia mallei, Rickettsia prowazekii, Coxiella burnetti, Campylobacter jejuni, Shigella, Moraxella catarrhalis*, and *Chlamydia trachomatis*. In one embodiment, the Gram-negative bacteria is *Neisseria gonorrhoeae*. In another embodiment, the Gram-negative bacteria is *Acinetobacter Baumannii*.

Specific enterobacteriaceae is selected from the group consisting of *Serratia, Proteus, Klebsiella, Enterobacter, Citrobacter, Salmonella, Providencia, Morganella, Cedecea, Edwardsiella, Escherichia coli, Enterobacter cloacae*, and *Enterobacter aerogenes*.

In another aspect, the invention provides methods for inhibiting a deacetylase enzyme in Gram-negative bacteria, the method comprising contacting the bacteria with an effective amount of one or more compounds of the invention. A specific deacetylase enzyme is LpxC.

Pharmaceutical Compositions

In another aspect, the present disclosure provides compositions comprising one or more of compounds as described above with respect to formula I and an appropriate carrier, excipient or diluent. The exact nature of the carrier, excipient or diluent will depend upon the desired use for the composition, and may range from being suitable or acceptable for veterinary uses to being suitable or acceptable for human use. The composition may optionally include one or more additional compounds.

When used to treat or prevent such diseases, the compounds described herein may be administered singly, as mixtures of one or more compounds or in mixture or combination with other agents useful for treating such diseases and/or the symptoms associated with such diseases. The compounds may also be administered in mixture or in combination with agents useful to treat other disorders or maladies, such as steroids, membrane stabilizers, 5LO inhibitors, leukotriene synthesis and receptor inhibitors, inhibitors of IgE isotype switching or IgE synthesis, IgG isotype switching or IgG synthesis, β-agonists, tryptase inhibitors, aspirin, COX inhibitors, methotrexate, anti-TNF drugs, retuxin, PD4 inhibitors, p38 inhibitors, PDE4 inhibitors, and antihistamines, to name a few. The compounds may be administered in the form of compounds per se, or as pharmaceutical compositions comprising a compound.

Pharmaceutical compositions comprising the compound(s) may be manufactured by means of conventional mixing, dissolving, granulating, dragee-making levigating, emulsifying, encapsulating, entrapping or lyophilization processes. The compositions may be formulated in conventional manner using one or more physiologically acceptable carriers, diluents, excipients or auxiliaries which facilitate processing of the compounds into preparations which can be used pharmaceutically.

The compounds may be formulated in the pharmaceutical composition per se, or in the form of a hydrate, solvate, N-oxide or pharmaceutically acceptable salt, as previously described. Typically, such salts are more soluble in aqueous solutions than the corresponding free acids and bases, but salts having lower solubility than the corresponding free acids and bases may also be formed.

Pharmaceutical compositions may take a form suitable for virtually any mode of administration, including, for example, topical, ocular, oral, buccal, systemic, nasal, injection, transdermal, rectal, vaginal, etc., or a form suitable for administration by inhalation or insufflation.

For topical administration, the compound(s) may be formulated as solutions, gels, ointments, creams, suspensions, etc. as are well-known in the art. Systemic formulations include those designed for administration by injection, e.g., subcutaneous, intravenous, intramuscular, intrathecal or intraperitoneal injection, as well as those designed for transdermal, transmucosal oral or pulmonary administration.

Useful injectable preparations include sterile suspensions, solutions or emulsions of the active compound(s) in aqueous or oily vehicles. The compositions may also contain formulating agents, such as suspending, stabilizing and/or dispersing agent. The formulations for injection may be presented in unit dosage form, e.g., in ampules or in multidose containers, and may contain added preservatives. Alternatively, the injectable formulation may be provided in powder form for reconstitution with a suitable vehicle, including but not limited to sterile pyrogen free water, buffer, dextrose solution, etc., before use. To this end, the active compound(s) may be dried by any art-known technique, such as lyophilization, and reconstituted prior to use.

For transmucosal administration, penetrants appropriate to the barrier to be permeated are used in the formulation. Such penetrants are known in the art.

For oral administration, the pharmaceutical compositions may take the form of, for example, lozenges, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulfate). The tablets may be coated by methods well known in the art with, for example, sugars, films or enteric coatings.

Liquid preparations for oral administration may take the form of, for example, elixirs, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol, Cremophore™ or fractionated vegetable oils); and preservatives (e.g., methyl or propyl-p-hydroxybenzoates or sorbic acid). The preparations may also contain buffer salts, preservatives, flavoring, coloring and sweetening agents as appropriate.

Preparations for oral administration may be suitably formulated to give controlled release of the compound, as is well known. For buccal administration, the compositions may take the form of tablets or lozenges formulated in conventional manner. For rectal and vaginal routes of administration, the compound(s) may be formulated as solutions (for retention enemas) suppositories or ointments containing conventional suppository bases such as cocoa butter or other glycerides.

For nasal administration or administration by inhalation or insufflation, the compound(s) can be conveniently delivered in the form of an aerosol spray from pressurized packs or a nebulizer with the use of a suitable propellant, e.g., dichlorodifluoromethane, trichlorofluoromethane, dichlorotetrafluoroethane, fluorocarbons, carbon dioxide or other suitable gas. In the case of a pressurized aerosol, the dosage unit may be determined by providing a valve to deliver a metered amount. Capsules and cartridges for use in an inhaler or insufflator (for example capsules and cartridges comprised of gelatin) may be formulated containing a powder mix of the compound and a suitable powder base such as lactose or starch.

For ocular administration, the compound(s) may be formulated as a solution, emulsion, suspension, etc. suitable for administration to the eye. A variety of vehicles suitable for administering compounds to the eye are known in the art.

For prolonged delivery, the compound(s) can be formulated as a depot preparation for administration by implantation or intramuscular injection. The compound(s) may be formulated with suitable polymeric or hydrophobic materials (e.g., as an emulsion in an acceptable oil) or ion exchange resins, or as sparingly soluble derivatives, e.g., as a sparingly soluble salt. Alternatively, transdermal delivery systems manufactured as an adhesive disc or patch which slowly releases the compound(s) for percutaneous absorption may be used. To this end, permeation enhancers may be used to facilitate transdermal penetration of the compound(s).

Alternatively, other pharmaceutical delivery systems may be employed. Liposomes and emulsions are well-known examples of delivery vehicles that may be used to deliver compound(s). Certain organic solvents such as dimethyl sulfoxide (DMSO) may also be employed, although usually at the cost of greater toxicity.

The pharmaceutical compositions may, if desired, be presented in a pack or dispenser device which may contain one or more unit dosage forms containing the compound(s). The pack may, for example, comprise metal or plastic foil, such as a blister pack. The pack or dispenser device may be accompanied by instructions for administration.

The compound(s) described herein, or compositions thereof, will generally be used in an amount effective to achieve the intended result, for example in an amount effective to treat or prevent the particular disease being treated. By therapeutic benefit is meant eradication or amelioration of the underlying disorder being treated and/or eradication or amelioration of one or more of the symptoms associated with the underlying disorder such that the patient reports an improvement in feeling or condition, notwithstanding that the patient may still be afflicted with the underlying disorder. Therapeutic benefit also generally includes halting or slowing the progression of the disease, regardless of whether improvement is realized.

The amount of compound(s) administered will depend upon a variety of factors, including, for example, the particular indication being treated, the mode of administration, whether the desired benefit is prophylactic or therapeutic, the severity of the indication being treated and the age and weight of the patient, the bioavailability of the particular compound(s) the conversation rate and efficiency into active drug compound under the selected route of administration, etc.

Determination of an effective dosage of compound(s) for a particular use and mode of administration is well within the capabilities of those skilled in the art. Effective dosages may be estimated initially from in vitro activity and metabolism assays. For example, an initial dosage of compound for use in animals may be formulated to achieve a circulating blood or serum concentration of the metabolite active compound that is at or above an $IC_{50}$ of the particular compound as measured in as in vitro assay. Calculating dosages to achieve such circulating blood or serum concentrations taking into account the bioavailability of the particular compound via the desired route of administration is well within the capabilities of skilled artisans. Initial dosages of compound can also be estimated from in vivo data, such as animal models. Animal models useful for testing the efficacy of the active metabolites to treat or prevent the various diseases described above are well-known in the art. Animal models suitable for testing the bioavailability and/or metabolism of compounds into active metabolites are also well-known. Ordinarily skilled artisans can routinely adapt such information to determine dosages of particular compounds suitable for human administration.

Dosage amounts will typically be in the range of from about 0.0001 mg/kg/day, 0.001 mg/kg/day or 0.01 mg/kg/day to about 100 mg/kg/day, but may be higher or lower, depending upon, among other factors, the activity of the active compound, the bioavailability of the compound, its metabolism kinetics and other pharmacokinetic properties, the mode of administration and various other factors, discussed above. Dosage amount and interval may be adjusted individually to provide plasma levels of the compound(s) and/or active metabolite compound(s) which are sufficient to maintain therapeutic or prophylactic effect. For example, the compounds may be administered once per week, several times per week (e.g., every other day), once per day or multiple times per day, depending upon, among other things, the mode of administration, the specific indication being treated and the judgment of the prescribing physician. In cases of local administration or selective uptake, such as local topical administration, the effective local concentration of compound(s) and/or active metabolite compound(s) may not be related to plasma concentration. Skilled artisans will be able to optimize effective dosages without undue experimentation.

Definitions

The following terms and expressions used herein have the indicated meanings.

Terms used herein may be preceded and/or followed by a single dash, "-", or a double dash, "=", to indicate the bond order of the bond between the named substituent and its parent moiety; a single dash indicates a single bond and a double dash indicates a double bond. In the absence of a single or double dash it is understood that a single bond is formed between the substituent and its parent moiety; further, substituents are intended to be read "left to right" unless a dash indicates otherwise. For example, $C_1$-$C_6$alkoxycarbonyloxy and —OC(O)$C_1$-$C_6$alkyl indicate the same functionality; similarly arylalkyl and -alkylaryl indicate the same functionality.

The term "alkenyl" as used herein, means a straight or branched chain hydrocarbon containing from 2 to 10 carbons, unless otherwise specified, and containing at least one carbon-carbon double bond. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, 3-decenyl, and 3,7-dimethylocta-2,6-dienyl.

The term "alkoxy" as used herein, means an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The term "alkyl" as used herein, means a straight or branched chain hydrocarbon containing from 1 to 10 carbon atoms unless otherwise specified. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl. When an "alkyl" group is a linking group between two other moieties, then it may also be a straight or branched chain; examples include, but are not limited to —$CH_2$—, —$CH_2CH_2$—, —$CH_2CH_2CHC(CH_3)$—, and —$CH_2CH(CH_2CH_3)CH_2$—.

The term "alkylene" refers to a bivalent alkyl group. An "alkylene chain" is a polymethylene group, i.e., —$(CH_2)_n$—, wherein n is a positive integer, preferably from one to six, from one to four, from one to three, from one to two, or from two to three. A substituted alkylene chain is a polymethylene group in which one or more methylene hydrogen atoms is replaced with a substituent. Suitable substituents include those described below for a substituted aliphatic group. An alkylene chain also may be substituted at one or more positions with an aliphatic group or a substituted aliphatic group.

The term "alkynyl" as used herein, means a straight or branched chain hydrocarbon group containing from 2 to 10 carbon atoms and containing at least one carbon-carbon triple bond. Representative examples of alkynyl include, but are not limited, to acetylenyl, 1-propynyl, 2-propynyl, 3-butynyl, 2-pentynyl, and 1-butynyl.

The term "aryl," as used herein, means a phenyl (i.e., monocyclic aryl), or a bicyclic ring system containing at least one phenyl ring or an aromatic bicyclic ring containing only carbon atoms in the aromatic bicyclic ring system. The bicyclic aryl can be azulenyl, naphthyl, or a phenyl fused to a monocyclic cycloalkyl, a monocyclic cycloalkenyl, or a monocyclic heterocyclyl. The bicyclic aryl is attached to the parent molecular moiety through any carbon atom contained within the phenyl portion of the bicyclic system, or any carbon atom with the napthyl or azulenyl ring. The fused monocyclic cycloalkyl or monocyclic heterocyclyl portions of the bicyclic aryl are optionally substituted with one or two oxo and/or thia groups. Representative examples of the bicyclic aryls include, but are not limited to, azulenyl, naphthyl, dihydroinden-1-yl, dihydroinden-2-yl, dihydroinden-3-yl, dihydroinden-4-yl, 2,3-dihydroindol-4-yl, 2,3-dihydroindol-5-yl, 2,3-dihydroindol-6-yl, 2,3-dihydroindol-7-yl, inden-1-yl, inden-2-yl, inden-3-yl, inden-4-yl, dihydronaphthalen-2-yl, dihydronaphthalen-3-yl, dihydronaphthalen-4-yl, dihydronaphthalen-1-yl, 5,6,7,8-tetrahydronaphthalen-1-yl, 5,6,7,8-tetrahydronaphthalen-2-yl, 2,3-dihydrobenzofuran-4-yl, 2,3-dihydrobenzofuran-5-yl, 2,3-dihydrobenzofuran-6-yl, 2,3-dihydrobenzofuran-7-yl, benzo[d][1,3]dioxol-4-yl, benzo[d][1,3]dioxol-5-yl, 2H-chromen-2-on-5-yl, 2H-chromen-2-on-6-yl, 2H-chromen-2-on-7-yl, 2H-chromen-2-on-8-yl, isoindoline-1,3-dion-4-yl, isoindoline-1,3-dion-5-yl, inden-1-on-4-yl, inden-1-on-5-yl, inden-1-on-6-yl, inden-1-on-7-yl, 2,3-dihydrobenzo[b][1,4]dioxan-5-yl, 2,3-dihydrobenzo[b][1,4]dioxan-6-yl, 2H-benzo[b][1,4]oxazin3(4H)-on-5-yl, 2H-benzo[b][1,4]oxazin3(4H)-on-6-yl, 2H-benzo[b][1,4]oxazin3(4H)-on-7-yl, 2H-benzo[b][1,4]oxazin3(4H)-on-8-yl, benzo[d]oxazin-2(3H)-on-5-yl, benzo[d]oxazin-2(3H)-on-6-yl, benzo[d]oxazin-2(3H)-on-7-yl, benzo[d]oxazin-2(3H)-on-8-yl, quinazolin-4(3H)-on-5-yl, quinazolin-4(3H)-on-6-yl, quinazolin-4(3H)-on-7-yl, quinazolin-4(3H)-on-8-yl, quinoxalin-2(1H)-on-5-yl, quinoxalin-2(1H)-on-6-yl, quinoxalin-2(1H)-on-7-yl, quinoxalin-2(1H)-on-8-yl, benzo[d]thiazol-2(3H)-on-4-yl, benzo[d]thiazol-2(3H)-on-5-yl, benzo[d]thiazol-2(3H)-on-6-yl, and, benzo[d]thiazol-2(3H)-on-7-yl. In certain embodiments, the bicyclic aryl is (i) naphthyl or (ii) a phenyl ring fused to either a 5 or 6 membered monocyclic cycloalkyl, a 5 or 6 membered monocyclic cycloalkenyl, or a 5 or 6 membered monocyclic heterocyclyl, wherein the fused cycloalkyl, cycloalkenyl, and heterocyclyl groups are optionally substituted with one or two groups which are independently oxo or thia.

The terms "cyano" and "nitrile" as used herein, mean a —CN group.

The term "cycloalkyl" as used herein, means a monocyclic or a bicyclic cycloalkyl ring system. Monocyclic ring systems are cyclic hydrocarbon groups containing from 3 to 8 carbon atoms, where such groups can be saturated or unsaturated, but not aromatic. In certain embodiments, cycloalkyl groups are fully saturated. Examples of monocyclic cycloalkyls include cyclopropyl, cyclobutyl, cyclopentyl, cyclopentenyl, cyclohexyl, cyclohexenyl, cycloheptyl, and cyclooctyl. Bicyclic cycloalkyl ring systems are bridged monocyclic rings or fused bicyclic rings. Bridged monocyclic rings contain a monocyclic cycloalkyl ring where two non-adjacent carbon atoms of the monocyclic ring are linked by an alkylene bridge of between one and three additional carbon atoms (i.e., a bridging group of the form —$(CH_2)_w$—, where w is 1, 2, or 3). Representative examples of bicyclic ring systems include, but are not limited to, bicyclo[3.1.1]heptane, bicyclo[2.2.1]heptane, bicyclo[2.2.2]octane, bicyclo[3.2.2]nonane, bicyclo[3.3.1] nonane, and bicyclo[4.2.1]nonane. Fused bicyclic cycloalkyl ring systems contain a monocyclic cycloalkyl ring fused to either a phenyl, a monocyclic cycloalkyl, a monocyclic cycloalkenyl, a monocyclic heterocyclyl, or a monocyclic heteroaryl. The bridged or fused bicyclic cycloalkyl is attached to the parent molecular moiety through any carbon atom contained within the monocyclic cycloalkyl ring. Cycloalkyl groups are optionally substituted with one or two groups which are independently oxo or thia. In certain embodiments, the fused bicyclic cycloalkyl is a 5 or 6 membered monocyclic cycloalkyl ring fused to either a phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the fused bicyclic cycloalkyl is optionally substituted by one or two groups which are independently oxo or thia.

The term "halo" or "halogen" as used herein, means —Cl, —Br, —I or —F.

The terms "haloalkyl" and "haloalkoxy" refer to an alkyl or alkoxy group, as the case may be, which is substituted with one or more halogen atoms.

The term "heteroaryl," as used herein, means a monocyclic heteroaryl or a bicyclic ring system containing at least one heteroaromatic ring. The monocyclic heteroaryl can be a 5 or 6 membered ring. The 5 membered ring consists of two double bonds and one, two, three or four nitrogen atoms and optionally one oxygen or sulfur atom. The 6 membered ring consists of three double bonds and one, two, three or four nitrogen atoms. The 5 or 6 membered heteroaryl is connected to the parent molecular moiety through any carbon atom or any nitrogen atom contained within the heteroaryl. Representative examples of monocyclic heteroaryl include, but are not limited to, furyl, imidazolyl, isoxazolyl, isothiazolyl, oxadiazolyl, oxazolyl, pyridinyl, pyridazinyl, pyrimidinyl, pyrazinyl, pyrazolyl, pyrrolyl, tetrazolyl, thiadiazolyl, thiazolyl, thienyl, triazolyl, and triazinyl. The bicyclic heteroaryl consists of a monocyclic heteroaryl fused to a phenyl, a monocyclic cycloalkyl, a monocyclic cycloalkenyl, a monocyclic heterocyclyl, or a monocyclic heteroaryl. The fused cycloalkyl or heterocyclyl portion of the bicyclic heteroaryl group is optionally substituted with one or two groups which are independently oxo or thia. When the bicyclic heteroaryl contains a fused cycloalkyl, cycloalkenyl, or heterocyclyl ring, then the bicyclic heteroaryl group is connected to the parent molecular moiety through any carbon or nitrogen atom contained within the monocyclic heteroaryl portion of the bicyclic ring system. When the bicyclic heteroaryl is a monocyclic heteroaryl fused to a benzo ring, then the bicyclic heteroaryl group is connected to the parent molecular moiety through any carbon atom or nitrogen atom within the bicyclic ring system. Representative examples of bicyclic heteroaryl include, but are not limited to, benzimidazolyl, benzofuranyl, benzothienyl, benzoxadiazolyl, benzoxathiadiazolyl, benzothiazolyl, cinnolinyl, 5,6-dihydroquinolin-2-yl, 5,6-dihydroisoquinolin-1-yl, furopyridinyl, indazolyl, indolyl, isoquinolinyl, naphthyridinyl, quinolinyl, purinyl, 5,6,7,8-tetrahydroquinolin-2-yl, 5,6,7,8-tetrahydroquinolin-3-yl, 5,6,7,8-tetrahydroquinolin-4-yl, 5,6,7,8-tetrahydroisoquinolin-1-yl, thienopyridinyl, 4,5,6,7-tetrahydrobenzo[c][1,2,5] oxadiazolyl, and 6,7-dihydrobenzo[c][1,2,5]oxadiazol-4 (5H)-onyl. In certain embodiments, the fused bicyclic heteroaryl is a 5 or 6 membered monocyclic heteroaryl ring fused to either a phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the fused cycloalkyl, cycloalkenyl, and heterocyclyl groups are optionally substituted with one or two groups which are independently oxo or thia.

The terms "heterocyclyl" and "heterocycloalkyl" as used herein, mean a monocyclic heterocycle or a bicyclic heterocycle. The monocyclic heterocycle is a 3, 4, 5, 6 or 7 membered ring containing at least one heteroatom independently selected from the group consisting of O, N, and S where the ring is saturated or unsaturated, but not aromatic. The 3 or 4 membered ring contains 1 heteroatom selected from the group consisting of O, N and S. The 5 membered ring can contain zero or one double bond and one, two or three heteroatoms selected from the group consisting of O, N and S. The 6 or 7 membered ring contains zero, one or two double bonds and one, two or three heteroatoms selected from the group consisting of O, N and S. The monocyclic heterocycle is connected to the parent molecular moiety through any carbon atom or any nitrogen atom contained within the monocyclic heterocycle. Representative examples of monocyclic heterocycle include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, piperazinyl, piperidinyl, pyranyl, pyrazolinyl, pyrazolidinyl, pyrrolinyl, pyrrolidinyl, tetrahydrofuranyl, tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, and trithianyl. The bicyclic heterocycle is a monocyclic heterocycle fused to either a phenyl, a monocyclic cycloalkyl, a monocyclic cycloalkenyl, a monocyclic heterocycle, or a monocyclic heteroaryl. The bicyclic heterocycle is connected to the parent molecular moiety through any carbon atom or any nitrogen atom contained within the monocyclic heterocycle portion of the bicyclic ring system. Representative examples of bicyclic heterocyclyls include, but are not limited to, 2,3-dihydrobenzofuran-2-yl, 2,3-dihydrobenzofuran-3-yl, indolin-1-yl, indolin-2-yl, indolin-3-yl, 2,3-dihydrobenzothien-2-yl, decahydroquinolinyl, decahydroisoquinolinyl, octahydro-1H-indolyl, and octahydrobenzofuranyl. Heterocyclyl groups are optionally substituted with one or two groups which are independently oxo or thia. In certain embodiments, the bicyclic heterocyclyl is a 5 or 6 membered monocyclic heterocyclyl ring fused to phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the bicyclic heterocyclyl is optionally substituted by one or two groups which are independently oxo or thia.

The term "oxo" as used herein means a =O group.

The term "saturated" as used herein means the referenced chemical structure does not contain any multiple carbon-carbon bonds. For example, a saturated cycloalkyl group as defined herein includes cyclohexyl, cyclopropyl, and the like.

The term "substituted", as used herein, means that a hydrogen radical of the designated moiety is replaced with the radical of a specified substituent, provided that the substitution results in a stable or chemically feasible compound. The term "substitutable", when used in reference to a designated atom, means that attached to the atom is a hydrogen radical, which can be replaced with the radical of a suitable substituent.

The phrase "one or more" substituents, as used herein, refers to a number of substituents that equals from one to the maximum number of substituents possible based on the number of available bonding sites, provided that the above conditions of stability and chemical feasibility are met. Unless otherwise indicated, an optionally substituted group may have a substituent at each substitutable position of the group, and the substituents may be either the same or different. As used herein, the term "independently selected" means that the same or different values may be selected for multiple instances of a given variable in a single compound.

The term "thia" as used herein means a =S group.

The term "unsaturated" as used herein means the referenced chemical structure contains at least one multiple carbon-carbon bond, but is not aromatic. For example, a unsaturated cycloalkyl group as defined herein includes cyclohexenyl, cyclopentenyl, cyclohexadienyl, and the like.

It will be apparent to one skilled in the art that certain compounds of this disclosure may exist in tautomeric forms, all such tautomeric forms of the compounds being within the scope of the disclosure. Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the disclosure. Both the R and the S stereochemical isomers, as well as all mixtures thereof, are included within the scope of the disclosure.

"Pharmaceutically acceptable" refers to those compounds, materials, compositions, and/or dosage forms which are, within the scope of sound medical judgment, suitable for contact with the tissues of human beings and animals without excessive toxicity, irritation, allergic response, or other problems or complications commensurate with a reasonable benefit/risk ratio or which have otherwise been approved by the United States Food and Drug Administration as being acceptable for use in humans or domestic animals.

"Pharmaceutically acceptable salt" refers to both acid and base addition salts.

"Therapeutically effective amount" refers to that amount of a compound which, when administered to a subject, is sufficient to effect treatment for a disease or disorder described herein. The amount of a compound which constitutes a "therapeutically effective amount" will vary depending on the compound, the disorder and its severity, and the age of the subject to be treated, but can be determined routinely by one of ordinary skill in the art.

"Treating" or "treatment" as used herein covers the treatment of a disease or disorder described herein, in a subject, preferably a human, and includes:
  i. inhibiting a disease or disorder, i.e., arresting its development;
  ii. relieving a disease or disorder, i.e., causing regression of the disorder;
  iii. slowing progression of the disorder; and/or
  iv. inhibiting, relieving, ameliorating, or slowing progression of one or more symptoms of the disease or disorder "Subject" refers to a warm blooded animal such as a mammal, preferably a human, or a human child, which is afflicted with, or has the potential to be afflicted with one or more diseases and disorders described herein.

Methods of Preparation

The compounds of the present disclosure may be prepared by use of known chemical reactions and procedures. Representative methods for synthesizing compounds of the disclosure are presented below. It is understood that the nature of the substituents required for the desired target compound often determines the preferred method of synthesis. All variable groups of these methods are as described in the generic description if they are not specifically defined below.

Synthesis of unsymmetrical diynes has recently been the subject of extensive research. A survey of the literature indicates that diynes can be formed under various conditions and many useful methods have been reported. Balaraman improved the synthesis of symmetrical and unsymmetrical 1,3-diynes by employing catalytic amounts (0.1 equivalent) of copper(II) acetate in the presence of a stoichiometric amount of piperidine in 1,2-dichloroethane under aerobic condition (Balaraman K, Kesavan V (2010) Efficient Copper (II) Acetate Catalyzed Homo- and Heterocoupling of Terminal Alkynes at Ambient Conditions. *Synthesis-Stuttgart* 2010: 3461-3466). With this method, the yield of unsymmetrical 1,3 diyne was over 60%. Other syntheses of unsymmetrical diynes using an alkynyl halide and a terminal alkyne have been reported (Yue Weng et al. (2012) Rational Design of a Palladium-Catalyzed Csp-Csp Cross-Coupling Reaction Inspired by Kinetic Studies. *Angew Chem Int Ed* 51: 9547-9551; Huan-Feng Jiang A-ZW (2007) Copper-Catalyzed Cross-Coupling Reactions of Bromoalkynols with Terminal Alkynes in Supercritical Carbon Dioxide. *Synthesis* 11: 1649-1654).

The present inventors have determined an efficient and scalable route to the compounds of the invention. Thus, in one aspect, the disclosure provides methods for preparing a compound of the formula:

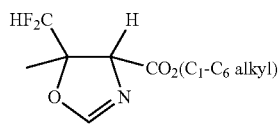

or a salt thereof, the method comprising reacting 1,1-difluoroacetone and $C_1$-$C_6$ alkyl α-isocyanoacetate in presence of transition metal catalyst and base. Representative compounds prepared by this method are:

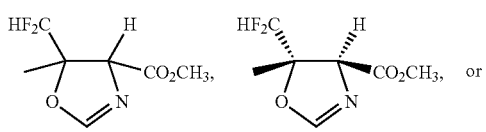

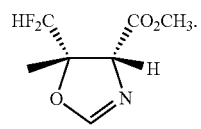

One aspect of the disclosure provides methods for preparing a compound of formula:

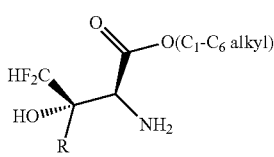

or a salt thereof, wherein R is optionally substituted $C_1$-$C_6$ alkyl;

the method comprising reacting R—C(O)—CHF$_2$ and a $C_1$-$C_6$ alkyl α-isocyanoacetate in presence of a transition metal catalyst and base to obtain an oxazoline of the formula:

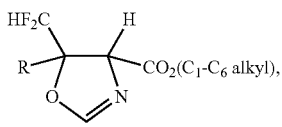

wherein R is optionally substituted $C_1$-$C_6$ alkyl. In one embodiment, the disclosure provides methods for preparing a compound of formula:

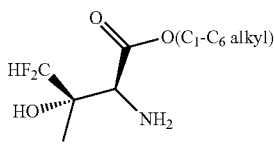

or a salt thereof, the method comprising reacting 1,1-difluoroacetone and a $C_1$-$C_6$ alkyl α-isocyanoacetate in presence of a transition metal catalyst and base to obtain an oxazoline of the formula:

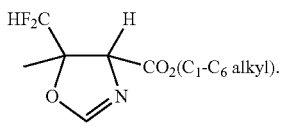

In one embodiment, the method further comprises hydrolyzing the oxazoline. Representative compounds prepared by this method are:

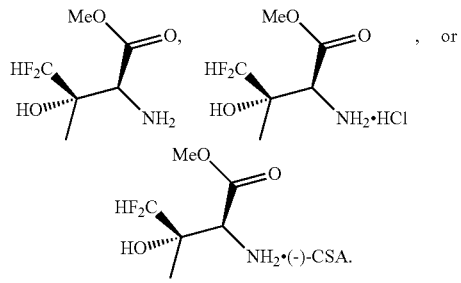

In one embodiment of the preceeding methods, the transition metal catalyst is present in an amount of about 0.01 mol % to about 10 mol %, or about 0.1 mol % to about 10 mol %, or about 1 mol % to about 10 mol %, or about 0.01 mol % to about 5 mol %, or about 0.1 mol % to about 5 mol %, or about 1 mol % to about 5 mol %, or about 2 mol % to about 5 mol %, or about 3 mol % to about 5 mol %. In one embodiment of the preceding methods, the transition metal catalyst is a copper(I) catalyst, e.g., CuCl.

In one embodiment of the preceding methods, the base is present in an amount of about 0.01 mol % to about 10 mol %, or about 0.1 mol % to about 10 mol %, or about 1 mol % to about 10 mol %, or about 0.01 mol % to about 5 mol %, or about 0.1 mol % to about 5 mol %, or about 1 mol % to about 5 mol %, or about 4 mol % to about 6 mol %, or about 3 mol % to about 7 mol %. Examples of suitable bases for use in the preceding methods are triethylamine, trimethylamine, n-butylamine, diethylamine, dimethylamine, ethylenediamine, or methylamine, morpholine.

One embodiment of the preceding methods is illustrated in Scheme 1.

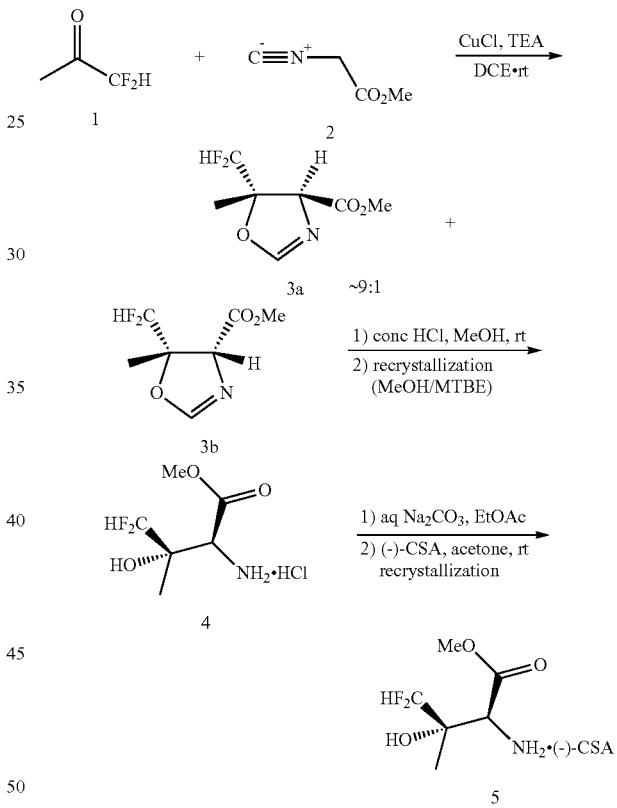

Scheme 1

Difluoroacetone 1 was reacted with methyl α-isocyanoacetate 2 to give the diastereomeric mixture of oxazolines 3 (a and b). The reaction was performed in dry 1,1-dichloroethane at ambient temperature in the presence of 4 mol % CuCl and 5 mol % TEA. The ratio of oxazoline diastereomers 3a/3b is 87:13, which was determined by NMR chemical shifts of the crude reaction mixture after removal of the catalyst and solvent. Replacing DCE with DCM as the reaction solvent also provided similar results in terms of chemical yield and diastereoselectivity. Control over the diastereomeric ratio can be achieved by modifying the nature of the ester alkyl group. For example, when the difluoroacetone 1 was reacted with ethyl α-isocyanoacetate under otherwise identical reaction conditions, the ratio of oxazoline diastereomers 3a/3b was decreased. Hydrolysis of the diastereomeric mixture of oxazolines 3a and 3b in methanolic HCl at room temperature afforded the corresponding amino acid hydrochloride salts 4a and 4b. The desired diastereomer 4a can be obtained in high purity by recrystallization from an appropriate solvent system. For example, diastereomer 4a was obtained in >99% purity after recrystallization from MeOH/MTBE at room temperature with a chemical yield of 42%. In order to get optically pure 5, the amino acid hydrochloride salt 4a was neutralized using $Na_2CO_3$ and the racemic free base was reacted with equimolar amounts of (−)-10-camphorsulfonic acid ((−)-CSA) at room temperature in acetone. Upon cooling the reaction mixture the desired amino ester 5 was obtained in 60% yield of the desired single enantiomer. Optical purity was established using $^1H$ NMR and $^{19}F$ NMR as follows: $^1H$ NMR and $^{19}F$ NMR of racemic hydrochloride salt in the presence of 10 fold excess of (+)-tartaric acid in $CD_3OD$, yielded a spectrum with well-resolved peaks. Particularly, the $^{19}F$, α-CH and ester of $CH_3$ of the racemic methyl ester were well resolved and readily identified when recorded in the presence of excess tartaric acid. It is to be noted that $^1H$ NMR and $^{19}F$ NMR of recrystallized of optically pure sample of 5 in the presence of 10 fold excess of (+)-tartaric acid in $CD_3OD$ displayed only one set of peaks corresponding to the desired enantiomer.

Another aspect of the disclosure provides methods for preparing a benzamide of formula I, I-A, II, or II-A. This aspect also provides methods for preparing any one of the benzamide compounds disclosed in International Publication Nos. WO 2012/031298 and WO 2015/024010. The methods of this aspect comprise:

coupling an α-amino ester of the formula:

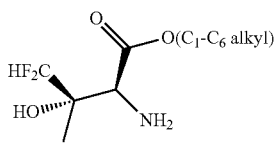

with an appropriate benzoic acid of the formula:

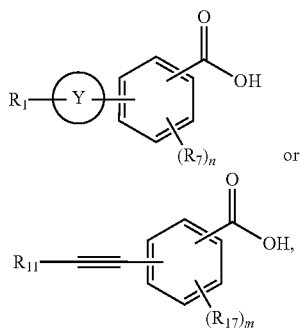

wherein Y, $R_1$, $R_{11}$, $R_7$, $R_{17}$, m and n are as defined above, to generate the desired benzamide.

Any of the various coupling methods can be exploited to produce the desired amides. A representative embodiment of this method is illustrated in Scheme 2.

Scheme 2

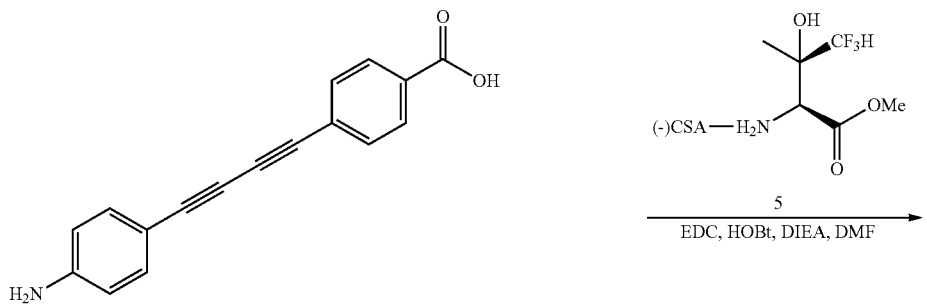

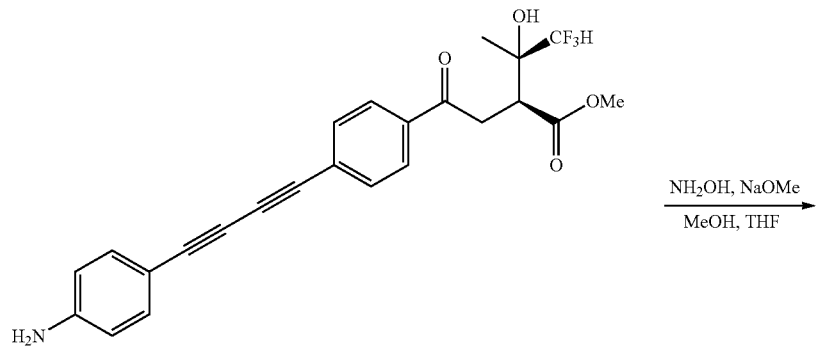

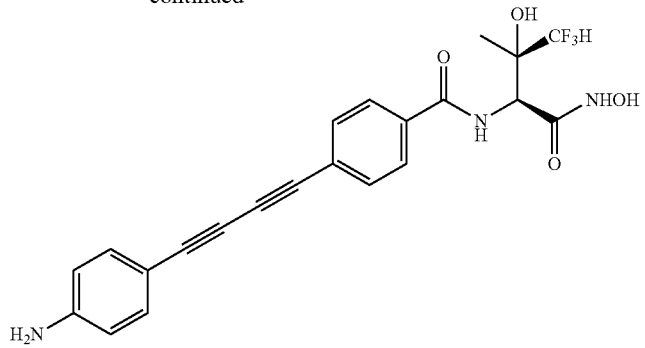

8

Amino ester 5 and diacetylene benzoic acid 6 were coupled under EDC/HOBt conditions provided the diacetylene ester 7. Treatment of 7 with hydroxylamine and sodium methoxide provided hydroxamate 8 in 67% yield over two steps.

Another aspect of the disclosure provides methods for preparing a benzamide compound of the formula:

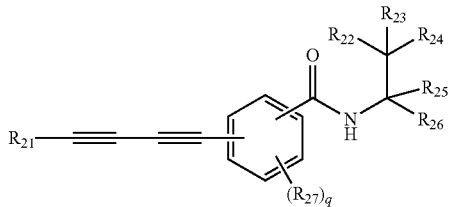

or a pharmaceutically acceptable salt thereof, wherein
q is an integer 0, 1, 2, 3, or 4;
$R_{21}$ is $C_1$-$C_6$ alkyl, $C_1$-$C_6$ haloalkyl, —CO($C_1$-$C_6$ alkyl), —$C_1$-$C_6$ alkyl-CO($C_1$-$C_6$ alkyl), —$C_1$-$C_6$ alkyl-$CO_2$H, $C_3$-$C_8$ cycloalkyl optionally substituted with $R_{28}$, ($C_3$-$C_8$ cycloalkyl)$C_1$-$C_6$ alkyl- optionally substituted with $R_{28}$, aryl optionally substituted with $R_{28}$, (aryl)$C_1$-$C_6$ alkyl- optionally substituted with $R_{28}$, heteroaryl optionally substituted with $R_{28}$, (heteroaryl)$C_1$-$C_6$ alkyl- optionally substituted with $R_{28}$, heterocyclyl optionally substituted with $R_{28}$, or (heterocycloalkyl)$C_1$-$C_6$ alkyl- optionally substituted with $R_{28}$,
$R_{22}$ is selected from the group consisting of hydrogen, halogen, $C_1$-$C_6$ alkyl, $C_1$-$C_6$ haloalkyl, —$NH_2$, —NH($C_1$-$C_6$ alkyl), —N($C_1$-$C_6$ alkyl)$_2$, —OH, $C_1$-$C_6$ alkoxy, $C_1$-$C_6$ haloalkoxy, —SH, —S($C_1$-$C_6$ alkyl), hydroxy($C_1$-$C_6$ alkyl), alkoxy($C_1$-$C_6$ alkyl), and amino($C_1$-$C_6$ alkyl);
$R_{23}$ is selected from the group consisting of hydrogen, halogen, $C_1$-$C_6$ alkyl, $C_1$-$C_6$ haloalkyl, —$NH_2$, —NH($C_1$-$C_6$ alkyl), —N($C_1$-$C_6$ alkyl)$_2$, —OH, $C_1$-$C_6$ alkoxy, $C_1$-$C_6$ haloalkoxy, —SH, —S($C_1$-$C_6$ alkyl), hydroxy($C_1$-$C_6$ alkyl), alkoxy($C_1$-$C_6$ alkyl), amino($C_1$-$C_6$ alkyl), —NHCO($C_1$-$C_6$ alkyl), —$NHCONH_2$, —NHCONH($C_1$-$C_6$ alkyl), —OCO($C_1$-$C_6$ alkyl), and —NHCO($C_1$-$C_6$ alkoxy);
$R_{24}$ is $C_1$-$C_6$ alkyl or $C_1$-$C_6$ haloalkyl;
$R_{25}$ is independently selected from the group consisting of halogen, —$NO_2$, —CN, $C_1$-$C_6$ alkyl, $C_1$-$C_6$ haloalkyl, —$NH_2$, —NH($C_1$-$C_6$ alkyl), —N($C_1$-$C_6$ alkyl)$_2$, —OH, $C_1$-$C_6$ alkoxy, $C_1$-$C_6$ haloalkoxy, —$CONH_2$, —CON($C_1$-$C_6$ alkyl), —CON($C_1$-$C_6$ alkyl)$_2$, —CONH—OH, —CONH—OCO($C_1$-$C_6$ alkyl), —CONH—$NH_2$, —$CO_2$H, and —$CO_2$($C_1$-$C_6$ alkyl);
$R_{26}$ is hydrogen or $C_1$-$C_6$ alkyl;
each $R_{27}$ is independently selected from the group consisting of halogen, —$NO_2$, —CN, $C_1$-$C_6$ alkyl, $C_1$-$C_6$ haloalkyl, —$NH_2$, —NH($C_1$-$C_6$ alkyl), —N($C_1$-$C_6$ alkyl)$_2$, —OH, $C_1$-$C_6$ alkoxy, and $C_1$-$C_6$ haloalkoxy; and
each $R_{28}$ is independently selected from the group consisting of halogen, —$NO_2$, —CN, $C_1$-$C_6$ alkyl, $C_1$-$C_6$ haloalkyl, —$NH_2$, —NH($C_1$-$C_6$ alkyl), —N($C_1$-$C_6$ alkyl)$_2$, —OH, $C_1$-$C_6$ alkoxy, $C_1$-$C_6$ haloalkoxy, —$C_1$-$C_6$ alkyl-OH, —$C_1$-$C_6$ alkyl-($C_1$-$C_6$ alkoxy), —$C_1$-$C_6$ alkyl-$NH_2$, —$C_1$-$C_6$ alkyl-NH—$C_1$-$C_6$ alkyl), —$C_1$-$C_6$ alkyl-N($C_1$-$C_6$ alkyl)$_2$, —$C_1$-$C_6$ alkyl-NH($SO_2C_1$-$C_6$ alkyl), —$CONH_2$, —CON($C_1$-$C_6$ alkyl), —CON($C_1$-$C_6$ alkyl)$_2$, —NH($SO_2C_1$-$C_6$ alkyl), —CONH—OH, —CONH—OCO($C_1$-$C_6$ alkyl), —C(NH)NH—OH, —CONH—$NH_2$, —CO($C_1$-$C_6$ alkyl), —$CO_2$H, —$CO_2$($C_1$-$C_6$ alkyl), —$C_1$-$C_6$ alkyl-$CONH_2$, —$C_1$-$C_6$ alkyl-CON($C_1$-$C_6$ alkyl), —$C_1$-$C_6$ alkyl-CON($C_1$-$C_6$ alkyl)$_2$, —$C_1$-$C_6$ alkyl-CONH—OH, —$C_1$-$C_6$ alkyl-CO($C_1$-$C_6$ alkyl), —$C_1$-$C_6$ alkyl-$CO_2$H, and —$C_1$-$C_6$ alkyl-$CO_2$($C_1$-$C_6$ alkyl); or two $R_{28}$ groups when attached to the same carbon atom form =O;
the method comprising
reacting a haloethynyl compound of the formula:

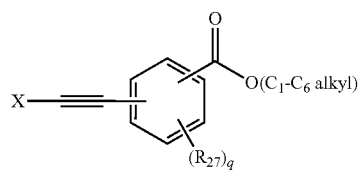

wherein X is halogen (e.g., Br, Cl, F, I), with a substitute alkyne of the formula

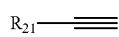

in the presence of transition metal catalyst and base.

In one embodiment of this method, the transition metal catalyst is present in an amount of about 0.01 mol % to about 10 mol %, or about 0.1 mol % to about 10 mol %, or about 1 mol % to about 10 mol %, or about 0.01 mol % to about 5 mol %, or about 0.1 mol % to about 5 mol %, or about 1 mol % to about 5 mol %, or about 2 mol % to about 5 mol %, or about 3 mol % to about 5 mol %. In one embodiment of this method, the transition metal catalyst is a copper(I) catalyst, such as for example, CuCl, CuI, CuBr; or the transition metal catalyst is a copper(II) catalyst, such as, for example, Cu(OAc)$_2$. In one embodiment of this method, the base is piperidine, pyridine, triethylamine, trimethylamine, n-butylamine, diethylamine, dimethylamine, ethylenediamine, or methylamine, morpholine.

The reaction is conveniently carried out in the presence of an appropriate solvent. Suitable solvents include polar, aprotic solvents, such as, dichloromethane.

One embodiment of this method is illustrated in Scheme 3.

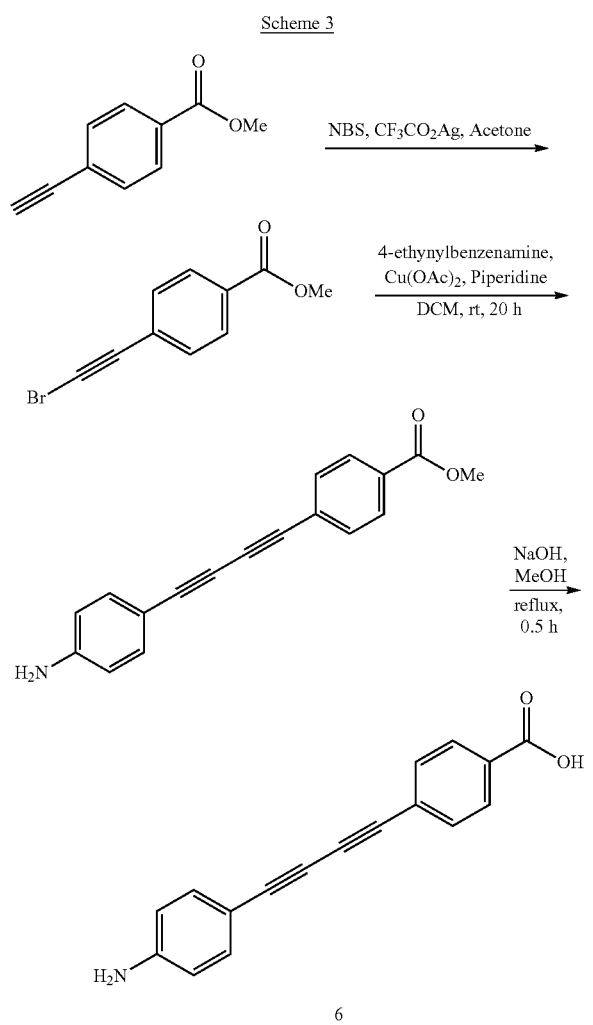

Treatment of methyl 4-ethynylbenzoate with N-bromosuccinimide in the presence of silver trifluoroacetate as a catalyst provided 4-(bromoethynyl)benzoate in 82% yield. The reaction of 4-(bromoethynyl)benzoate with near stoichiometric amount of 4-ethynylbenzenamine (1.05 equivalents) and copper (II) acetate (0.05 equivalent) as a catalyst proceeded efficiently to give the intermediate diyne (92% yield). The crude intermediate diyne can be hydrolyzed to give diacetylene acid 6 without purification.

Another aspect of the disclosure provides a crystalline form of an amine hydrochloride salt of the formula:

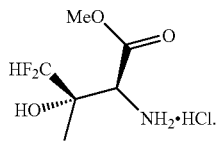

In one embodiment of this aspect, the crystalline form is the monoclinic P 1 21 1 space group having unit cell parameters: a=about 12.5 Å, b=about 5.5 Å, c=about 14.5 Å, α=about 90°, β=about 103.8°, γ=about 90°, Volume=about 966 Å$^3$, Z=4, and/or density (calculated) 1.5 g/cm$^3$. In another embodiment, the crystalline form is the monoclinic P 1 21 1 space group having unit cell parameters: a=12.4761 (5) Å, b=5.4881(2)Å, c=14.5393(5) Å, α=90°, β=103.817 (2)°, γ=90°, Volume=966.70(6) Å$^3$, Z=4, and density (calculated) 1.509 g/cm$^3$.

Still another aspect of the disclosure provides a crystalline form of an amine camphor sulfonic acid salt of the formula:

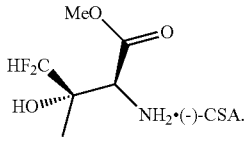

In one embodiment of this aspect, the crystalline form is the orthorhombic P 21 21 21 space group having unit cell parameters: a=about 6.3 Å, b=about 12.8 Å, c=about 22.9 Å, α=about 90°, β=about 90°, γ=about 90°, Volume=about 1852.8(10) Å$^3$, Z=4, and density (calculated) about 1.49 g/cm$^3$. In one embodiment, the crystalline form is the orthorhombic P 21 21 21 space group having unit cell parameters: a=6.3347(2) Å, b=12.7819(4) Å, c=22.8824(7) Å, α=90°, β=90°, γ=90°, Volume=1852.78(10) Å$^3$, Z=4, and density (calculated) 1.489 g/cm$^3$.

General Procedure

Those having skill in the art will recognize that the starting materials and reaction conditions may be varied, the sequence of the reactions altered, and additional steps employed to produce compounds encompassed by the present disclosure, as demonstrated by the following examples. Many general references providing commonly known chemical synthetic schemes and conditions useful for synthesizing the disclosed compounds are available (see, e.g., Smith and March, March's Advanced Organic Chemistry: Reactions, Mechanisms, and Structure, Fifth Edition, Wiley-Interscience, 2001; or Vogel, A Textbook of Practical Organic Chemistry, Including Qualitative Organic Analysis, Fourth Edition, New York: Longman, 1978).

Starting materials can be obtained from commercial sources or prepared by well-established literature methods known to those of ordinary skill in the art. The reactions are performed in a solvent appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the disclosure.

In some cases, protection of certain reactive functionalities may be necessary to achieve some of the above transformations. In general, the need for such protecting groups as well as the conditions necessary to attach and remove such groups will be apparent to those skilled in the art of organic synthesis. An authoritative account describing the many alternatives to the trained practitioner are J. F. W. McOmie, "Protective Groups in Organic Chemistry", Plenum Press, London and New York 1973, in T. W. Greene and P. G. M. Wuts, "Protective Groups in Organic Synthesis", Third edition, Wiley, New York 1999, in "The Peptides"; Volume 3 (editors: E. Gross and J. Meienhofer), Academic Press, London and New York 1981, in "Methoden der organischen Chemie", Houben-Weyl, 4.sup.th edition, Vol. 15/I, Georg Thieme Verlag, Stuttgart 1974, in H.-D. Jakubke and H. Jescheit, "Aminosauren, Peptide, Proteine", Verlag Chemie, Weinheim, Deerfield Beach, and Basel 1982, and/ or in Jochen Lehmann, "Chemie der Kohlenhydrate: Monosaccharide and Derivate", Georg Thieme Verlag, Stuttgart 1974. The protecting groups may be removed at a convenient subsequent stage using methods known from the art.

LC/MS analysis is conducted on an Agilent 1200 HPLC with a quadrupole mass analyzer. LC chromatography used an Agilent XDB-C18 column (4.6×50 mm, 1.8 μm) with a water/acetonitrile (each with 0.2% (v/v) formic acid) gradient at a flow rate of 0.5 mL/min. HRMS analyses are performed at the Duke MS Center. Thin-layer chromatography (TLC) is performed on Sigma-Aldrich plates with a fluorescent indicator. Proton ($^1$H) and carbon ($^{13}$C) NMR spectra are recorded at 300 or 400 MHz and 75 or 100 MHz, respectively, on a Varian Spectrometer. Chemistry shifts (δ) are reported in parts per million (ppm) referenced to $^1$H (TMS at 0.00), $^{13}$C (DMSO at 39.55, CDCl$_3$ at 77.0, and CD$_3$OD at 49.0). Column chromatography is conducted using either silica gel (Silicycle 40-64 μm) or prepacked RediSep columns (Teledyne Isco Inc., Lincoln, Nebr.) on an Isco CombiFlash Rf instrument. All moisture-sensitive reactions are carried out using dry solvents and under a slight pressure of ultra-pure quality argon. Glassware is dried in an oven at 140° C. for at least 12 h prior to use, and then assembled quickly while hot, sealed with rubber septa, and allowed to cool under a stream of argon. Reactions are stirred magnetically using Teflon-coated magnetic stirring bars. Commercially available disposable syringes are used for transferring reagents and solvents.

EXAMPLES

The preparation of the compounds of the disclosure is illustrated further by the following examples, which are not to be construed as limiting the disclosure in scope or spirit to the specific procedures and compounds described in them. In all cases, unless otherwise specified, the column chromatography is performed using a silica gel solid phase.

Example 1

(4S,5S)-methyl 5-(difluoromethyl)-5-methyl-4,5-dihydrooxazole-4-carboxylate (3)

Methyl 2-isocyanoacetate (20.00 g, 201.8 mmol, 1.00 equiv) was added slowly to an ice cold suspension of 1,1-difluoroacetone (22.78 g, 242.20 mmol, 1.20 equiv), CuCl (0.80 g, 8.10 mmol, 0.04 equiv), and TEA (1.41 mL, 10.10 mmol, 0.05 equiv) in anhydrous DCM (330 mL) under argon. The reaction mixture was stirred at 0° C. and gradually warmed to room temperature overnight (20 h). The resulting solution was diluted with DCM (150 mL). The mixture was washed with 10% aqueous ammonia (3×100 mL), water (100 mL), brine (100 mL), and dried (anhydrous Na$_2$SO$_4$). Evaporation of the solvent afforded crude 3 (brown liquid, 35.5 g, yield 91%) which was carried to the next step without further purification. $^1$H NMR (400 MHz, CDCl$_3$): β 1.35 (s, 3H), 1.54 (s, 0.5H), 3.67 (s, 0.5H), 3.74 (s, 3H), 4.47 (s, 0.17H), 4.78 (s, 1H), 5.69 (t, J=110.8 Hz, 1H), 5.88 (s, J=109.2 Hz, 0.17H), 6.94 (s, 1H); $^{13}$C NMR (100 MHz, CDCl$_3$): β 15.36, 43.42, 52.47, 114.18 (t, J=493.6 Hz), 168.72; $^{19}$F NMR (400 MHz, CDCl$_3$): δ −130.00-137.91 (ABq, d, 2F, J$_{HF}$=59 Hz, J$_{FF}$=300 Hz); δ −132.94 (d, J=55.6 Hz), −132.33 (d, J=54.9 Hz), −130.59 (30.6 Hz), −129.81 (J=53.77); LC/MS m/s [M+H]$^+$ 194.1.

Methyl 2-amino-4,4-difluoro-3-hydroxy-3-methylbutanoate hydrochloride (racemic 4a)

To a stirred solution of oxazoline 3 (35.30 g, 182.70 mmol, 1.00 equiv) in methanol (180 mL) kept at room temperature in a water bath under argon was added dropwise concentrated HCl (36 mL). The reaction mixture was stirred at room temperature for 14 h. The resulting solution was concentrated to dryness. The residue was diluted with MTBE (400 mL) and was stirred vigorously for 2 h. The suspension was concentrated to afford crude 4 as a light brown solid $^1$H NMR (400 MHz, CD$_3$OD): β 1.30 (s, 3H), 1.48 (s, 0.5H), 3.85 (s, 0.5H), 3.86 (s, 3H), 4.15 (s, 0.17H), 4.16 (s, 1H), 5.95 (t, J=114.4 Hz, 0.17H), 5.99 (t, J=110.4 Hz, 1H); $^{19}$F NMR (400 MHz, CD$_3$OD): δ −134.25, −135.15 (ABq, d, 2F, J$_{HF}$=59 Hz, J$_{FF}$=301 Hz); $^{13}$C NMR (100 MHz, CD$_3$OD): δ 15.88, 52.64, 55.94, 71.23 (t, J=42.4 Hz), 115.39 (t, J=492 Hz), 166.65; LC/MS m/s [M+H]$^+$ 184.1. The crude product was dissolved to ~55 mL of methanol and MTBE (~270 mL) at room temperature. Then the solution was left in −20° C. for 2 days to give the racemic 4a (17.00 g, yield 42%) as an off-white solid. Alternatively, crude 4 can be recrystallized from hot acetonitrile (~200 mL) to provide racemic 4a in 56% yield. $^1$H (400 MHz, CD$_3$OD) δ 1.30 (s, 3H), 3.87 (s, 3H), 4.16 (s, 1H), 5.99 (t, J=110.4 Hz, 1H); $^{19}$F (400 MHz, CD$_3$OD) δ −134.25, −135.15 (ABq, d, 2F, J$_{HF}$=59 Hz, J$_{FF}$=301 Hz); $^{13}$C (100 MHz, CD$_3$OD) δ 15.89, 52.64, 55.96, 71.23 (t, J=42.5 Hz), 115.40 (t, J=489.9 Hz); $^{19}$F (376 MHz, CDCl$_3$) δ −134.70.

(2S,3S)-methyl 2-amino-4,4-difluoro-3-hydroxy-3-methylbutanoate (−) CSA (5)

To an ice bath cooled solution of racemic 4 (16.70 g, 76.00 mmol, 1.00 equiv) in water (100 mL) was added Na$_2$CO$_3$ (24.17 g, 228.00 mmol, 3.00 equiv) under argon. The reaction mixture was stirred at room temperature for 1 h. Then the resulting solution was extracted with EtOAc (6×100 mL). The combined organic layers were dried over (anhydrous Na$_2$SO$_4$). Evaporation of the solvent afforded the free amine (14.0 g) as a light brown liquid. The free amine (13.50 g, 73.7 mmol, 1.00 equiv) was dissolved in acetone (100 mL) and (1R) (−)-10 camphorsulfonic acid (17.12 g, 73.70 mmol, 1.00 equiv) was added. The mixture was stirred at room temperature overnight. The white solid was filtered and washed with acetone (20 mL) and dried to give the (−) CSA salt 5 (8.40 g, yield 28%). $^1$H NMR (400 MHz, CD$_3$OD): δ 0.83 (s, 3H), 1.09 (s, 3H), 1.30 (s, 3H), 1.37-1.42 (m, 1H), 1.57-1.64 (m, 1H), 1.88 (d, J=18.4 Hz, 1H), 2.00-2.04 (m, 2H), 2.29-2.35 (m, 1H), 2.57-2.61 (m, 1H), 3.00 (dd, J$_1$=208 Hz, J$_2$=14.8 Hz, 1H), 3.86 (s, 3H), 4.21 (s, 1H), 5.98 (t, J=110 Hz, 1H); $^{19}$F NMR (400 MHz, CD$_3$OD): δ −134.23, −135.13 (ABq, d, 2F, J$_{HF}$=59 Hz, J$_{FF}$=301 Hz); $^{13}$C (100 MHz, CD$_3$OD) b 5.82, 18.73, 18.98, 24.32, 26.39, 42.24, 42.61, 46.80, 52.59, 55.99, 58.16, 71.23 (t, J=42.5 Hz), 115.41 (t, J=491 Hz), 166.74, 218.06; $^{19}$F (376 MHz, CDCl$_3$) δ −134.68 (t, J=106 Hz).

Methyl 4-(bromoethynyl)benzoate

To a solution of methyl 4-ethynylbenzoate (10.00 g, 62.5 mmol, 1.0 equiv) in acetone (100 mL) was added NBS (12.24 g, 68.8 mmol, 1.05 equiv) and CF$_3$CO$_2$Ag (0.53 g, 0.31 mmol, 0.05 equiv) at room temperature under argon. The reaction mixture was stirred at room temperature for 2 h. The resulting solution was concentrated to remove acetone. The residue was diluted with water (100 mL) and extracted with EtOAc (3×80 mL). The combined organic layers were washed with water (2×60 mL), brine (60 mL) and dried over (anhydrous Na$_2$SO$_4$). Evaporation of the solvent afforded the crude product which was purified by CombiFlash silica gel chromatography (eluting with EtOAc in hexane 0-10%) to give methyl 4-(bromoethynyl)benzoate as white solid (12.4 g, yield 83%). $^1$H NMR (300 MHz, CDCl$_3$): δ 3.9 (s, 3H), 7.50 (d, J=8.1 Hz, 2H), 7.97 (d, J=6.9 Hz, 2H); $^{13}$C NMR (75 MHz, CDCl$_3$): δ 52.25, 53.36, 79.39, 127.28, 129.47, 129.94, 131.93, 166.34; LC/MS m/s [M+H]$^+$ 240.1

Methyl 4-((4-aminophenyl)buta-1,3-diyn-1-yl)benzoate

Copper (II) acetate (0.45 g, 0.50 mmol, 0.05 equiv) was added at room temperature and under stream of argon to a stirred solution of methyl (4-bromoethylnyl)benzoate (12.0 g, 50.0 mmol, 1.00 equiv) and 4-ethynylbenzenamine (6.20 g, 52.5 mmol, 1.05 equiv) in MeOH (200 mL, degassed by argon). The resulting suspension was diluted with water (400 mL) and stirred 30 min at room temperature. The mixture was filtered and the filtered solid was washed with water (2×200 mL). The solid obtained was dried to afford the crude product (13.5 g) as a yellow solid which was carried on to the next step without further purification. $^1$H NMR (300 MHz, DMSO-d$_6$): δ 3.83 (s, 3H), 5.85 (s, 2H), 6.54 (d, J=8.1 Hz, 2H), 7.25 (d, J=8.4 Hz, 2H), 7.64 (d, J=8.1 Hz, 2H), 7.92 (d, J=8.1 Hz, 2H); $^{13}$C NMR (75 MHz, DMSO-d$_6$): δ 53.04, 71.77, 78.29, 80.49, 86.98, 105.73, 114.28, 126.74, 130.06, 130.32, 132.98, 134.76, 151.64, 166.19; LC/MS m/s [M+H]$^+$ 276.1.

4-((4-Aminophenyl)buta-1,3-diyn-1-yl)benzoic acid (6)

To a solution of crude compound Methyl 4-((4-aminophenyl)buta-1,3-diyn-1-yl)benzoate (13.5 g, 50.0 mmol, 1.00 equiv) in methanol (100 mL) and was added 1N NaOH (100 mL, 100.0 mmol, 2.00 equiv) at room temperature under a stream of argon. The reaction mixture was heated to reflux for 1 h. The solution was diluted with water (100 mL) and acidified with concentrated HCl to pH-3. The precipitate was filtered, washed with water and dried under vacuum to give the crude acid (6) (11.5 g, two steps, yield 88% for two steps), which was carried to next step without purification. $^1$H NMR (300 MHz, DMSO-d$_6$): δ 6.95 (d, J=8.4 Hz, 2H), 7.45 (d, J=8.4 Hz, 2H), 7.66 (d, J=8.4 Hz, 2H), 7.93 (d, J=8.4 Hz, 2H); $^{13}$C NMR (75 MHz, DMSO-d$_6$): δ72.99, 77.22, 81.23, 85.02, 112.00, 118.79, 125.80, 130.24, 131.93, 133.07, 134.64, 144.23, 167.19; LC/MS m/s [M+H]$^+$ 262.1.

(2S,3S)-Methyl 2-(4-((4-aminophenyl)buta-1,3-diyn-1-yl)benzamido)-4,4-difluoro-3-hydroxy-3-methylbutanoate (7)

To a solution of diacetylene carboxylic acid 6 (3.00 g, 12.49 mmol) in anhydrous DMF (25 mL) was added amino ester 5 (5.40 g, 13.11 mmol, 1.05 equiv), EDC.HCl (2.64 g, 13.80 mmol, 1.2 equiv), HOBt (1.87 g, 13.80 mmol, 1.2 equiv) at room temperature under argon. The mixture was cooled to 0° C. and DIEA (8.1 mL, 45.90 mmol, 4.00 equiv) was added. The reaction mixture was stirred at 0° C. for 2 hours, then was allowed to warm to room temperature for 14 hours. The yellow solution was then concentrated to dryness. The residue was treated with water (100 mL), extracted with EtOAc (3×80 mL). The combined extracts were washed with water (80 mL), brine (80 mL), and dried (anhydrous Na$_2$SO$_4$). The crude product was purified by CombiFlash silica gel chromatography (eluting with MeOH in DCM 0-2.5%) to give 7 as a yellow solid (4.23 g, 80%) $^1$H NMR (300 MHz, CD$_3$OD): δ 1.37 (d, J=2.1 Hz, 3H), 3.76 (s, 3H), 4.267 (dd, J=9.3, 19.5 Hz, 1H), 4.42 (dd, J=9.3, 19.8 Hz, 1H), 4.81 (s, 1H), 6.61 (d, J=8.4 Hz, 2H), 7.24 (d, J=8.4 Hz, 2H), 7.56 (d, J=8.1 Hz, 2H), 7.82 (d, J=8.1 Hz, 2H); $^{19}$F NMR (400 MHz, CD$_3$OD): δ −131.06, −137.61 (ABq, d, 2F, J$_{HF}$=60 Hz, J$_{FF}$=30 Hz); $^{13}$C NMR (75 MHz, CD$_3$OD): δ 20.51, 51.69, 70.91, (71.94, 72.19), 76.86, 79.08, 84.73, (85.50, 87.83), 108.34, 114.27, 126.19, 127.20, 127.57, 132.18, 133.60, 133.89, 150.16, 168.18, 170.60; LC/MS m/s [M+H]$^+$ 437.1. HRMS C$_{23}$H$_{20}$F$_2$N$_2$O$_4$ calculated 426.1391 found: 426.1392.

4-((4-Aminophenyl)buta-1,3-diyn-1-yl)-N-((2S,3S)-4,4-difluoro-3-hydroxy-1-(hydroxyamino)-3-methyl-1-oxobutan-2-yl)benzamide (8)

To an ice-cold solution of 7 (4.00 g, 9.4 mmol) dissolved in anhydrous MeOH (15 mL) and THF (15 mL) was added hydroxylamine hydrochloride (3.27 g, 46.9 mmol, 5.0 equiv) followed by 25% sodium methoxide in methanol solution (16.0 mL, 70.50 mmol, 7.5 equiv). The reaction mixture was stirred under argon and at 0° C. for 2 h, then allowed to warm to ambient temperature with stirring continued overnight (14 h). The resulting yellow suspension was condensed to dryness with a rotary evaporator, and the residue obtained was treated water (200 mL) and saturated NH$_4$Cl (80 mL), and extracted with EtOAc (3×100 mL). The combined extracts were washed with water (80 mL), brine (80 mL), and dried over anhydrous Na$_2$SO$_4$. Evaporation of the solvent afforded the crude product, which was purified by CombiFlash silica gel chromatography (eluting with 0-5% MeOH in DCM) to afford the title compound as a yellow solid 8: (3.29 g, 82% yield), $^1$H NMR (300 MHz, CD$_3$OD): δ 1.36 (s, 3H), 4.73 (s, 1H), 5.80 (t, J=112.2 Hz, 1H), 6.61 (d, J=8.7 Hz, 2H), 7.24 (d, J=8.7 Hz, 2H), 7.57 (d, J=8.1 Hz, 2H), 7.82 (d, J=8.4 Hz, 2H); $^{19}$F NMR (400 MHz, CD$_3$OD): δ −130.00, −137.91 (ABq, d, 2F, J$_{HF}$=60 Hz, J$_{FF}$=300 Hz); $^{13}$C NMR (75 MHz, CD$_3$OD): δ 16.54, 54.87, 70.81, (72.60, 72.90, 73.19), 76.83, 78.97, 84.68, 108.36, (112.72, 115.96, 119.23), 114.26, 126.27, 127.53, 132.16, 133.47, 133.84, 150.16, 166.52, 167.51; LC/MS m/s [M+H]$^+$ 428.2. HRMS C$_{22}$H$_{19}$F$_2$N$_3$O$_4$ calculated 427.1344 found 427.1346.

Example 2

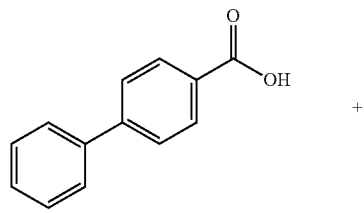

+

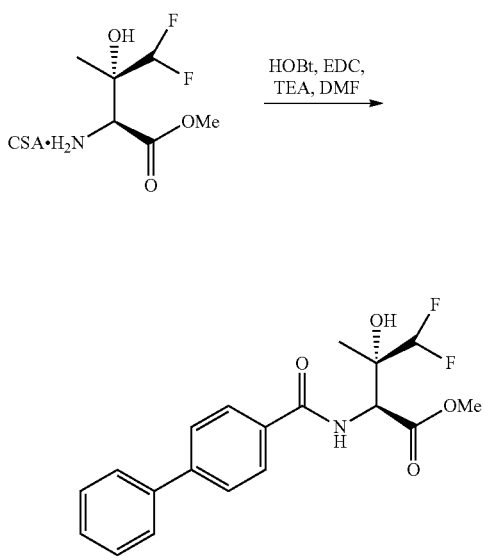

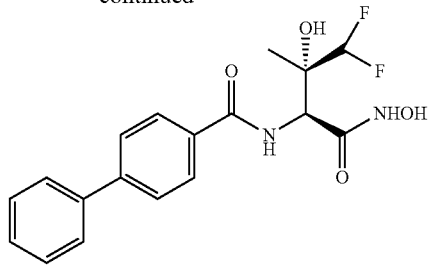

Example 2

A solution of the methyl ester (4.3 g, 11.9 mmol) in MeOH (120 mL) was cooled in an ice-NaCl bath. Aqueous hydroxylamine (15 mL, 240 mmol, 20 eq.) and LiOH H$_2$O (1.2 g, 29 mmol, 2.4 eq.) were added in sequence. The reaction mixture was stirred in the ice bath until analysis by TLC (50% EtOAc in hexanes) indicated complete consumption of starting ester. The reaction mixture was diluted with H$_2$O (300 mL) and saturated aqueous NH$_4$Cl was added to pH 7-8 (universal indicating pH paper). MeOH was removed by rotary evaporation and the suspension was aged at room temperature for 2 h. Insolubles were removed by vacuum filtration. The filter cake was washed with H$_2$O (100 mL) and dried in vacuo giving the pure product (N-((2S, 3S)-4,4-difluoro-3-hydroxy-1-(hydroxyamino)-3-methyl-1-oxobutan-2-yl)-[1,1'-biphenyl]-4-carboxamide) as a free-flowing pale cream colored solid (3.4 g, 78%). $^1$H NMR (400 MHz, DMSO-d$_6$): δ 10.9 (bs, 1H), 9.04 (bs, 1H), 8.07 (d, J=9.2 Hz, 1H), 7.98 (d, J=7.2 Hz, 2H), 7.80 (d, J=7.2 Hz, 2H), 7.74 (d, J=7.2 Hz, 2H), 7.51 (t, J=7.2 Hz, 2H), 7.43 (m, 1H), 5.87 (t, J=56.0 Hz, 1H), 4.60 (d, J=9.2 Hz, 1H), 1.20 (s, 3H). $^{19}$F NMR (400 MHz, DMSO-d$_6$): δ=−128.0 (ABq 1F, J$_{HF}$=58 Hz, J$_{FF}$=280 Hz), −135.0 (ABq 1F, J$_{HF}$=60 Hz, J$_{FF}$=280 Hz). ESIMS=363 (M−H).

Triethylamine (5.3 mL, 38 mmol, 3.2 eq.) was added in one portion at room temperature to a suspension of the acid (2.4 g, 12.4 mmol, 1.04 eq.), HOBt (2.3 g, 15 mmol, 1.2 eq.), the amine CSA salt (4.92 g, 11.9 mmol.), and EDC (2.9 g, 15 mmol, 1.2 eq.) in anhydrous DMF (33 mL). The reaction mixture was stirred overnight then diluted into brine (700 mL). The resulting suspension was stirred for 1 h then insolubles were removed at the vacuum. The filter cake was washed with 1N HCl (100 mL), H$_2$O (100 mL) and dried in vacuo over the weekend. Analysis of the filter cake (white powdery solid, 4.3 g, ~quant.) by LCMS indicated the desired product as the sole product present. The amide was used in the next step without further purification.

Example 3

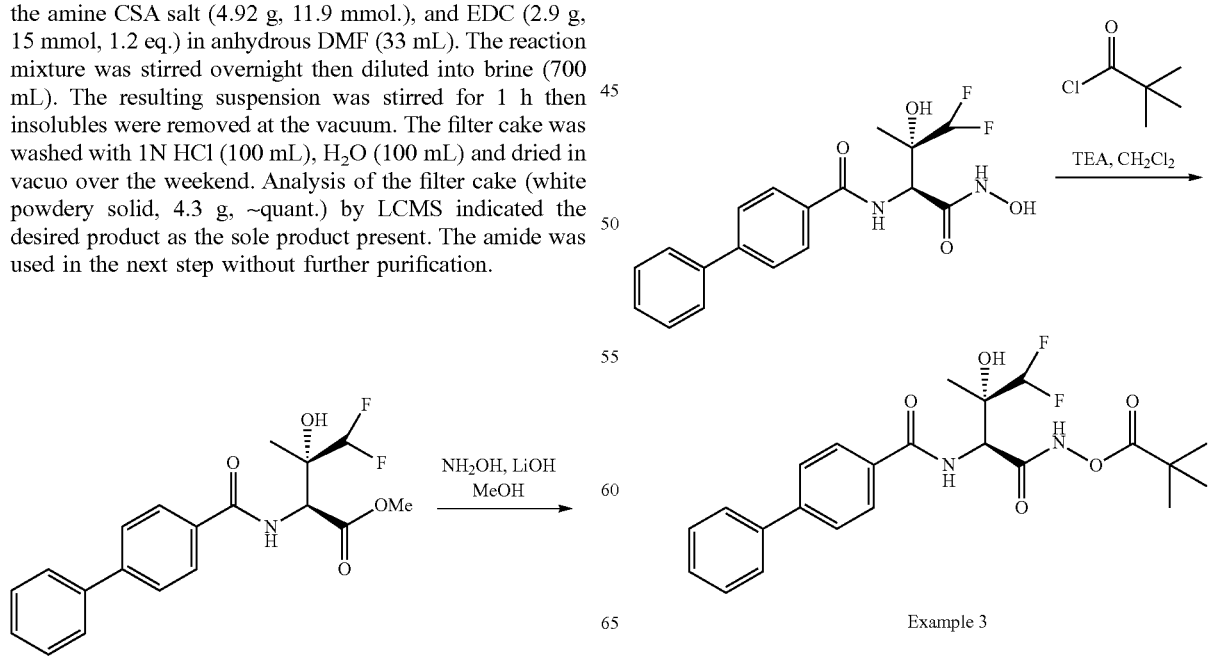

Example 3

A solution of pivaloyl chloride (1.1 mL, 9.3 mmol, 1.01 eq.) in CH$_2$Cl$_2$ (12 mL) was added dropwise at room temperature to a solution of the hydroxamic acid (3.5 g, 9.2 mmol) and triethylamine (2.0 mL, 14.3 mmol, 1.6 eq.) in CH$_2$Cl$_2$ (85 mL). The reaction mixture was stirred overnight at room temperature. The mixture was washed with H$_2$O (100 mL), brine (100 mL), and dried (Na$_2$SO$_4$). The drying agent was removed by filtration. Silica gel (~5 g) was added to the filtrate and the mixture was concentrated to dryness under reduced pressure. Flash column chromatography (hexane:EtOAc (2:1)) gave the product (N-((2S,3S)-4,4-difluoro-3-hydroxy-3-methyl-1-oxo-1-((pivaloyloxy)amino)butan-2-yl)-[1,1'-biphenyl]-4-carboxamide) as a white free-flowing solid (2.15 g, 52%). $^1$H NMR (400 MHz, DMSO-d$_6$): δ 12.1 (bs, 1H), 8.11 (d, J=9.2 Hz, 1H), 7.98 (d, J=7.2 Hz, 2H), 7.82 (d, J=7.2 Hz, 2H), 7.51 (t, J=7.2 Hz, 2H), 7.43 (m, 1H), 5.96 (t, J=55.6 Hz, 1H), 4.75 (d, J=9.2 Hz, 1H), 1.93 (d, J=1.2 Hz, 1H), 1.34 (s, 3H), 1.23 (s, 9H). $^{19}$F NMR (400 MHz, DMSO-d$_6$): δ=−128.6 (ABq 1F, J$_{HF}$=58 Hz, J$_{FF}$=295 Hz), −135.4 (ABq 1F, J$_{HF}$=60 Hz, J$_{FF}$=295 Hz). ESIMS (m/z)=447 (M−H).

Example 4

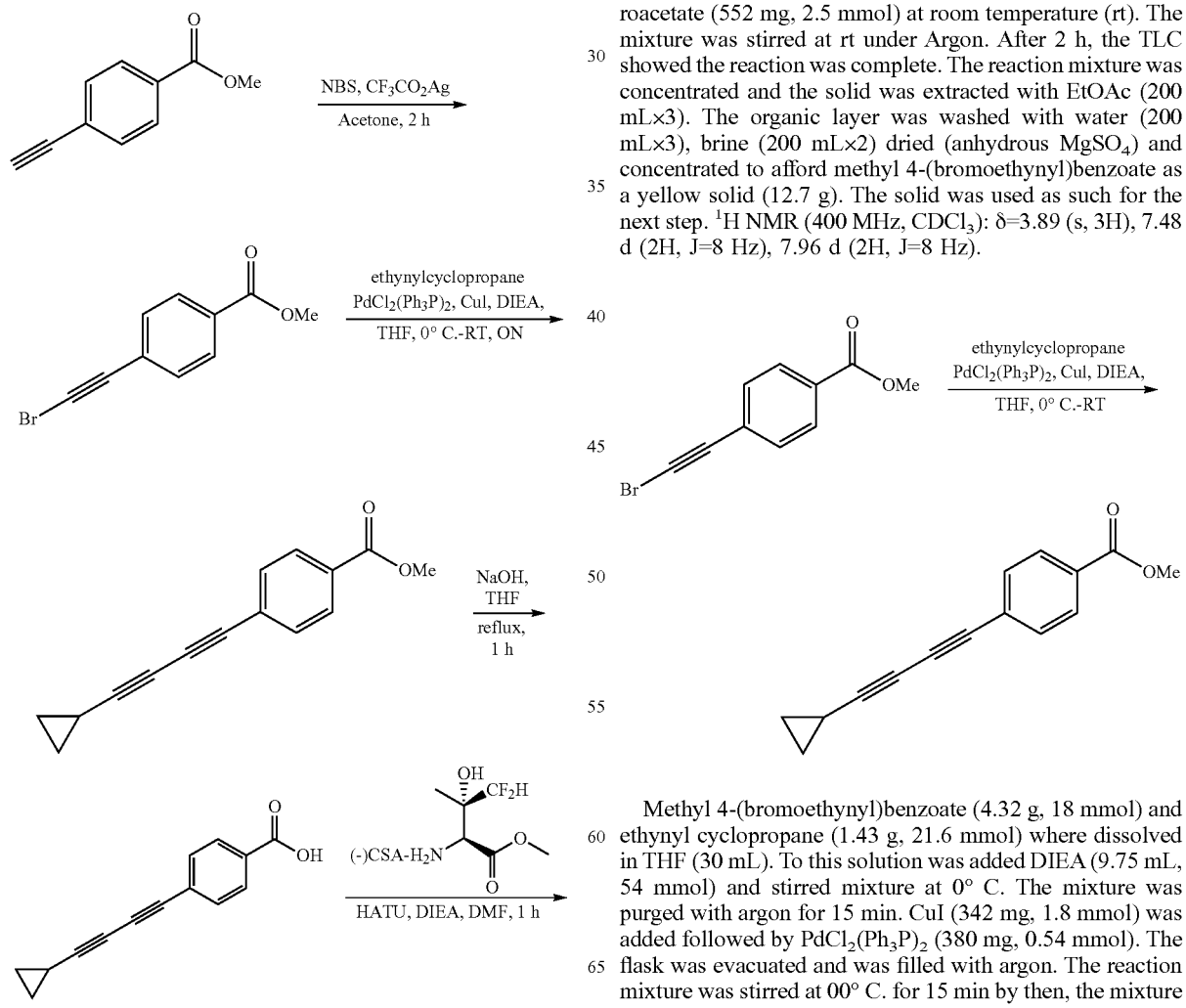

Example 4

To a stirred solution of methyl 4-ethynylbenzoate (10 g, 62.5 mmol) in acetone (100 mL) was added N-bromosuccinimide (12.25 g, 68.25 mmol) followed by silver trifluoroacetate (552 mg, 2.5 mmol) at room temperature (rt). The mixture was stirred at rt under Argon. After 2 h, the TLC showed the reaction was complete. The reaction mixture was concentrated and the solid was extracted with EtOAc (200 mL×3). The organic layer was washed with water (200 mL×3), brine (200 mL×2) dried (anhydrous MgSO$_4$) and concentrated to afford methyl 4-(bromoethynyl)benzoate as a yellow solid (12.7 g). The solid was used as such for the next step. $^1$H NMR (400 MHz, CDCl$_3$): δ=3.89 (s, 3H), 7.48 d (2H, J=8 Hz), 7.96 d (2H, J=8 Hz).

Methyl 4-(bromoethynyl)benzoate (4.32 g, 18 mmol) and ethynyl cyclopropane (1.43 g, 21.6 mmol) where dissolved in THF (30 mL). To this solution was added DIEA (9.75 mL, 54 mmol) and stirred mixture at 0° C. The mixture was purged with argon for 15 min. CuI (342 mg, 1.8 mmol) was added followed by PdCl$_2$(Ph$_3$P)$_2$ (380 mg, 0.54 mmol). The flask was evacuated and was filled with argon. The reaction mixture was stirred at 00° C. for 15 min by then, the mixture became a suspensions. The mixture was stirred overnight.

The reaction mixture was extracted with EtOAc (100 mL×3), washed with water (200 mL×3), brine (200 mL×2), dried (anhydrous Na$_2$SO$_4$) and concentrated to get a yellow solid. TLC showed two new spots. The crude product was purified by flash chromatography (80 g silica cartridge, Hexanes-EtOAc (0-50%) to furnish methyl 4-(cyclopropylbuta-1,3-diyn-1-yl)benzoate (2.4 g). $^1$H NMR (400 MHz, CDCl$_3$): δ=0.83-0.89 (m, 4H), 1.38-1.42 (m, 1H) 3.89 (s, 3H), 7.48 d (2H, J=8 Hz), 7.96 d (2H, J=8 Hz).

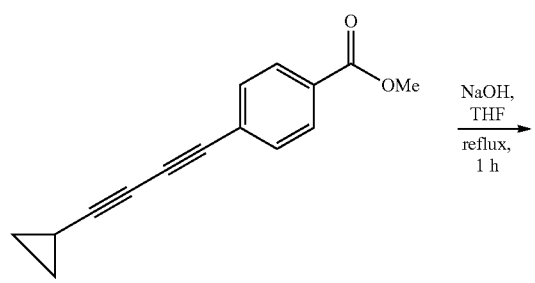

Methyl 4-(cyclopropylbuta-1,3-diyn-1-yl)benzoate (2.4 g, 10.7 mmol.) was dissolved in THF (125 mL). To this solution was added 2N NaOH solution (16.5 mL, 33 mmol.). The mixture was heated at reflux for 1 h, allowed to cool at RT. The pH of the solution was adjusted to ~4 using 1N HCl. The majority of the solvent was removed in vacuum. The resulting solid was extracted with EtOAc (100 mL×3). The organic layer was washed with water (200 mL×3), brine (100 mL×3), dried (anhydrous Na$_2$SO$_4$) and concentrated to give 4-(cyclopropylbuta-1,3-diyn-1-yl)benzoic acid as a yellowish white solid (2.2 g). $^1$H NMR (400 MHz, CDCl$_3$): δ=0.74-0.78 (m, 2H), 0.89-0.92 (m, 2H), 1.42-1.48 (m, 1H), 7.51 d (2H, J=8 Hz), 7.96 d (2H, J=8 Hz).

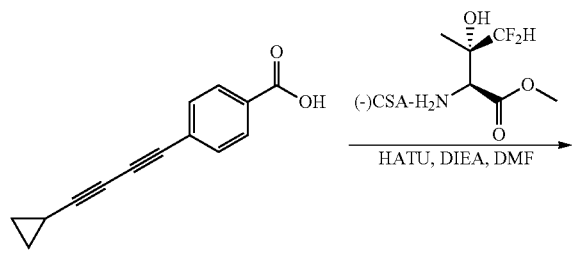

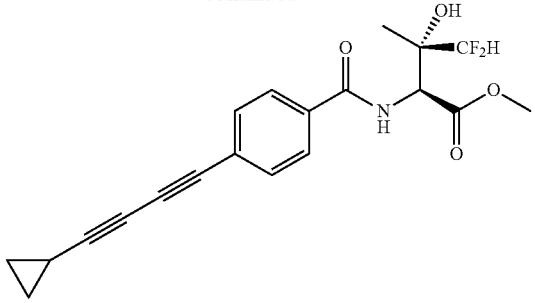

To a solution of 4-(cyclopropylbuta-1,3-diyn-1-yl)benzoic acid (2.1 g, 10 mmol) in anhydrous DMF (40 mL) was added, HATU (4.93 g, 13 mmol), The mixture was cooled to 00° C. and was added DIEA (5.2 mL 30 mmol). The reaction mixture was stirred at 0° C. for 5 min and was added methyl (2S,3S)-2-amino-4,4-difluoro-3-hydroxy-3-methylbutanoate (−)camphor sulfonic acid salt (4.15 g, 10 mmol). The mixture was stirred at 0° C. for 1 h and was allowed to warm to rt. After the reaction is complete, by TLC and LCMS, the mixture was concentrated and the residue was treated with water. The residue was extracted with EtOAc (100 mL×4). The organic layer was washed with water (200 mL×3), brine (200 mL×2), dried (anhydrous Na$_2$SO$_4$) and concentrated. The crude product was purified by flash column chromatography DCM-Methanol (0-3%) to furnish methyl (2S,3S)-2-(4-(cyclopropylbuta-1,3-diyn-1-yl)benzamido)-4,4-difluoro-3-hydroxy-3-methylbutanoate as a yellow solid (3.6 g). $^1$H NMR (400 MHz CDCl$_3$): δ=0.81-0.91 (m, 4H), 1.35 (s, 3H), 1.38-1.45 (m, 1H), 3.55 (s, 1H), 3.81 (s, 3H), 5.01 (d, J=9 Hz), 5.74 (t, J=56 Hz), 6.88 (d, J=9 Hz), 7.51 (d, 2H, J=8 Hz), 7.72 d (2H, J=8 Hz). $^{19}$F NMR (400 MHz, CD$_3$OD): δ=−137.15 (ABq 1F, J$_{HF}$=60 Hz, J$_{FF}$=301 Hz), −131.1 (ABq 1F, J$_{HF}$=60 Hz, J$_{FF}$=301 Hz). LCMS (m/z)= 376 M+H).

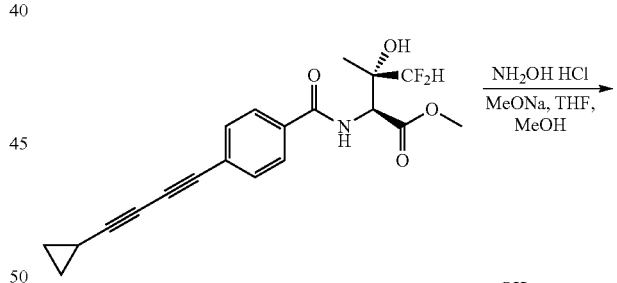

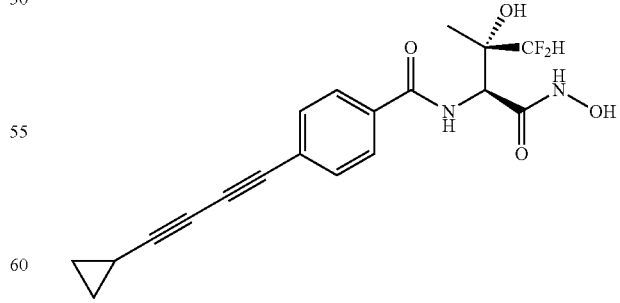

Example 4

To a solution of methyl (2S,3S)-2-(4-(cyclopropylbuta-1,3-diyn-1-yl)benzamido)-4,4-difluoro-3-hydroxy-3-methylbutanoate (3.75 g, 10 mmol) in methanol (100 mL) was added 50% hydroxyl amine solution (13.3 mL, 200 mmol) and LiOH (820 mg, 20 mmol) at −10 OC. The mixture was stirred at that temperature for 2 h and was then warmed to rt. The mixture was further stirred ON. The TLC and LCMS and 1H NMR showed complete conversion. The mixture was concentrated. To the residue was added ammonium chloride to bring the PH to 7. The mixture was extracted with EtOAc (100 mL×4). The organic layer was washed with water (200 mL×3), brine (200 mL×2), dried (anhydrous $Na_2SO_4$) and concentrated to get a yellow solid. This solid was purified by flash column chromatography using DCM-MeOH (0-5%) to afford 4-(cyclopropylbuta-1,3-diyn-1-yl)-N-((2S,3S)-4,4-difluoro-3-hydroxy-1-(hydroxyamino)-3-methyl-1-oxobutan-2-yl)benzamide as a pale yellow solid (3.3 g). $^1$H NMR (400 MHz, $CD_3OD$): δ=0.73-0.78 (m, 2H), 0.86-0.92 (m, 2H), 1.33 (s, 3H), 1.40-1.49 (m, 1H), 4.70 (s, 1H), 5.77 (t, J=56 Hz), 7.53 (d, 2H, J=8 Hz), 7.79 d (2H, J=8 Hz). $^{13}$C NMR (100 MHz, $CD_3OD$): δ=−0.60, 8.2, 16.28, 54.62, 59.36, 72.24, 72.63, 76.51, 88.83, 115.71, 125.78, 127.27, 132.15, 133.32, 166.25, 167.23. $^{19}$F NMR (400 MHz, $CD_3OD$): δ=−138.0 (ABq 1F, $J_{HF}$=60 Hz, $J_{FF}$=302 Hz), −130.0 (ABq 1F, $J_{HF}$=60 Hz, $J_{FF}$=301 Hz). LCMS (m/z)=375 (M−H).

Examples 5-55

The following compounds are prepared substantially according to the procedures described above:

| Example No. | Compound Structure | Chemical Name |
|---|---|---|
| 5 | 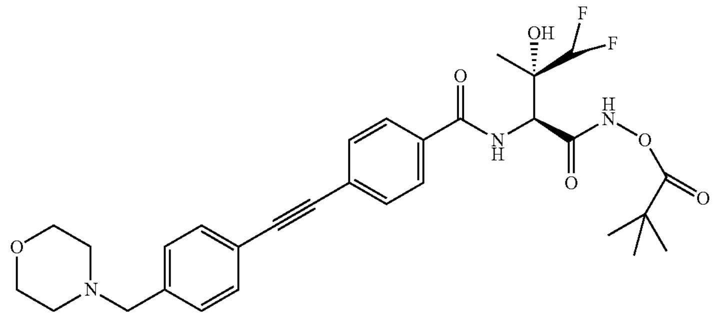 [SMILES: CC(C)(C)C(=O)ONC(=O)[C@@H](NC(=O)c1ccc(C#Cc2ccc(CN3CCOCC3)cc2)cc1)[C@](C)(O)C(F)F] | N-((2S,3S)-4,4-difluoro-3-hydroxy-3-methyl-1-oxo-1-((pivaloyloxy)amino)butan-2-yl)-4-((4-(morpholinomethyl)phenyl)-ethynyl)benzamide |
| 6 | 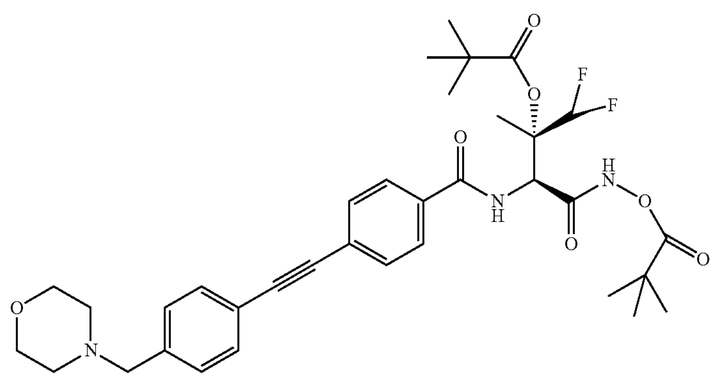 [SMILES: CC(C)(C)C(=O)ONC(=O)[C@@H](NC(=O)c1ccc(C#Cc2ccc(CN3CCOCC3)cc2)cc1)[C@](C)(OC(=O)C(C)(C)C)C(F)F] | (2S,3S)-1,1-difluoro-2-methyl-3-(4-((4-(morpholinomethyl)phenyl)ethynyl)benzamido)-4-oxo-4-((pivaloyloxy)amino)butan-2-yl pivalate |
| 7 | 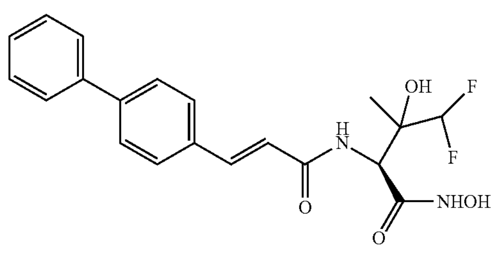 | (2S)-2-((E)-3-([1,1'-biphenyl]-4-yl)acrylamido)-4,4-difluoro-N,3-dihydroxy-3-methylbutanamide |
| 8 | 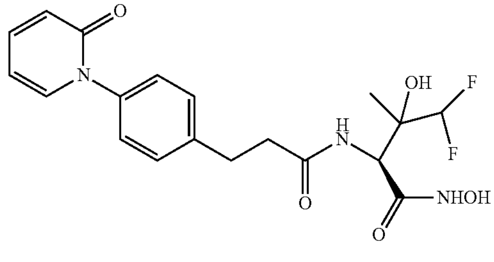 | (2S)-4,4-difluoro-N,3-dihydroxy-3-methyl-2-(3-(4-(2-oxopyridin-1(2H)-yl)phenyl)propanamido)butanamide |

-continued

| Example No. | Compound Structure | Chemical Name |
|---|---|---|
| 9 | 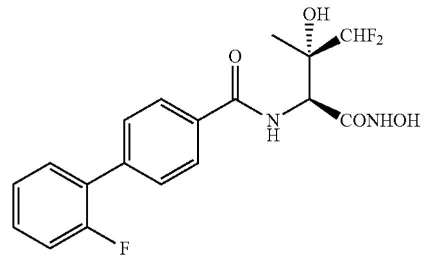 | N-((2S,3S)-4,4-difluoro-3-hydroxy-1-(hydroxyamino)-3-methyl-1-oxobutan-2-yl)-2'-fluoro-[1,1'-biphenyl]-4-carboxamide |
| 10 | 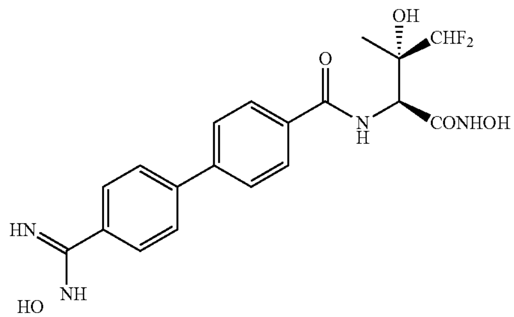 | N-((2S,3S)-4,4-difluoro-3-hydroxy-1-(hydroxyamino)-3-methyl-1-oxobutan-2-yl)-4'-(N-hydroxycarbamimidoyl)-[1,1'-biphenyl]-4-carboxamide |
| 11 | 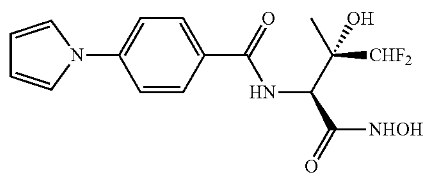 | N-((2S,3S)-4,4-difluoro-3-hydroxy-1-(hydroxyamino)-3-methyl-1-oxobutan-2-yl)-4-(1H-pyrrol-1-yl)benzamide |
| 12 | 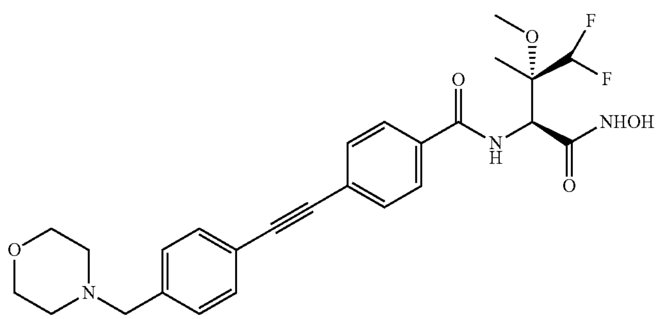 | N-((2S,3S)-4,4-difluoro-1-(hydroxyamino)-3-methoxy-3-methyl-1-oxobutan-2-yl)-4-((4-(morpholinomethyl)phenyl)ethynyl)-benzamide |
| 13 | 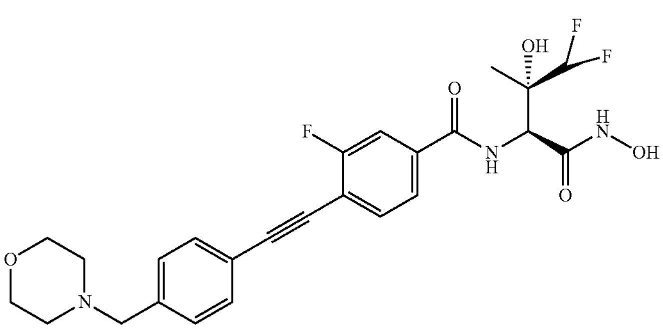 [SMILES: C[C@@](O)(C(F)F)[C@H](NC(=O)c1ccc(C#Cc2ccc(CN3CCOCC3)cc2)c(F)c1)C(=O)NO] | N-((2S,3S)-4,4-difluoro-3-hydroxy-1-(hydroxyamino)-3-methyl-1-oxobutan-2-yl)-3-fluoro-4-((4-(morpholinomethyl)phenyl)-ethynyl)benzamide |
| 14 | 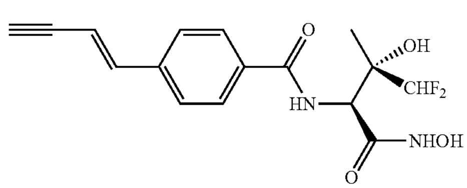 | 4-((E)-but-1-en-3-yn-1-yl)-N-((2S,3S)-4,4-difluoro-3-hydroxy-1-(hydroxyamino)-3-methyl-1-oxobutan-2-yl)benzamide |

-continued

| Example No. | Compound Structure | Chemical Name |
|---|---|---|
| 15 | 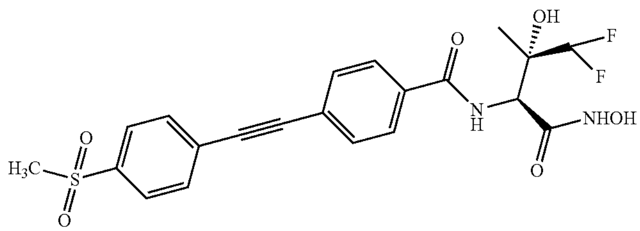 | N-((2S,3S)-4,4-difluoro-3-hydroxy-1-(hydroxyamino)-3-methyl-1-oxobutan-2-yl)-4-((4-(methyl-sulfonyl)phenyl)ethynyl)-benzamide |
| 16 | 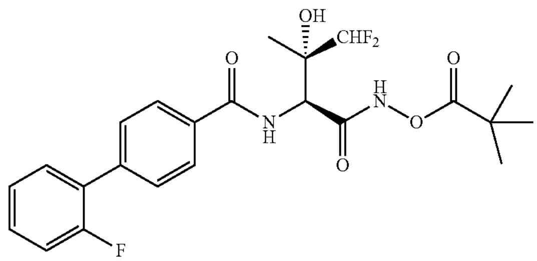 [SMILES: CC(C)(C)C(=O)ONC(=O)[C@@H](NC(=O)c1ccc(-c2ccccc2F)cc1)[C@](C)(O)C(F)F] | N-((2S,3S)-4,4-difluoro-3-hydroxy-3-methyl-1-oxo-1-((pivaloyloxy)ami-no)butan-2-yl)-2'-fluoro-[1,1'-biphenyl]-4-carboxamide |
| 17 | 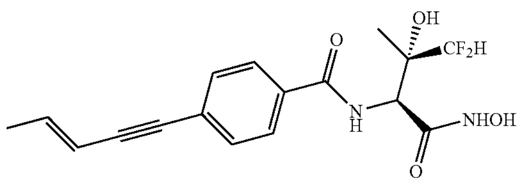 | N-((2S,3S)-4,4-difluoro-3-hydroxy-1-(hydroxyamino)-3-methyl-1-oxobutan-2-yl)-4-((E)-pent-3-en-1-yn-1-yl)benzamide |
| 18 | 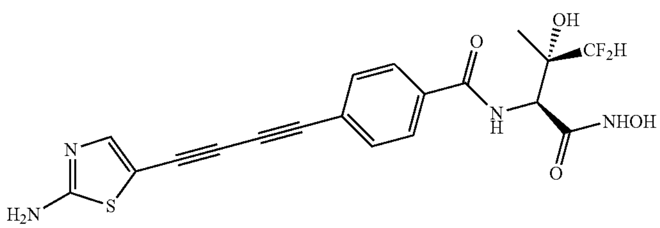 | 4-((2-aminothiazol-5-yl)buta-1,3-diyn-1-yl)-N-((2S,3S)-4,4-difluoro-3-hydroxy-1-(hydroxyamino)-3-methyl-1-oxobutan-2-yl)benzamide |
| 19 | 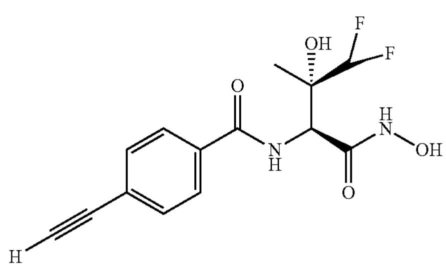 [SMILES: C#Cc1ccc(C(=O)N[C@H](C(=O)NO)[C@](C)(O)C(F)F)cc1] | N-((2S,3S)-4,4-difluoro-3-hydroxy-1-(hydroxyamino)-3-methyl-1-oxobutan-2-yl)-4-ethynylbenzamide |
| 20 | 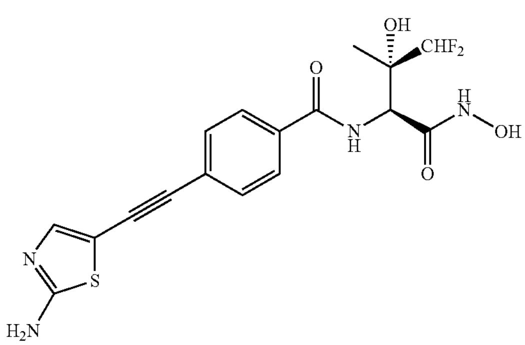 [SMILES: C[C@@](O)(C(F)F)[C@H](NC(=O)c1ccc(C#Cc2cnc(N)s2)cc1)C(=O)NO] | 4-((2-aminothiazol-5-yl)ethynyl)-N-((2S,3S)-4,4-difluoro-3-hydroxy-1-(hydroxyamino)-3-methyl-1-oxobutan-2-yl)benzamide |

-continued

| Example No. | Compound Structure | Chemical Name |
|---|---|---|
| 21 | 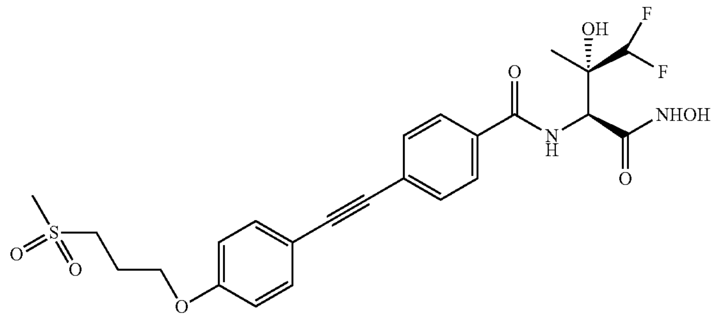 | N-((2S,3S)-4,4-difluoro-3-hydroxy-1-(hydroxyamino)-3-methyl-1-oxobutan-2-yl)-4-((4-(3-(methyl-sulfonyl)propoxy)phenyl)-ethynyl)benzamide |
| 22 | 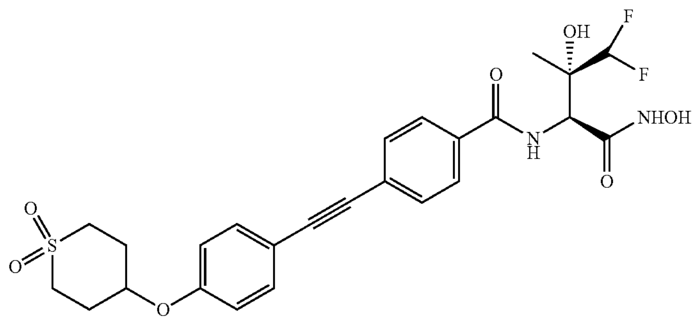 | N-((2S,3S)-4,4-difluoro-3-hydroxy-1-(hydroxyamino)-3-methyl-1-oxobutan-2-yl)-4-((4-((1,1-dioxidotetrahydro-2H-thiopyran-4-yl)oxy)phenyl)ethynyl)benzamide |
| 23 | 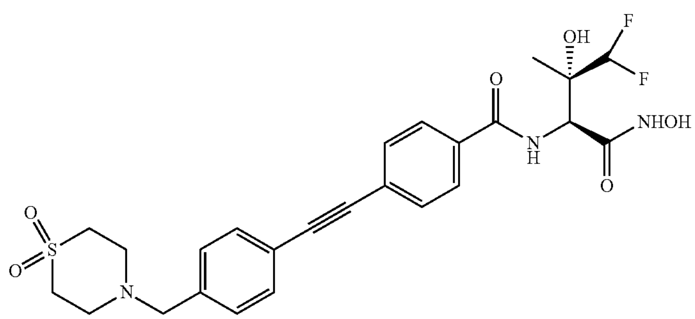 | N-((2S,3S)-4,4-difluoro-3-hydroxy-1-(hydroxyamino)-3-methyl-1-oxobutan-2-yl)-4-((4-((1,1-dioxidothiomorpholino)methyl)-phenyl)ethynyl)benzamide |
| 24 | 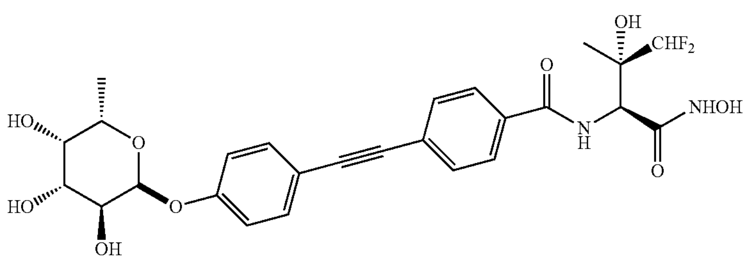 | N-((2S,3S)-4,4-difluoro-3-hydroxy-1-(hydroxyamino)-3-methyl-1-oxobutan-2-yl)-4-((4-(((3S,4R,5S,6S)-3,4,5-trihydroxy-6-methyltetrahydro-2H-pyran-2-yl)oxy)phenyl)ethynyl)benzamide |
| 25 | 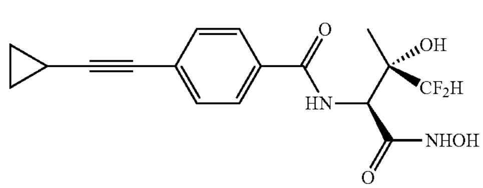 | 4-(cyclopropylethynyl)-N-((2S,3S)-4,4-difluoro-3-hydroxy-1-(hydroxyamino)-3-methyl-1-oxobutan-2-yl)benzamide |

-continued

| Example No. | Compound Structure | Chemical Name |
|---|---|---|
| 26 | 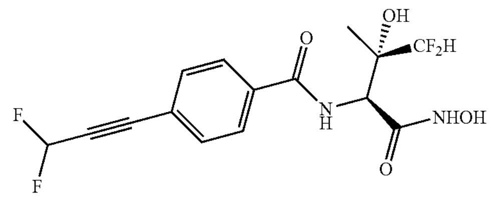 | N-((2S,3S)-4,4-difluoro-3-hydroxy-1-(hydroxyamino)-3-methyl-1-oxobutan-2-yl)-4-(3,3-difluoroprop-1-yn-1-yl)benzamide |
| 27 | 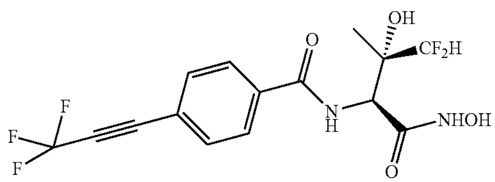 | N-((2S,3S)-4,4-difluoro-3-hydroxy-1-(hydroxyamino)-3-methyl-1-oxobutan-2-yl)-4-(3,3,3-trifluoroprop-1-yn-1-yl)benzamide |
| 28 | 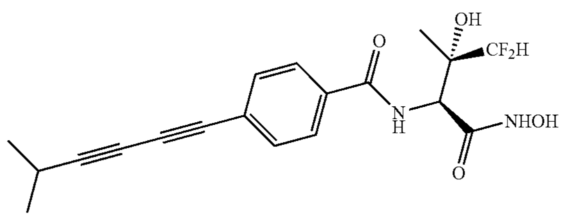 | N-((2S,3S)-4,4-difluoro-3-hydroxy-1-(hydroxyamino)-3-methyl-1-oxobutan-2-yl)-4-(5-methylhexa-1,3-diyn-1-yl)benzamide |
| 29 | 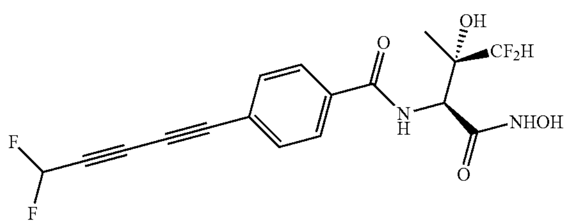 | N-((2S,3S)-4,4-difluoro-3-hydroxy-1-(hydroxyamino)-3-methyl-1-oxobutan-2-yl)-4-(5,5-difluoropenta-1,3-diyn-1-yl)benzamide |
| 30 | 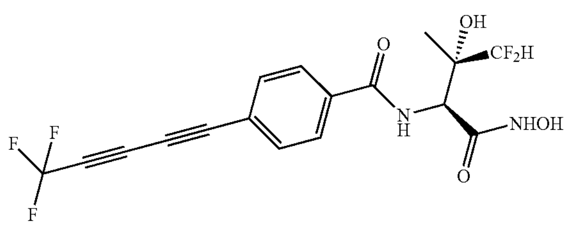 | N-((2S,3S)-4,4-difluoro-3-hydroxy-1-(hydroxyamino)-3-methyl-1-oxobutan-2-yl)-4-(5,5,5-trifluoropenta-1,3-diyn-1-yl)benzamide |
| 31 | 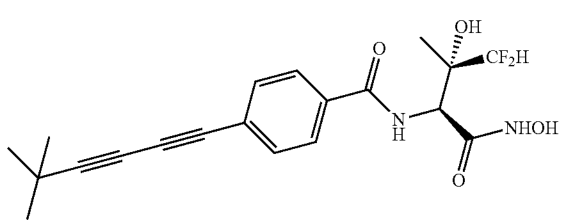 | N-((2S,3S)-4,4-difluoro-3-hydroxy-1-(hydroxyamino)-3-methyl-1-oxobutan-2-yl)-4-(5,5-dimethylhexa-1,3-diyn-1-yl)benzamide |
| 32 | 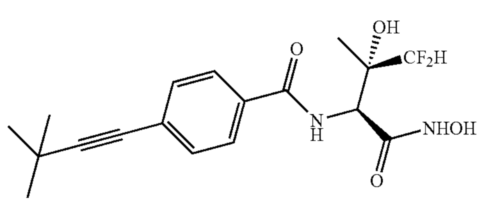 | N-((2S,3S)-4,4-difluoro-3-hydroxy-1-(hydroxyamino)-3-methyl-1-oxobutan-2-yl)-4-(3,3-dimethylbut-1-yn-1-yl)benzamide |

| Example No. | Compound Structure | Chemical Name |
| --- | --- | --- |
| 33 | 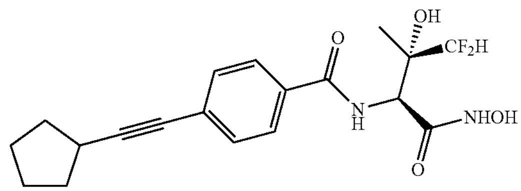 | 4-(cyclopentylethynyl)-N-((2S,3S)-4,4-difluoro-3-hydroxy-1-(hydroxyamino)-3-methyl-1-oxobutan-2-yl)benzamide |
| 34 | 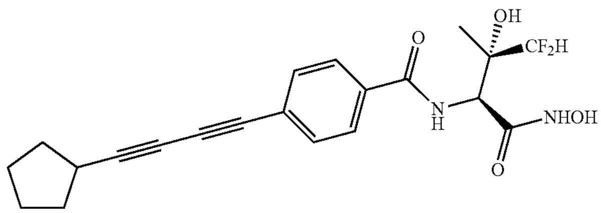 | 4-(cyclopentylbuta-1,3-diyn-1-yl)-N-((2S,3S)-4,4-difluoro-3-hydroxy-1-(hydroxyamino)-3-methyl-1-oxobutan-2-yl)benzamide |
| 35 | 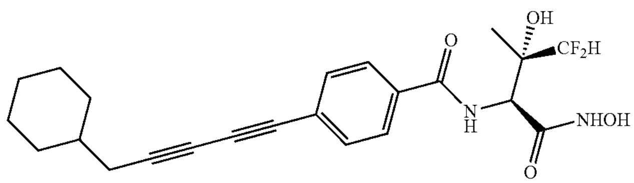 | 4-(5-cyclohexylpenta-1,3-diyn-1-yl)-N-((2S,3S)-4,4-difluoro-3-hydroxy-1-(hydroxyamino)-3-methyl-1-oxobutan-2-yl)benzamide |
| 36 | 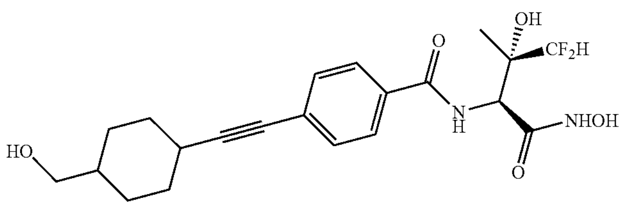 | N-((2S,3S)-4,4-difluoro-3-hydroxy-1-(hydroxyamino)-3-methyl-1-oxobutan-2-yl)-4-((4-(hydroxymethyl)cyclohexyl)ethynyl)-benzamide |
| 37 | 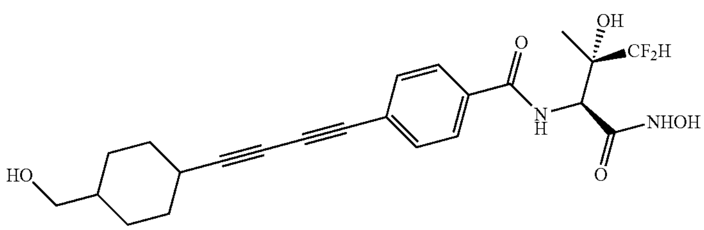 | N-((2S,3S)-4,4-difluoro-3-hydroxy-1-(hydroxyamino)-3-methyl-1-oxobutan-2-yl)-4-((4-(hydroxymethyl)cyclohexyl)buta-1,3-diyn-1-yl)benzamide |
| 38 | 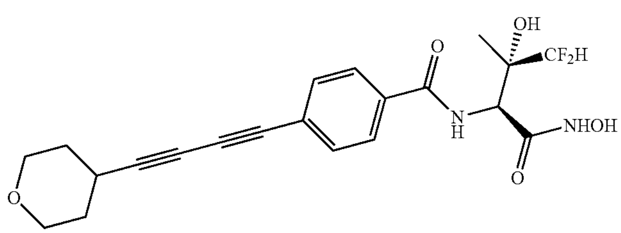 | N-((2S,3S)-4,4-difluoro-3-hydroxy-1-(hydroxyamino)-3-methyl-1-oxobutan-2-yl)-4-((tetrahydro-2H-pyran-4-yl)buta-1,3-diyn-1-yl)benzamide |
| 39 | 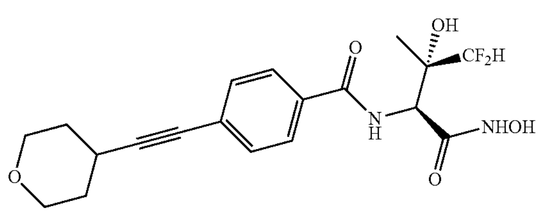 | N-((2S,3S)-4,4-difluoro-3-hydroxy-1-(hydroxyamino)-3-methyl-1-oxobutan-2-yl)-4-((tetrahydro-2H-pyran-4-yl)ethynyl)benzamide |

-continued

| Example No. | Compound Structure | Chemical Name |
|---|---|---|
| 40 | 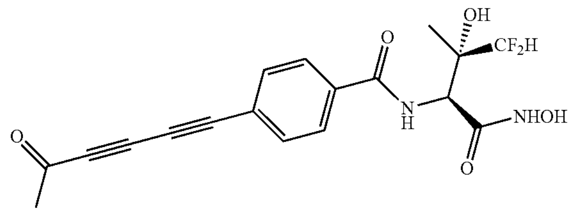 | N-((2S,3S)-4,4-difluoro-3-hydroxy-1-(hydroxyamino)-3-methyl-1-oxobutan-2-yl)-4-(5-oxohexa-1,3-diyn-1-yl)benzamide |
| 41 | 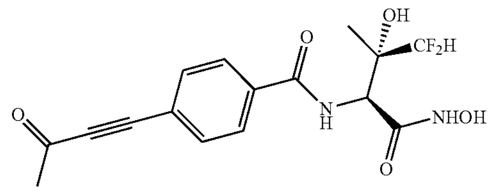 | N-((2S,3S)-4,4-difluoro-3-hydroxy-1-(hydroxyamino)-3-methyl-1-oxobutan-2-yl)-4-(3-oxobut-1-yn-1-yl)benzamide |
| 42 | 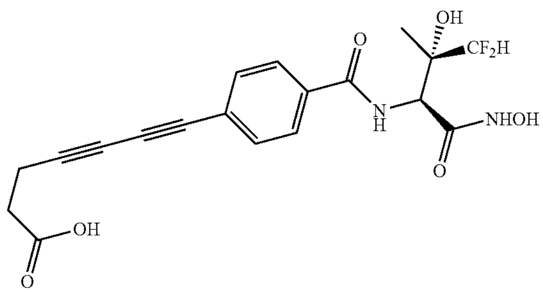 | 7-(4-(((2S,3S)-4,4-difluoro-3-hydroxy-1-(hydroxyamino)-3-methyl-1-oxobutan-2-yl)carbamoyl)phenyl)hepta-4,6-diynoic acid |
| 43 | 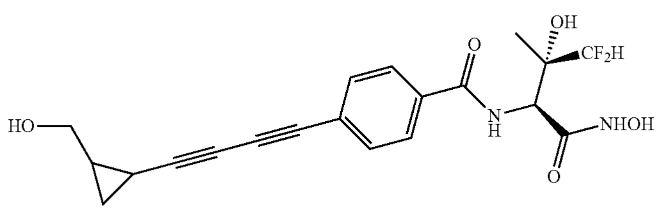 | N-((2S,3S)-4,4-difluoro-3-hydroxy-1-(hydroxyamino)-3-methyl-1-oxobutan-2-yl)-4-((2-(hydroxymethyl)cyclopropyl)buta-1,3-diyn-1-yl)benzamide |
| 44 | 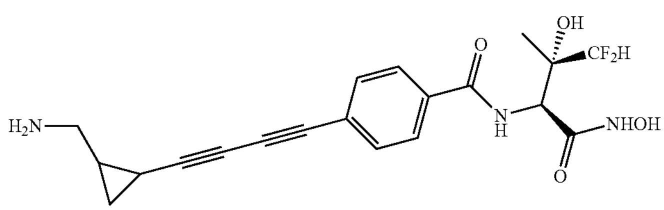 | 4-((2-(aminomethyl)cyclopropyl)buta-1,3-diyn-1-yl)-N-((2S,3S)-4,4-difluoro-3-hydroxy-1-(hydroxyamino)-3-methyl-1-oxobutan-2-yl)benzamide |
| 45 | 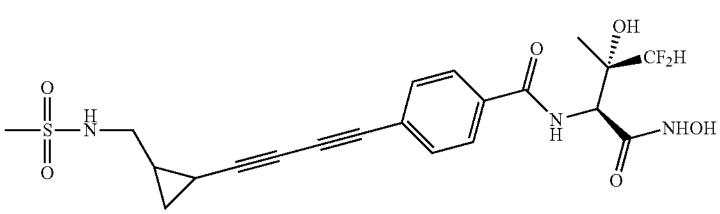 | N-((2S,3S)-4,4-difluoro-3-hydroxy-1-(hydroxyamino)-3-methyl-1-oxobutan-2-yl)-4-((2-(methylsulfonamidomethyl)cyclopropyl)buta-1,3-diyn-1-yl)benzamide |
| 46 | 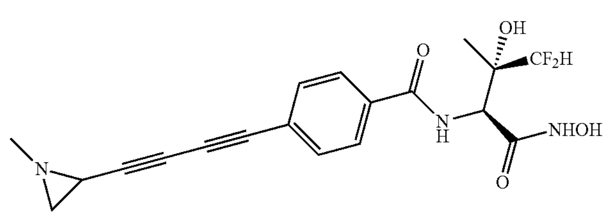 | N-((2S,3S)-4,4-difluoro-3-hydroxy-1-(hydroxyamino)-3-methyl-1-oxobutan-2-yl)-4-((1-methylaziridin-2-yl)buta-1,3-diyn-1-yl)benzamide |

-continued

| Example No. | Compound Structure | Chemical Name |
|---|---|---|
| 47 | 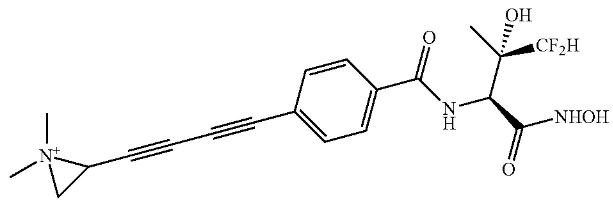 | 2-((4-(((2S,3S)-4,4-difluoro-3-hydroxy-1-(hydroxyamino)-3-methyl-1-oxobutan-2-yl)carbamoyl)phenyl)buta-1,3-diyn-1-yl)-1,1-dimethylaziridin-1-ium |
| 48 | 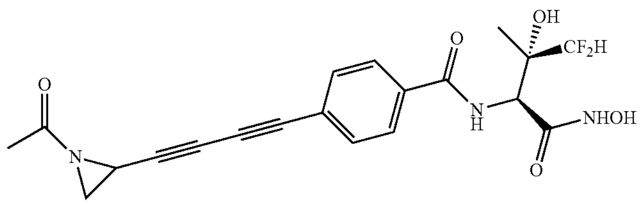 | 4-((1-acetylaziridin-2-yl)buta-1,3-diyn-1-yl)-N-((2S,3S)-4,4-difluoro-3-hydroxy-1-(hydroxyamino)-3-methyl-1-oxobutan-2-yl)benzamide |
| 49 | 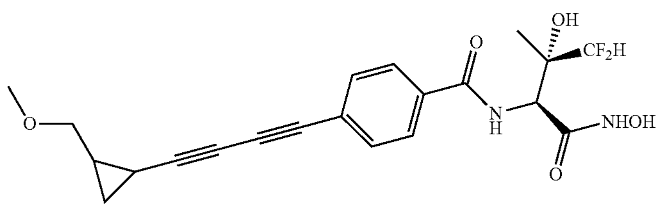 | N-((2S,3S)-4,4-difluoro-3-hydroxy-1-(hydroxyamino)-3-methyl-1-oxobutan-2-yl)-4-((2-(methoxymethyl)cyclopropyl)buta-1,3-diyn-1-yl)benzamide |
| 50 | 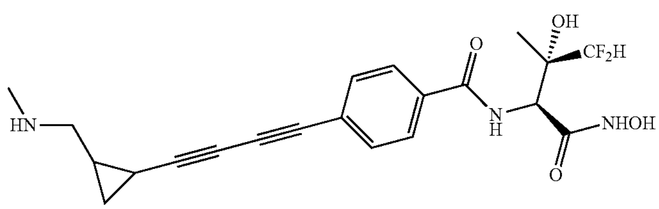 | N-((2S,3S)-4,4-difluoro-3-hydroxy-1-(hydroxyamino)-3-methyl-1-oxobutan-2-yl)-4-((2-((methylamino)methyl)cyclopropyl)-buta-1,3-diyn-1-yl)benzamide |
| 51 | 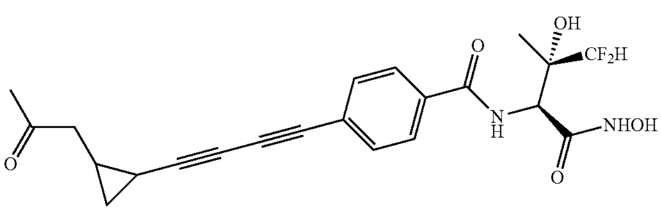 | N-((2S,3S)-4,4-difluoro-3-hydroxy-1-(hydroxyamino)-3-methyl-1-oxobutan-2-yl)-4-((2-(2-oxopropyl)cyclopropyl)buta-1,3-diyn-1-yl)benzamide |
| 52 | 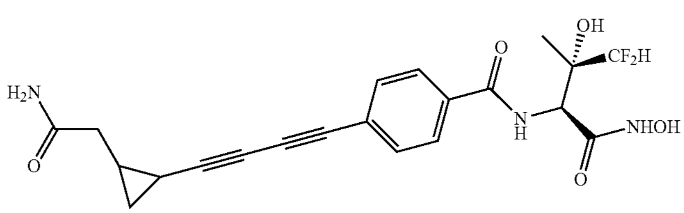 | 4-((2-(2-amino-2-oxo-ethyl)cyclopropyl)-buta-1,3-diyn-1-yl)-N-((2S,3S)-4,4-difluoro-3-hydroxy-1-(hydroxyamino)-3-methyl-1-oxobutan-2-yl)benzamide |
| 53 | 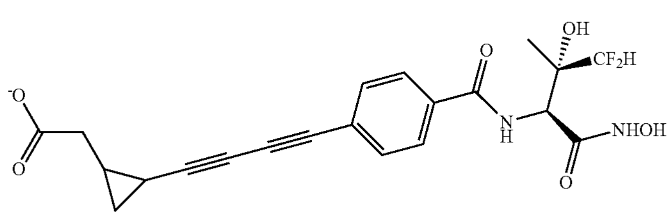 | 2-(2-((4-(((2S,3S)-4,4-difluoro-3-hydroxy-1-(hydroxyamino)-3-methyl-1-oxobutan-2-yl)carbamoyl)phenyl)buta-1,3-diyn-1-yl)cyclopropyl)acetate |

| Example No. | Compound Structure | Chemical Name |
|---|---|---|
| 54 | 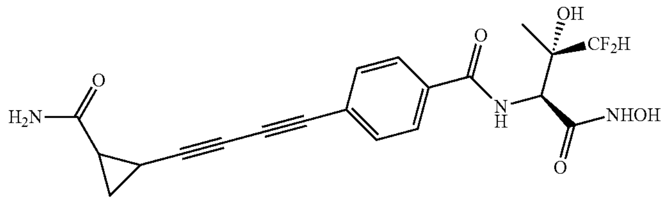 | 4-((2-carbamoylcyclopropyl)buta-1,3-diyn-1-yl)-N-((2S,3S)-4,4-difluoro-3-hydroxy-1-(hydroxyamino)-3-methyl-1-oxobutan-2-yl)benzamide |
| 55 | 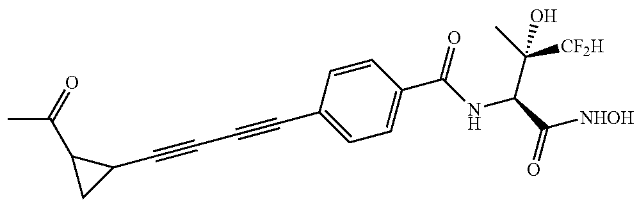 | 4-((2-acetylcyclopropyl)buta-1,3-diyn-1-yl)-N-((2S,3S)-4,4-difluoro-3-hydroxy-1-(hydroxyamino)-3-methyl-1-oxobutan-2-yl)benzamide |

Example 56: Biological Examples

Minimum Inhibitory Concentration (MIC)

Non-piliated variants of the indicated strains of *Neisseria gonorrhoeae* were grown overnight on GCB plates, resuspended in GCB broth with Kellogg's supplements I and II (Kellogg et al. (1963) *Neisseria gonorrhoeae*. I. Virulence genetically linked to colonial variation. J Bacteriol 85, 1274-1279), 10 mM $MgCl_2$, and 20 mM sodium bicarbonate at a final $OD_{600}$ of 0.018 (~$1\times10^7$ cfu/ml). Aliquots (5 µl) of each strain was spotted onto GCB plates containing the compounds at 2-fold dilution intervals. The MIC was defined as the lowest concentration of antibiotic on which fewer than 5 colonies appeared after 24 hrs of incubation.

FA19 is an antibiotic-susceptible strain (Maness, M. J., and Sparling, P. F. (1973) Multiple antibiotic resistance due to a single mutation in *Neisseria gonorrhoeae*. J Infect Dis 128, 321-330). 35/02 is a cephalosporin-intermediate resistant strain of *N. gonorrhoeae* isolated in Sweden in 2002 (Lindberg et al. (2007) *Neisseria gonorrhoeae* isolates with reduced susceptibility to cefixime and ceftriaxone: association with genetic polymorphisms in penA, mtrR, porB1b, and ponA. *Antimicrob Agents Chemother* 51, 2117-2122). This strain contains a mosaic penA gene (encoding variants of Penicillin-Binding Protein 2) associated with cephalosporin resistance, but the strain is not fully resistant. H041 was isolated in 2009 from a female sex worker in Japan with a pharyngeal gonococcal infection that had an MIC of ceftriaxone=2-4 µg/ml (Ohnishi et al. (2011) Is *Neisseria gonorrhoeae* initiating a future era of untreatable gonorrhea? Detailed characterization of the first high-level ceftriaxone resistant strain. *Antimicrob Agents Chemother* 55, 3538-3545). H041 was the first clinical isolate with a confirmed MIC above the resistance breakpoint (>0.25 µg/ml). Lastly, F89 has an MIC of ceftriaxone=2 µg/ml (Unemo et al. (2011) High-level cefixime- and ceftriaxone-resistant *N. gonorrhoeae* in France: novel penA mosaic allele in a successful international clone causes treatment failure. *Antimicrob Agents Chemother* 56, 1273-1280).

"$MIC_{50}$" refers to an amount, concentration or dosage of a particular test compound that achieves a 50% inhibition of a growth of a target organism. Compounds of the invention have MIC values generally ranging from about 0.01 µg/ml to about 400 µg/ml. Representative results are also illustrated in Table 1.

TABLE 1

| Compound | *N. gonorrhoeae* FA19 | *N. gonorrhoeae* 35/02 | *N. gonorrhoeae* F89 | *N. gonorrhoeae* H041 |
|---|---|---|---|---|
| | 0.02 | 0.03 | 0.03 | 0.03 |
| Example 2 | 0.002 | 0.02 | 0.007 | 0.004 |
| Example 4 | 0.016 | 0.063 | 0.008 | 0.026 |

The antibiotic activities of the compounds useful in the methods of the disclosure are evaluated by measurements of minimum inhibitory concentrations (MICs) using *E. coli*, *P. aeruginosa*, *K. pneumoniae* and *B. cepacia*. In vitro activity of Example 4 against different pathogens is shown in Table 2.

TABLE 2

| Clinical Strains | $MIC_{50}$ (μg/ml) | $MIC_{90}$ (μg/ml) |
|---|---|---|
| *E. coli* (n = 10) | 0.02 | 0.02 |
| *P. aeruginosa* (n = 10) | 0.16 | 0.32 |
| *K. pneumoniae* (n = 10) | 0.06 | 0.25 |
| *B. cepacia* (n = 5) | 0.03 | 0.13 |

In Vivo Clearance

Female Mouse Model of Infection: Female BALB/c mice (Charles River Laboratories, NCI Frederick strain of inbred BALB/cAnNCr mice, strain code 555) were allowed to acclimate to the USU animal facility in autoclaved cages and bedding and with autoclaved water and chow for 10 days. After the acclimation period and two days prior to bacterial inoculation (day −4), vaginal smears were stained with a modified Wright's stain (Hem3, Fisher HealthCare Protocol) and examined to identify mice in anestrus or in the diestrus stage of the estrous cycle. Fifty mice in these stages were implanted with 21-day slow-release, 5 mg 17-β estradiol pellets (Innovative Research of America) (Jerse, A. E. (1999) Experimental gonococcal genital tract infection and opacity protein expression in estradiol-treated mice. *Infect Immun* 67, 5699-5708) and given antibiotics to suppress the overgrowth of commensal flora that occurs under estradiol treatment as follows. Streptomycin (STM) (2.4 mg/mouse; Sigma, Product #S6501) was administered via IP injection twice daily on days −4 through −1. Trimethoprim (TMP) (0.4 g/L; MP Biologicals, #195527) was provided in the drinking water on days −4 through day −1, and both TMP and STM (5 g/L) were provided in the drinking water from day 0 through the remainder of the study period. On day −2, mice were inoculated vaginally with 20 μl of strain H041 rpsL suspended in PBS; suspensions were passed through a 1.2 μM filter to remove aggregates and adjusted to the absorbance $A_{600}$ reading at 600 nm ($A_{600}$) that was predicted to be $5 \times 10^5$ CFU/ml, which is the concentration needed to inoculate mice with the number of viable gonococci needed to infect 80% of mice (infectious dose 80; ID80). For H041 rpsL, the ID80 is $1 \times 10^4$ CFU/mouse. To obtain a sufficient number of mice in the desired stage of the estrus cycle on day −4, mice were infected in two groups, three days apart. This time frame allows for mice that were not in diestrus the first time they were swabbed to cycle back to the diestrus phase of the estrus cycle.

Vaginal swabs were quantitatively cultured for Gc on days −1 and 0 following vaginal inoculation to confirm infection prior to treatment. A portion of the swab sample was also inoculated onto HIA agar to monitor commensal flora. Test and control antibiotics administration began on day 0, 2 days post-bacterial inoculation, after the day 0 culture was collected. The test compound Example 3 and vehicle control were administered orally on a total of four consecutive days.

The compound of Example 3 exhibited in vivo efficacy against a $CRO^R$ strain of *N. gonorrhoeae* when administered orally in this experiment. These results support Example 3 as a promising candidate for treating gonorrhea, including infections caused by multidrug resistant, including CRO resistance, *N. gonorrhoeae*.

Figure 2:
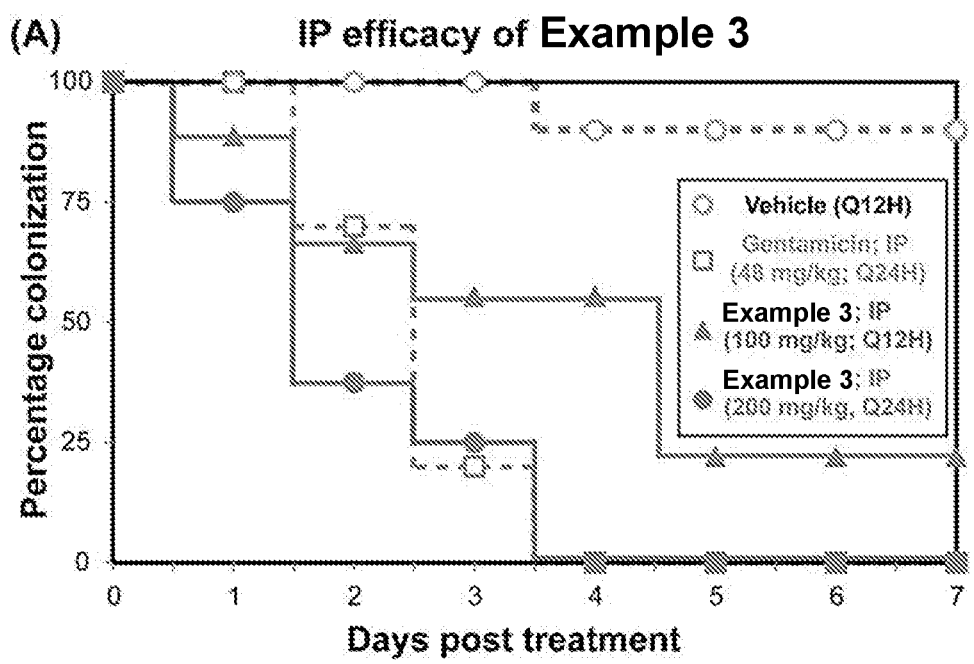
FIG. 2 illustrates in vivo efficacy of Example 3 in the murine gonococcal infection model. (A) efficacy of Example 3 administered intraperitoneally. Please note that once daily treatment (circles) is more effective than the twice daily treatment at half of the dose (triangles). (B) efficacy of Example 3 administrated orally. Mice were infected with multidrug-resistant H041 *N. gonorrhoeae* via an established protocol.
Figure 2:
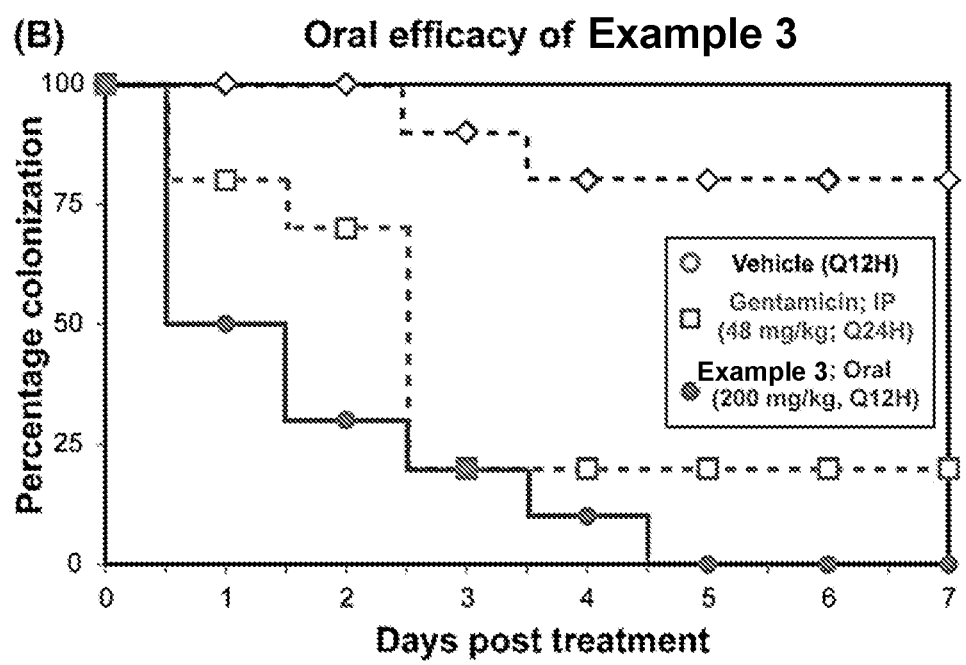
Figure 3:
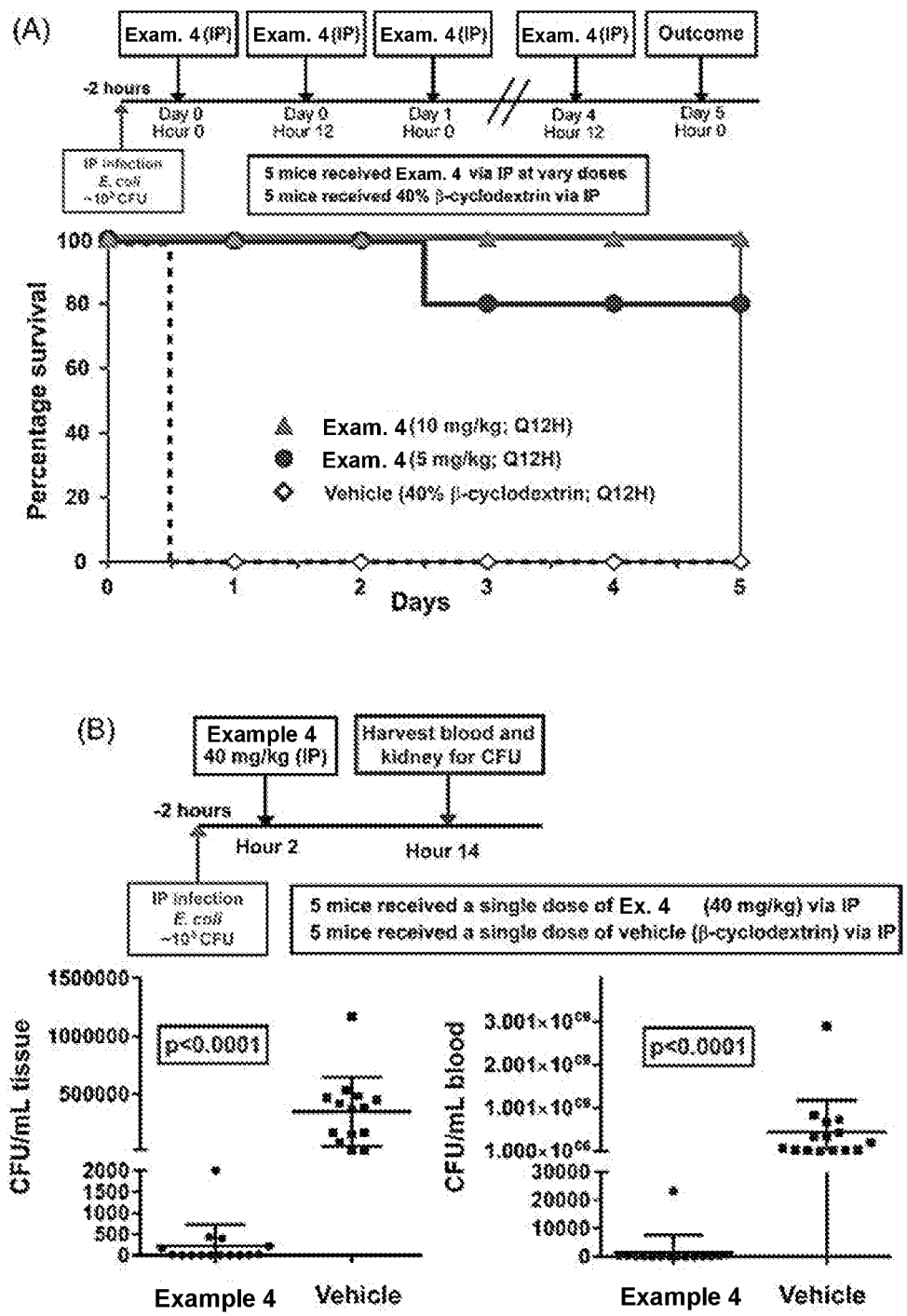
FIG. 3 illustrates in vivo efficacy of Example 4 in the murine *E. coli* sepsis model. (A) dose response curves of Example 4 in a murine intraperitoneal sepsis model. Mice were infected with the *E. coli* strain O18:H7:K1. (B) a single dose of Example 4 cleared *E. coli* infections in the majority of mice.

The clearance results for Example 3 and Example 4 are shown in FIG. 2 and FIG. 3, respectively.

It is understood that the examples and embodiments described herein are for illustrative purposes only and that various modifications or changes in light thereof will be suggested to persons skilled in the art and are to be incorporated within the spirit and purview of this application and scope of the appended claims. All publications, patents, and patent applications cited herein are hereby incorporated herein by reference for all purposes.

What is claimed is:

1. A compound, which is:

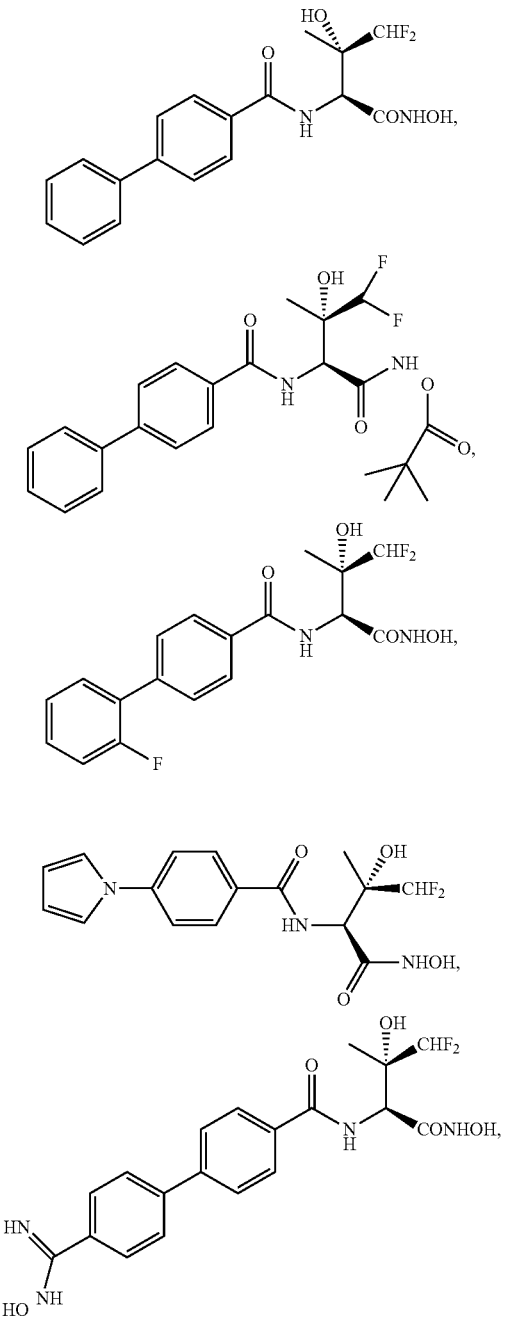

-continued

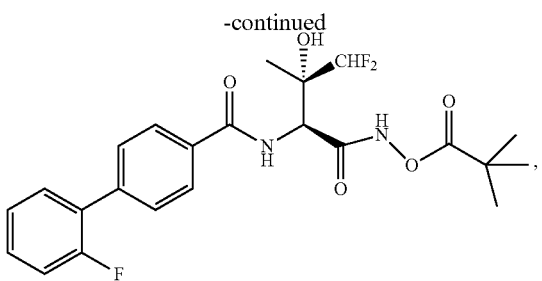

or a pharmaceutically acceptable salt thereof.

2. A compound of the formula:

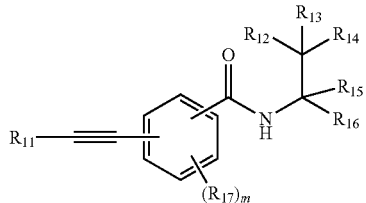

or a pharmaceutically acceptable salt thereof, wherein m is an integer 0, 1, 2, 3, or 4;

$R_{11}$ is —C≡C—$R_{10}$, $C_1$-$C_6$ alkyl, $C_1$-$C_6$ haloalkyl, —CO($C_1$-$C_6$ alkyl), —$C_1$-$C_6$ alkyl-CO($C_1$-$C_6$ alkyl), —$C_1$-$C_6$ alkyl-$CO_2$H, $C_3$-$C_8$ cycloalkyl optionally substituted with $R_{18}$, ($C_3$-$C_8$ cycloalkyl)$C_1$-$C_6$ alkyl- optionally substituted with $R_{18}$, or heterocyclyl optionally substituted with $R_{18}$;

wherein $R_{10}$ is $C_1$-$C_6$ alkyl, $C_1$-$C_6$ haloalkyl, —CO($C_1$-$C_6$ alkyl), —$C_1$-$C_6$ alkyl-CO($C_1$-$C_6$ alkyl), —$C_1$-$C_6$ alkyl-$CO_2$H, $C_3$-$C_8$ cycloalkyl optionally substituted with $R_{19}$, ($C_3$-$C_8$ cycloalkyl)$C_1$-$C_6$ alkyl- optionally substituted with $R_{19}$, or heterocyclyl optionally substituted with $R_{19}$;

$R_{12}$ is selected from the group consisting of halogen, $C_1$-$C_6$ alkyl, $C_1$-$C_6$ haloalkyl, —$NH_2$, —NH($C_1$-$C_6$ alkyl), —N($C_1$-$C_6$ alkyl)$_2$, —OH, $C_1$-$C_6$ alkoxy, $C_1$-$C_6$ haloalkoxy, —SH, —S($C_1$-$C_6$ alkyl), hydroxy($C_1$-$C_6$ alkyl), alkoxy($C_1$-$C_6$ alkyl), and amino($C_1$-$C_6$ alkyl);

$R_{13}$ is selected from the group consisting of halogen, $C_1$-$C_6$ alkyl, $C_1$-$C_6$ haloalkyl, —$NH_2$, —NH($C_1$-$C_6$ alkyl), —N($C_1$-$C_6$ alkyl)$_2$, —OH, $C_1$-$C_6$ alkoxy, $C_1$-$C_6$ haloalkoxy, —SH, —S($C_1$-$C_6$ alkyl), hydroxy($C_1$-$C_6$ alkyl), alkoxy($C_1$-$C_6$ alkyl), amino($C_1$-$C_6$ alkyl), —NHCO($C_1$-$C_6$ alkyl), —$NHCONH_2$, —NHCONH($C_1$-$C_6$ alkyl), —OCO($C_1$-$C_6$ alkyl), and —NHCO($C_1$-$C_6$ alkoxy);

$R_{14}$ is $C_1$-$C_6$ haloalkyl;

$R_{15}$ is independently selected from the group consisting of halogen, —$NO_2$, —CN, $C_1$-$C_6$ alkyl, $C_1$-$C_6$ haloalkyl, —$NH_2$, —NH($C_1$-$C_6$ alkyl), —N($C_1$-$C_6$ alkyl)$_2$, —OH, $C_1$-$C_6$ alkoxy, $C_1$-$C_6$ haloalkoxy, —$CONH_2$, —CON($C_1$-$C_6$ alkyl), —CON($C_1$-$C_6$ alkyl)$_2$, —CONH—OH, —CONH—OCO($C_1$-$C_6$ alkyl), —CONH—$NH_2$, —$CO_2$H, and —$CO_2$($C_1$-$C_6$ alkyl);

$R_{16}$ is hydrogen or $C_1$-$C_6$ alkyl;

each $R_{17}$ is independently selected from the group consisting of halogen, —$NO_2$, —CN, $C_1$-$C_6$ alkyl, $C_1$-$C_6$ haloalkyl, —$NH_2$, —NH($C_1$-$C_6$ alkyl), —N($C_1$-$C_6$ alkyl)$_2$, —OH, $C_1$-$C_6$ alkoxy, and $C_1$-$C_6$ haloalkoxy;

each $R_{18}$ is independently selected from the group consisting of halogen, —$NO_2$, —CN, $C_1$-$C_6$ alkyl, $C_1$-$C_6$ haloalkyl, —$NH_2$, —NH($C_1$-$C_6$ alkyl), —N($C_1$-$C_6$ alkyl)$_2$, —OH, $C_1$-$C_6$ alkoxy, $C_1$-$C_6$ haloalkoxy, —$C_1$-$C_6$ alkyl-OH, —$C_1$-$C_6$ alkyl-($C_1$-$C_6$ alkoxy), —$C_1$-$C_6$ alkyl-$NH_2$, —$C_1$-$C_6$ alkyl-NH—$C_1$-$C_6$ alkyl), —$C_1$-$C_6$ alkyl-N($C_1$-$C_6$ alkyl)$_2$, —$C_1$-$C_6$ alkyl-NH($SO_2$$C_1$-$C_6$ alkyl), —$CONH_2$, —CON($C_1$-$C_6$ alkyl), —CON($C_1$-$C_6$ alkyl)$_2$, —NH($SO_2$$C_1$-$C_6$ alkyl), —CONH—OH, —CONH—OCO($C_1$-$C_6$ alkyl), —C(NH)NH—OH, —CONH—$NH_2$, —CO($C_1$-$C_6$ alkyl), —$CO_2$H, —$CO_2$($C_1$-$C_6$ alkyl), —$C_1$-$C_6$ alkyl-$CONH_2$, —$C_1$-$C_6$ alkyl-CON($C_1$-$C_6$ alkyl), —$C_1$-$C_6$ alkyl-CON($C_1$-$C_6$ alkyl)$_2$, —$C_1$-$C_6$ alkyl-CONH—OH, —$C_1$-$C_6$ alkyl-CO($C_1$-$C_6$ alkyl), —$C_1$-$C_6$ alkyl-$CO_2$H, and —$C_1$-$C_6$ alkyl-$CO_2$($C_1$-$C_6$ alkyl); or two $R_{18}$ groups when attached to the same carbon atom form =O; and each $R_{19}$ is independently selected from the group consisting of halogen, —$NO_2$, —CN, $C_1$-$C_6$ alkyl, $C_1$-$C_6$ haloalkyl, —$NH_2$, —NH($C_1$-$C_6$ alkyl), —N($C_1$-$C_6$ alkyl)$_2$, —OH, $C_1$-$C_6$ alkoxy, $C_1$-$C_6$ haloalkoxy, —$C_1$-$C_6$ alkyl-OH, —$C_1$-$C_6$ alkyl-($C_1$-$C_6$ alkoxy), —$C_1$-$C_6$ alkyl-$NH_2$, —$C_1$-$C_6$ alkyl-NH—$C_1$-$C_6$ alkyl), —$C_1$-$C_6$ alkyl-N($C_1$-$C_6$ alkyl)$_2$, —$C_1$-$C_6$ alkyl-NH($SO_2$$C_1$-$C_6$ alkyl), —$CONH_2$, —CON($C_1$-$C_6$ alkyl), —CON($C_1$-$C_6$ alkyl)$_2$, —NH($SO_2$$C_1$-$C_6$ alkyl), —CONH—OH, —CONH—OCO($C_1$-$C_6$ alkyl), —C(NH)NH—OH, —CONH—$NH_2$, —CO($C_1$-$C_6$ alkyl), —$CO_2$H, —$CO_2$($C_1$-$C_6$ alkyl), —$C_1$-$C_6$ alkyl-$CONH_2$, —$C_1$-$C_6$ alkyl-CON($C_1$-$C_6$ alkyl), —$C_1$-$C_6$ alkyl-CON($C_1$-$C_6$ alkyl)$_2$, —$C_1$-$C_6$ alkyl-CONH—OH, —$C_1$-$C_6$ alkyl-CO($C_1$-$C_6$ alkyl), —$C_1$-$C_6$ alkyl-$CO_2$H, and —$C_1$-$C_6$ alkyl-$CO_2$($C_1$-$C_6$ alkyl); or two $R_{19}$ groups when attached to the same carbon atom form =O.

3. A compound according to claim 2, wherein $R_{14}$ is —$CH_2$F, —$CHF_2$, or —$CF_3$.

4. A compound according to claim 2, wherein $R_{12}$ is halogen, $C_1$-$C_6$ alkyl, or $C_1$-$C_6$ haloalkyl.

5. A compound according to claim 2, wherein $R_{13}$ is selected from the group consisting of —$NH_2$, —NH($C_1$-$C_6$ alkyl), —N($C_1$-$C_6$ alkyl)$_2$, —OH, $C_1$-$C_6$ alkoxy, $C_1$-$C_6$ haloalkoxy, —SH, —S($C_1$-$C_6$ alkyl), —NHCO($C_1$-$C_6$ alkyl), —$NHCONH_2$, —NHCONH($C_1$-$C_6$ alkyl), —OCO($C_1$-$C_6$ alkyl), and —NHCO($C_1$-$C_6$ alkoxy).

6. A compound according to claim 2, wherein $R_{16}$ is hydrogen.

7. A compound according to claim 2, wherein $R_{11}$ is —C≡C—$R_{10}$, and $R_{10}$ is $C_3$-$C_8$ cycloalkyl optionally substituted with $R_{19}$.

8. A compound according to claim 2, wherein Ru is $C_1$-$C_6$ alkyl, $C_1$-$C_6$ haloalkyl, —CO($C_1$-$C_6$ alkyl), —$C_1$-$C_6$ alkyl-CO($C_1$-$C_6$ alkyl), —$C_1$-$C_6$ alkyl-$CO_2$H, $C_3$-$C_8$ cycloalkyl optionally substituted with $R_{18}$, or heterocyclyl optionally substituted with $R_{18}$.

9. A compound according to claim 2, which is:

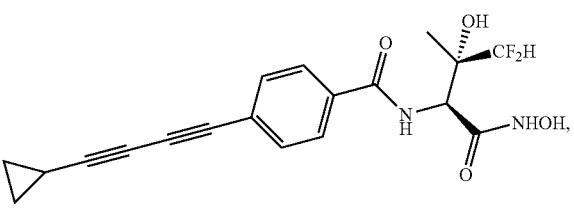

71
-continued
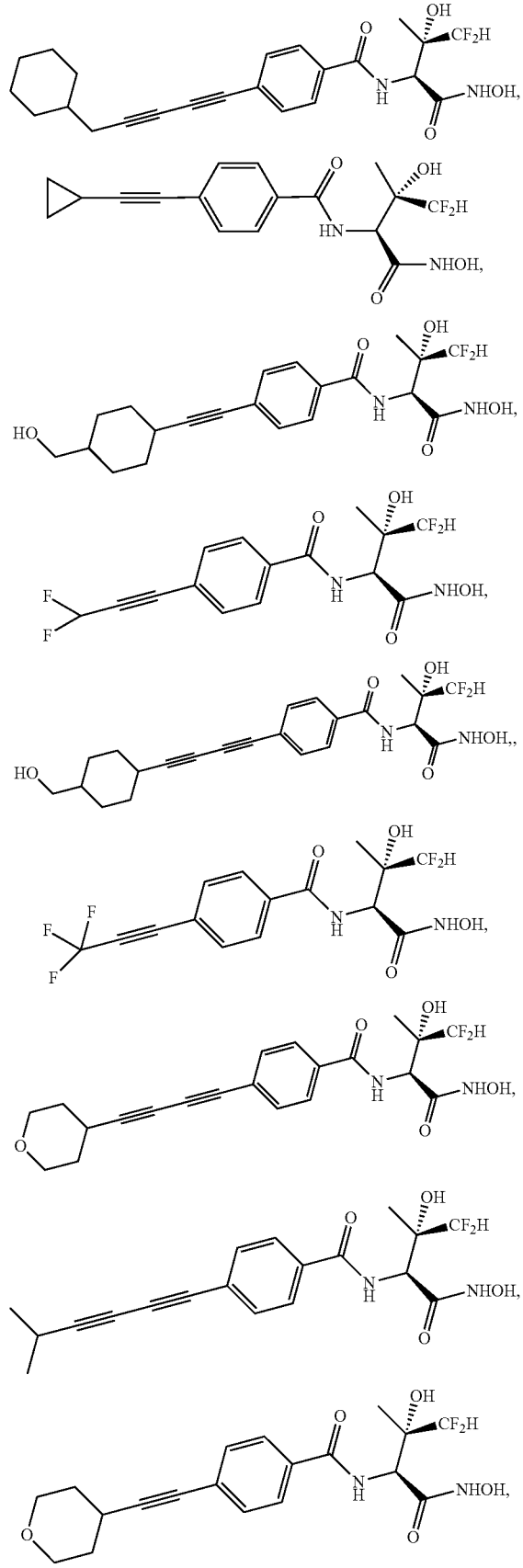
72
-continued
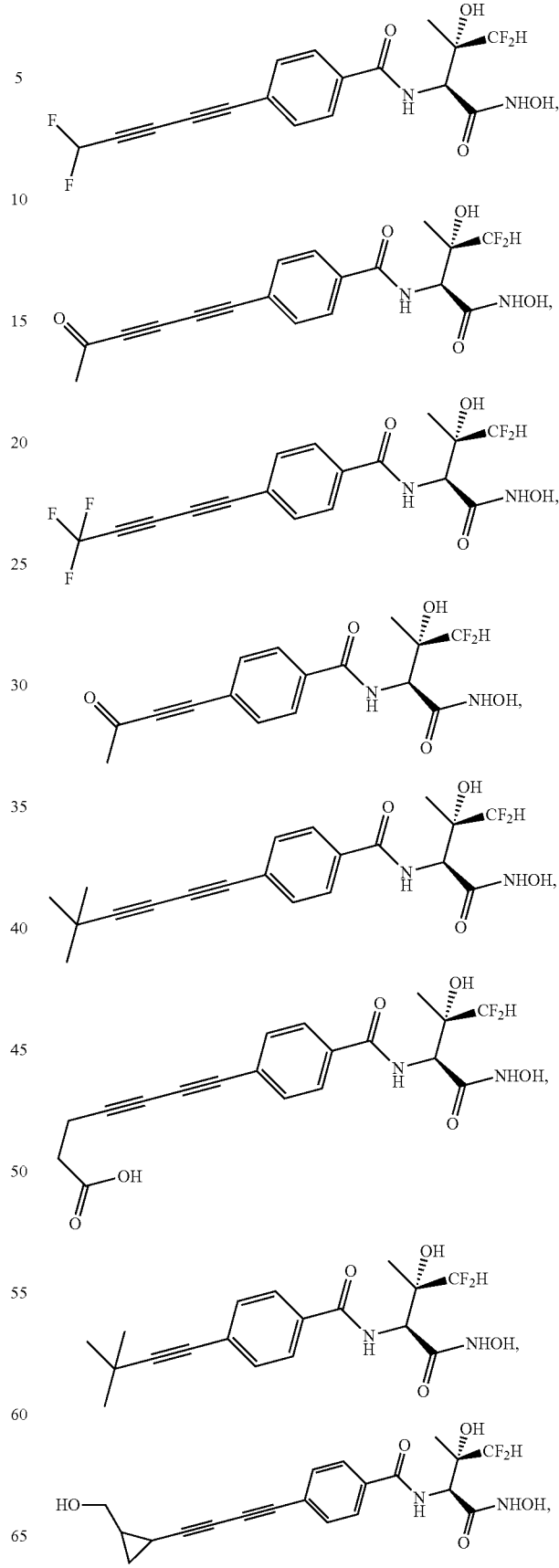

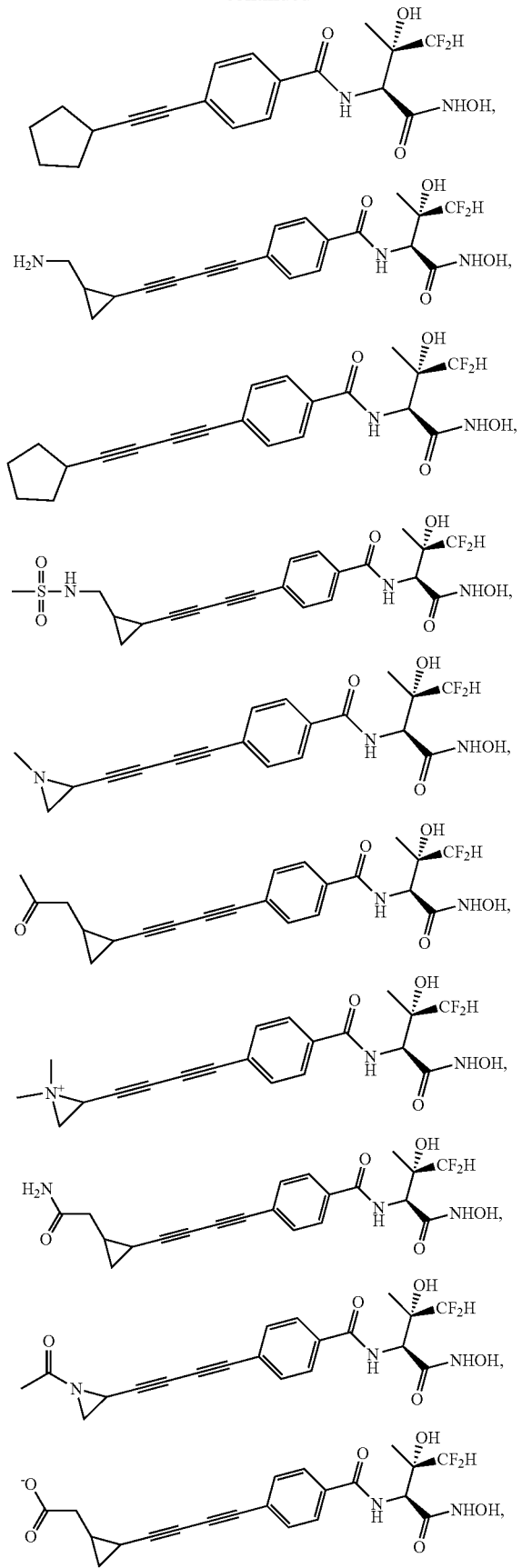
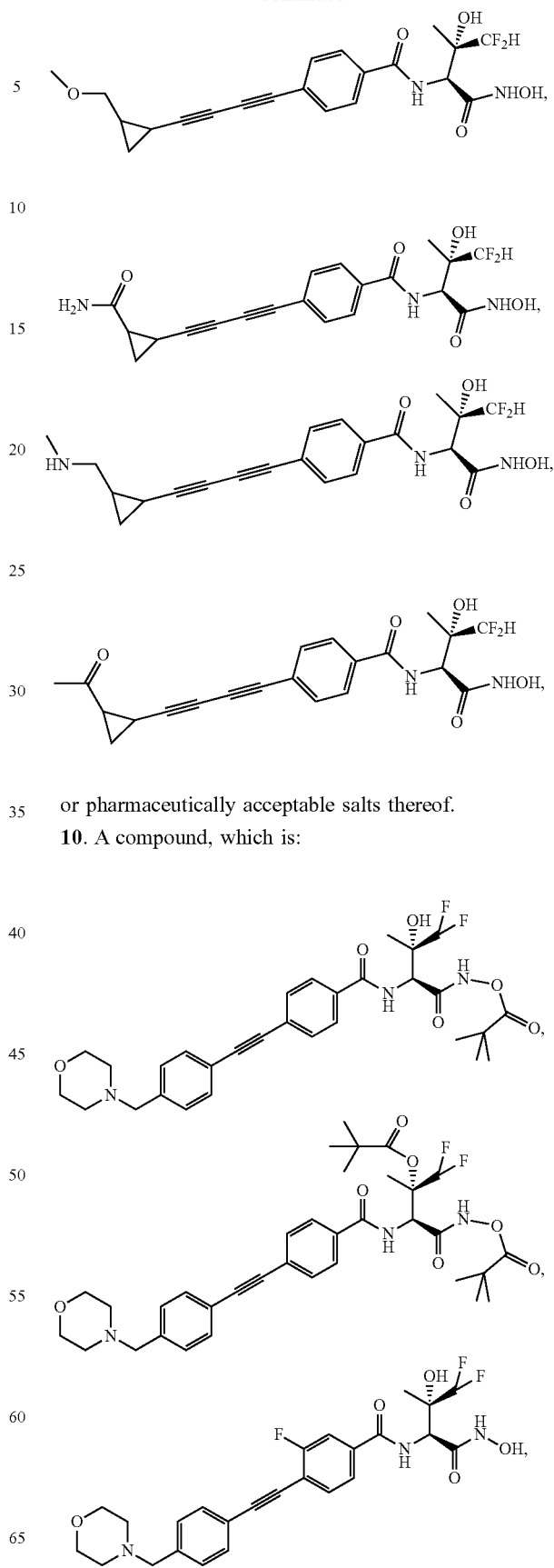
or pharmaceutically acceptable salts thereof.
10. A compound, which is:

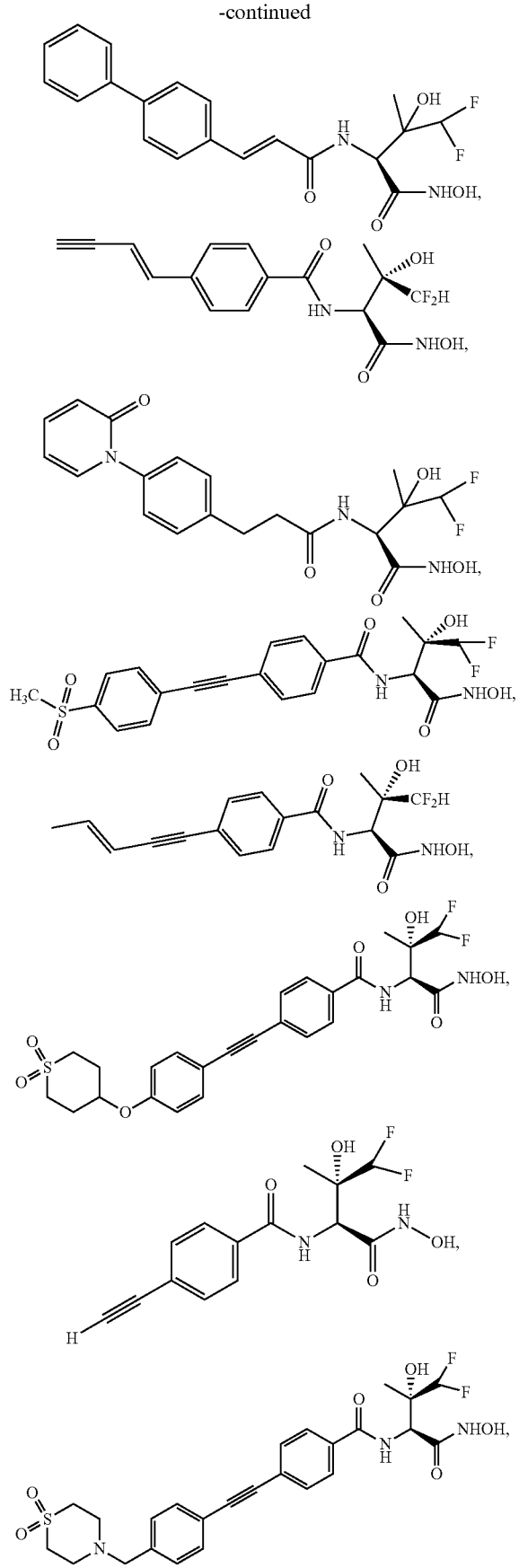
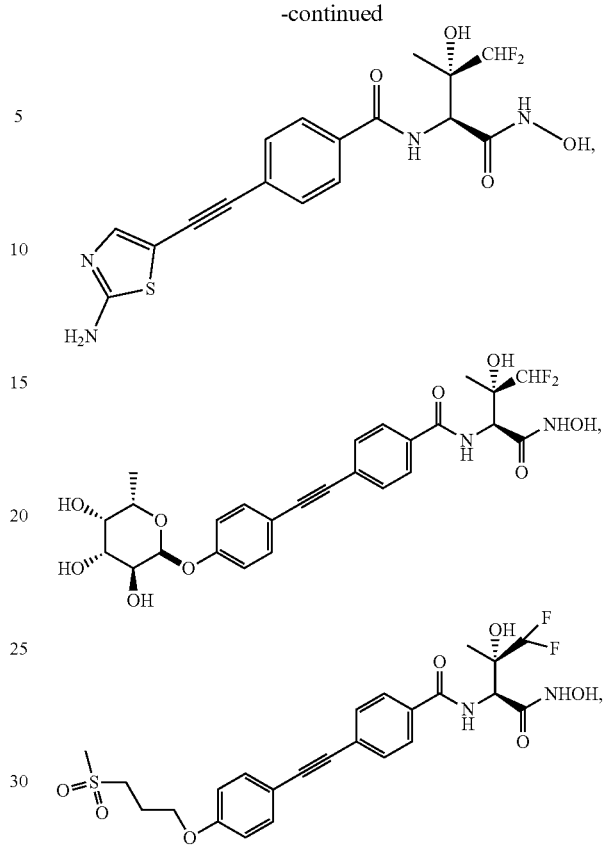

or pharmaceutically acceptable salts thereof.

11. A pharmaceutical composition comprising a compound according to claim 1 and a pharmaceutically acceptable carrier, solvent, adjuvant or diluent.

12. A method of treating Gram-negative bacterial infections, the method comprising administering to a subject in need of such treatment an effective amount of one or more compounds of formula:

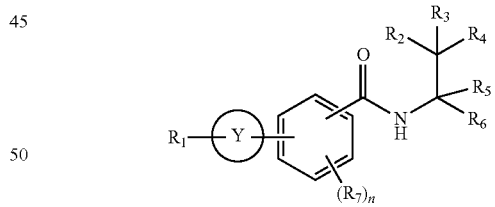

or a pharmaceutically acceptable salt thereof, wherein
Y represents aryl optionally substituted with $R_8$, heteroaryl optionally substituted with $R_8$, or heterocyclyl optionally substituted with $R_8$;
n is an integer 0, 1, 2, 3, or 4;
$R_1$ is hydrogen, $C_1$-$C_6$ alkyl optionally substituted with $R_9$, aryl optionally substituted with $R_9$, heteroaryl optionally substituted with $R_9$, or heterocyclyl optionally substituted with $R_9$;
$R_2$ is selected from the group consisting of halogen, $C_1$-$C_6$ alkyl, $C_1$-$C_6$ haloalkyl, —$NH_2$, —NH($C_1$-$C_6$ alkyl), —N($C_1$-$C_6$ alkyl)$_2$, —OH, $C_1$-$C_6$ alkoxy, $C_1$-$C_6$ haloalkoxy, —SH, —S($C_1$-$C_6$ alkyl), hydroxy($C_1$-$C_6$ alkyl), alkoxy($C_1$-$C_6$ alkyl), and amino($C_1$-$C_6$ alkyl);

R$_3$ is selected from the group consisting of halogen, C$_1$-C$_6$ alkyl, C$_1$-C$_6$ haloalkyl, —NH$_2$, —NH(C$_1$-C$_6$ alkyl), —N(C$_1$-C$_6$ alkyl)$_2$, —OH, C$_1$-C$_6$ alkoxy, C$_1$-C$_6$ haloalkoxy, —SH, —S(C$_1$-C$_6$ alkyl), hydroxy(C$_1$-C$_6$ alkyl), alkoxy(C$_1$-C$_6$ alkyl), amino(C$_1$-C$_6$ alkyl), —NHCO(C$_1$-C$_6$ alkyl), —NHCONH$_2$, —NHCONH(C$_1$-C$_6$ alkyl), —OCO(C$_1$-C$_6$ alkyl), and —NHCO(C$_1$-C$_6$ alkoxy);

R$_4$ is C$_1$-C$_6$ haloalkyl;

R$_5$ is independently selected from the group consisting of halogen, —NO$_2$, —CN, C$_1$-C$_6$ alkyl, C$_1$-C$_6$ haloalkyl, —NH$_2$, —NH(C$_1$-C$_6$ alkyl), —N(C$_1$-C$_6$ alkyl)$_2$, —OH, C$_1$-C$_6$ alkoxy, C$_1$-C$_6$ haloalkoxy, —CONH$_2$, —CON(C$_1$-C$_6$ alkyl), —CON(C$_1$-C$_6$ alkyl)$_2$, —CONH—OH, —CONH—OCO(C$_1$-C$_6$ alkyl), —CONH—NH$_2$, —CO$_2$H, and —CO$_2$(C$_1$-C$_6$ alkyl);

R$_6$ is hydrogen or C$_1$-C$_6$ alkyl;

each R$_7$ is independently selected from the group consisting of halogen, —NO$_2$, —CN, C$_1$-C$_6$ alkyl, C$_1$-C$_6$ haloalkyl, —NH$_2$, —NH(C$_1$-C$_6$ alkyl), —N(C$_1$-C$_6$ alkyl)$_2$, —OH, C$_1$-C$_6$ alkoxy, and C$_1$-C$_6$ haloalkoxy;

each R$_8$ is independently selected from the group consisting of halogen, —NO$_2$, —CN, C$_1$-C$_6$ alkyl, C$_1$-C$_6$ haloalkyl, —NH$_2$, —NH(C$_1$-C$_6$ alkyl), —N(C$_1$-C$_6$ alkyl)$_2$, —OH, C$_1$-C$_6$ alkoxy, C$_1$-C$_6$ haloalkoxy, —CONH$_2$, —CON(C$_1$-C$_6$ alkyl), —CON(C$_1$-C$_6$ alkyl)$_2$, —CONH—OH, —CONH—OCO(C$_1$-C$_6$ alkyl), —C(NH)NH—OH, —CONH—NH$_2$, —CO$_2$H, and —CO$_2$(C$_1$-C$_6$ alkyl); or two R$_8$ groups when attached to the same carbon atom form =O; and each R$_9$ is independently selected from the group consisting of halogen, —NO$_2$, —CN, C$_1$-C$_6$ alkyl, C$_1$-C$_6$ haloalkyl, —NH$_2$, —NH(C$_1$-C$_6$ alkyl), —N(C$_1$-C$_6$ alkyl)$_2$, —OH, C$_1$-C$_6$ alkoxy, and C$_1$-C$_6$ haloalkoxy; or two R$_9$ groups when attached to the same carbon atom form =O.

13. A pharmaceutical composition comprising a compound according to claim 2 and a pharmaceutically acceptable carrier, solvent, adjuvant or diluent.

14. A method of treating Gram-negative bacterial infections, the method comprising administering to a subject in need of such treatment an effective amount of one or more compounds according to claim 2.

15. A compound according to claim 2, wherein R$_{11}$ is —C≡C—R$_{10}$, and R$_{10}$ is —CO(C$_1$-C$_6$ alkyl), —C$_1$-C$_6$ alkyl-CO(C$_1$-C$_6$ alkyl), —C$_1$-C$_6$ alkyl-CO$_2$H, C$_3$-C$_8$ cycloalkyl optionally substituted with R$_{19}$, or (C$_3$-C$_8$ cycloalkyl)C$_1$-C$_6$ alkyl- optionally substituted with R$_{19}$.

16. A compound according to claim 2, wherein the compound is of formula:

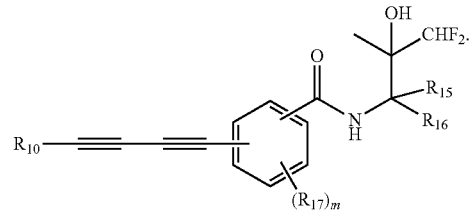

17. A compound according to claim 16, wherein R$_{10}$ is —CO(C$_1$-C$_6$ alkyl), —C$_1$-C$_6$ alkyl-CO(C$_1$-C$_6$ alkyl), —C$_1$-C$_6$ alkyl-CO$_2$H, C$_3$-C$_8$ cycloalkyl optionally substituted with R$_{19}$, or (C$_3$-C$_8$ cycloalkyl)C$_1$-C$_6$ alkyl- optionally substituted with R$_{19}$.

18. A compound according to claim 16, wherein R$_{10}$ is C$_3$-C$_8$ cycloalkyl optionally substituted with R$_{19}$; or R$_{10}$ is cyclopropyl, cyclopentyl, or cyclohexyl, each optionally substituted with R$_{19}$.

19. A compound according to claim 2, wherein R$_{15}$ —CONH—OH, —CONH—NH$_2$, or —CONH—OCO(C$_1$-C$_6$ alkyl).

20. A compound according to claim 2, wherein each R$_{18}$ is independently selected from the group consisting of halogen, C$_1$-C$_6$ alkyl, C$_1$-C$_6$ haloalkyl, —NH$_2$, —NH(C$_1$-C$_6$ alkyl), —N(C$_1$-C$_6$ alkyl)$_2$, —OH, C$_1$-C$_6$ alkoxy, C$_1$-C$_6$ haloalkoxy, —C$_1$-C$_6$ alkyl-OH, —C$_1$-C$_6$ alkyl-(C$_1$-C$_6$ alkoxy), —C$_1$-C$_6$ alkyl-NH$_2$, —C$_1$-C$_6$ alkyl-NH—C$_1$-C$_6$ alkyl), —C$_1$-C$_6$ alkyl-N(C$_1$-C$_6$ alkyl)$_2$, —C$_1$-C$_6$ alkyl-NH(SO$_2$C$_1$-C$_6$ alkyl), —CONH$_2$, —CON(C$_1$-C$_6$ alkyl), —CON(C$_1$-C$_6$ alkyl)$_2$, —CO(C$_1$-C$_6$ alkyl), —CO$_2$H, —CO$_2$(C$_1$-C$_6$ alkyl), —C$_1$-C$_6$ alkyl-CONH$_2$, —C$_1$-C$_6$ alkyl-CON(C$_1$-C$_6$ alkyl), —C$_1$-C$_6$ alkyl-CON(C$_1$-C$_6$ alkyl)$_2$, —C$_1$-C$_6$ alkyl-CO(C$_1$-C$_6$ alkyl), —C$_1$-C$_6$ alkyl-CO$_2$H, and —C$_1$-C$_6$ alkyl-CO$_2$(C$_1$-C$_6$ alkyl); and each R$_{19}$ is independently selected from the group consisting of halogen, C$_1$-C$_6$ alkyl, C$_1$-C$_6$ haloalkyl, —NH$_2$, —NH(C$_1$-C$_6$ alkyl), —N(C$_1$-C$_6$ alkyl)$_2$, —OH, C$_1$-C$_6$ alkoxy, C$_1$-C$_6$ haloalkoxy, —C$_1$-C$_6$ alkyl-OH, —C$_1$-C$_6$ alkyl-(C$_1$-C$_6$ alkoxy), —C$_1$-C$_6$ alkyl-NH$_2$, —C$_1$-C$_6$ alkyl-NH—C$_1$-C$_6$ alkyl), —C$_1$-C$_6$ alkyl-N(C$_1$-C$_6$ alkyl)$_2$, —C$_1$-C$_6$ alkyl-NH(SO$_2$C$_1$-C$_6$ alkyl), —CONH$_2$, —CON(C$_1$-C$_6$ alkyl), —CON(C$_1$-C$_6$ alkyl)$_2$, —CO(C$_1$-C$_6$ alkyl), —CO$_2$H, —CO$_2$(C$_1$-C$_6$ alkyl), —C$_1$-C$_6$ alkyl-CONH$_2$, —C$_1$-C$_6$ alkyl-CON(C$_1$-C$_6$ alkyl), —C$_1$-C$_6$ alkyl-CON(C$_1$-C$_6$ alkyl)$_2$, —C$_1$-C$_6$ alkyl-CO(C$_1$-C$_6$ alkyl), —C$_1$-C$_6$ alkyl-CO$_2$H, and —C$_1$-C$_6$ alkyl-CO$_2$(C$_1$-C$_6$ alkyl).

* * * * *